US009496585B2

(12) United States Patent
Sawa et al.

(10) Patent No.: US 9,496,585 B2
(45) Date of Patent: Nov. 15, 2016

(54) NONAQUEOUS ELECTROLYTE SOLUTION AND NONAQUEOUS ELECTROLYTE BATTERY USING SAME

(71) Applicant: MITSUBISHI CHEMICAL CORPORATION, Chiyoda-ku (JP)

(72) Inventors: Shuhei Sawa, Ibaraki (JP); Minoru Kotato, Mie (JP); Kunihisa Shima, Mie (JP); Masamichi Onuki, Kanagawa (JP); Youichi Ohashi, Ibaraki (JP); Kazuki Watanabe, Kanagawa (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 309 days.

(21) Appl. No.: 13/865,560

(22) Filed: Apr. 18, 2013

(65) Prior Publication Data

US 2013/0224578 A1    Aug. 29, 2013

Related U.S. Application Data

(63) Continuation of application No. PCT/JP2011/073849, filed on Oct. 17, 2011.

(30) Foreign Application Priority Data

Oct. 18, 2010  (JP) ................................. 2010-233513

(51) Int. Cl.
| | |
|---|---|
| *H01M 6/16* | (2006.01) |
| *H01M 10/056* | (2010.01) |
| *H01M 10/0525* | (2010.01) |
| *H01M 10/0567* | (2010.01) |
| *H01M 10/0569* | (2010.01) |
| *C07C 309/67* | (2006.01) |

(52) U.S. Cl.
CPC .......... *H01M 10/056* (2013.01); *C07C 309/67* (2013.01); *H01M 10/0525* (2013.01); *H01M 10/0567* (2013.01); *H01M 10/0569* (2013.01); *Y02E 60/122* (2013.01)

(58) Field of Classification Search
CPC .. H01M 6/14; H01M 6/168; H01M 10/0562; H01M 10/0564; H01M 10/0567; H01M 10/0568; H01M 10/056
See application file for complete search history.

(56) References Cited

U.S. PATENT DOCUMENTS

| | | | |
|---|---|---|---|
| 5,626,981 A | 5/1997 | Simon et al. | |
| 6,436,582 B1 * | 8/2002 | Hamamoto et al. | 429/340 |
| 8,053,109 B2 * | 11/2011 | Iwanaga et al. | 429/199 |
| 2010/0015514 A1 | 1/2010 | Miyagi et al. | |
| 2011/0159377 A1 * | 6/2011 | Lee et al. | 429/306 |
| 2011/0229773 A1 * | 9/2011 | Cho et al. | 429/338 |
| 2012/0244425 A1 | 9/2012 | Tokuda | |
| 2012/0301797 A1 * | 11/2012 | Abe | H01M 10/052 429/338 |
| 2013/0084493 A1 | 4/2013 | Tokuda | |

FOREIGN PATENT DOCUMENTS

| | | |
|---|---|---|
| JP | 8-45545 | 2/1996 |
| JP | 9-245834 | 9/1997 |
| JP | 10-325987 | 12/1998 |
| JP | 2000-133304 | 5/2000 |
| JP | 2000-195545 | 7/2000 |
| JP | 2003-203673 | 7/2003 |
| JP | 2006-4811 | 1/2006 |
| JP | 2007-184257 | 7/2007 |
| JP | 2008-251259 | 10/2008 |
| JP | 2010-507896 | 3/2010 |
| JP | 2010-529633 | 8/2010 |
| JP | 2011-96643 | 5/2011 |
| JP | 2011-238373 | 11/2011 |
| KR | 10-2009-0040214 | 4/2009 |
| WO | WO 2010/110159 A1 | 9/2010 |
| WO | WO 2011-096450 | 8/2011 |

OTHER PUBLICATIONS

International Search Report issued Jan. 31, 2012, in International Application No. PCT/JP2011/073849.
Office Action issued Sep. 1, 2015, in Japanese patent application No. 2012-539723 (w/English translation).
Office Action issued Feb. 23, 2016 in Japanese Patent Application No. 2012-539723 (with English language translation).

* cited by examiner

*Primary Examiner* — Patrick Ryan
*Assistant Examiner* — Julian Anthony
(74) *Attorney, Agent, or Firm* — Oblon, McClelland, Maier & Neustadt, L.L.P.

(57) ABSTRACT

The present invention relates to a nonaqueous electrolyte solution comprising a lithium salt and a nonaqueous organic solvent, wherein the nonaqueous electrolyte solution comprises a specific sulfonic acid ester.

8 Claims, No Drawings

NONAQUEOUS ELECTROLYTE SOLUTION AND NONAQUEOUS ELECTROLYTE BATTERY USING SAME

TECHNICAL FIELD

The present invention relates to a nonaqueous electrolyte solution and a nonaqueous electrolyte battery using the same.

BACKGROUND ART

With the rapid progress of a portable electronic device such as cellular phone and notebook computer, demands for increasing the capacity of a battery used in its main power supply or backup power supply are increasing, and a nonaqueous electrolyte battery such as lithium ion secondary battery having a high energy density as compared with a nickel•cadmium battery or a nickel•hydrogen battery is attracting attention.

A representative example of the electrolyte solution for a lithium ion secondary battery is a nonaqueous electrolyte solution prepared by dissolving an electrolyte such as $LiPF_6$, $LiBF_4$, $LiN(CF_3SO_2)_2$ and $LiCF_3(CF_2)_3SO_3$ in a mixed solvent consisting of a high-permittivity solvent such as ethylene carbonate and propylene carbonate and a low-viscosity solvent such as dimethyl carbonate, diethyl carbonate and ethyl methyl carbonate.

As for the negative electrode active material of a lithium ion secondary battery, a carbonaceous material capable of occluding•releasing a lithium ion is mainly used, and representative examples thereof include natural graphite, artificial graphite, and amorphous carbon. With an attempt to more increase the capacity, a metal- or alloy-based negative electrode using silicone, tin or the like is also known. As for the positive electrode active material, a transition metal composite oxide capable of occluding•releasing a lithium ion is mainly used, and representative examples of the transition metal include cobalt, nickel, manganese, and iron.

Such a lithium ion secondary battery uses positive and negative electrodes having high activity and therefore, it is known that the charge/discharge capacity is reduced by a side reaction of the electrode with the electrolyte solution. In order to improve battery characteristics, various studies are being made on the nonaqueous solvent or electrolyte.

Patent Document 1 has proposed using a vinylene carbonate or its derivative, where a cyclic carbonate having a double bond preferentially reacts with the negative electrode to form a high-quality film on the negative electrode surface and the storage characteristics and cycle characteristics of the battery are thereby enhanced.

Patent Document 2 has proposed using a nonaqueous electrolyte solution containing an alkyl alkanesulfonate compound, where a film having high lithium ion permeability is formed by a reaction on the carbon electrode surface and the charge/discharge cycle life is thereby enhanced.

Patent Documents 3 and 4 have proposed using a nonaqueous electrolyte solution containing an alkynyl alkanesulfonate compound or a dialkylsulfonic acid ester, where a passivation film is formed on the carbon negative electrode surface and the charge/discharge cycle life is thereby enhanced.

RELATED ART

Patent Document

Patent Document 1: JP-A-8-045545 (the term "JP-A" as used herein means an "unexamined published Japanese patent application")

Patent Document 2: JP-A-9-245834
Patent Document 3: JP-A-2000-195545
Patent Document 4: JP-A-2000-133304

SUMMARY OF THE INVENTION

Problems that the Invention is to Solve

However, demands for high performance of a battery are recently more and more increasing, and it is required to achieve various battery characteristics such as high capacity, high-temperature storage characteristics and cycle characteristics at high levels.

As to the method for realizing high capacity, there is studied, for example, a method where the active material layer of the electrode is pressurized to increase the density and minimize the volume occupied by a material other than the active material in the inside of the battery, or a method of expanding the use range of the positive electrode to allow for utilization up to a high potential. However, when the active material layer of the electrode is pressurized to increase the density, it becomes difficult to uniformly utilize the active material, and this is liable to cause a problem that lithium is partially precipitated due to a non-uniform reaction or deterioration of the active material is accelerated, failing in obtaining adequate characteristics. Also, when the use range of the positive electrode is expanded to allow for utilization up to a high potential, the positive electrode becomes more active to readily cause a problem that deterioration is accelerated by a reaction between the positive electrode and the electrolyte solution. In particular, it is known that when the battery in a charging state is stored under high-temperature conditions, the battery capacity is reduced due to a side reaction of the electrode with the electrolyte solution, and in order to improve storage characteristics, various studies are being made on the nonaqueous solvent or electrolyte.

Furthermore, an increase in the capacity leads to a decrease in the space inside the battery, and this also causes a problem that the internal pressure of the battery is significantly increased even when a small amount of a gas is generated by the decomposition of the electrolyte solution.

It is required to reduce such deterioration of the battery characteristics, but when the additive described in Patent Document 1 and 2 is incorporated into the nonaqueous electrolyte, a side reaction of the additive simultaneously proceeds on the positive electrode, as a result, the initial capacity or high-temperature storage characteristics may be reduced.

Also, even when the additive described in Patent Documents 3 and 4 is incorporated into the nonaqueous electrolyte, the reaction of the electrolyte solution on the negative electrode cannot be completely inhibited, and the cycle characteristics are still unsatisfied. In particular, with respect to the high-temperature storage characteristics, inhibition of gas evolution is required, but it has been impossible for conventional techniques to satisfy both inhibition of deterioration in battery characteristics and inhibition of gas evolution at the same time.

The present invention has been made under these circumstances, and an object of the present invention is to provide a nonaqueous electrolyte solution capable of giving a nonaqueous electrolyte battery prevented from capacity deterioration and gas evolution during high-temperature storage, and a nonaqueous electrolyte battery using the nonaqueous electrolyte solution.

Means for Solving the Problems

As a result of repeating various studies to attain the above-described object, the present inventors have found that by incorporating a specific compound into the electrolyte solution, those problems can be solved. The present invention has been accomplished based on this finding.

That is, the gist of the present invention is as follows.

(a) A nonaqueous electrolyte solution comprising a lithium salt and a nonaqueous organic solvent, wherein the nonaqueous electrolyte solution comprises a sulfonic acid ester represented by formula (1):

[Chem. 1]

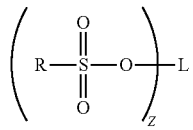
(1)

(wherein L represents a Z-valent organic group which may have a substituent;
R represents a chain hydrocarbon group having an unsaturated bond, which may have a substituent; and
Z is an integer of 1 or more, and when Z is 2 or more, each R may be the same as or different from each other;
provided that a case where R is a vinyl group and L is an alkyl group and a case where R and L are an allyl group, are excluded, and that R and L do not combine with each other to form a ring).

(b) The nonaqueous electrolyte solution as described in (a), wherein in formula (1), L is any one organic group selected form the group consisting of an alkyl group, an alkylene group, an alkenyl group, an alkenylene group, an alkynyl group and an alkynylene group, each having a carbon number of 1 to 8, which may have a substituent, and
R is an alkenyl group or an alkynyl group, each having a carbon number of 2 to 8, which may have a substituent,
provided that a case where R is a vinyl group and L is an alkyl group and a case where R and L are an allyl group are excluded.

(c) The nonaqueous electrolyte solution as described in (a), wherein in formula (1), L is any one organic group selected form the group consisting of an alkylene group, an alkenyl group, an alkenylene group, an alkynyl group and an alkynylene group, which may have a substituent, and
R is any one group selected from the group consisting of a vinyl group, an allyl group and a propargyl group, which may have a substituent,
provided that a case where R and L are an allyl group is excluded.

(d) The nonaqueous electrolyte solution as described in (a), wherein in formula (1), L is any one organic group selected form the group consisting of an alkylene group, an alkenyl group, an alkenylene group, an alkynyl group and an alkynylene group, which may have a substituent, and
R is any one group selected from the group consisting of a vinyl group, an allyl group and a propargyl group, which may have a substituent,
provided that a case where L is an allyl group is excluded.

(e) The nonaqueous electrolyte solution as described in (a), wherein in formula (1), L is any one organic group selected form the group consisting of an alkylene group, a vinyl group, an alkenylene group, an alkynyl group and an alkynylene group, which may have a substituent, and
R is any one group selected from the group consisting of a vinyl group, an allyl group and a propargyl group, which may have a substituent.

(f) The nonaqueous electrolyte solution as described in any one of (a) to (e), which comprises the sulfonic acid ester represented by formula (1) in an amount of 0.001 to 10 mass %.

(g) The nonaqueous electrolyte solution as described in any one of (a) to (f), which comprises the sulfonic acid ester represented by formula (1) and at least one compound selected from the group consisting of a fluorine atom-containing cyclic carbonate, a carbon-carbon unsaturated bond-containing cyclic carbonate, a monofluorophosphate, a difluorophosphate, an isocyanate compound, a cyclic sulfonic acid ester and a nitrile compound.

(h) The nonaqueous electrolyte solution as described in (g), which comprises a fluorine atom-containing cyclic carbonate in an amount of 1 to 50 mass %.

(i) The nonaqueous electrolyte solution as described in (g) or (h), wherein the fluorine atom-containing cyclic carbonate is at least one compound selected from the group consisting of monofluoroethylene carbonate, 4,4-difluoroethylene carbonate, 4,5-difluoroethylene carbonate and 4,5-difluoro-4,5-dimethylethylene carbonate.

(j) A nonaqueous electrolyte battery comprising negative and positive electrodes capable of occluding-releasing a lithium ion and a nonaqueous electrolyte solution, wherein the nonaqueous electrolyte solution is the nonaqueous electrolyte solution described in any one of (a) to (i).

(k) A sulfonic acid ester represented by either the following formula (2) or (3):

[Chem. 2]

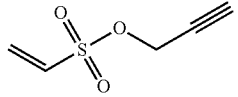
(2)

[Chem. 3]

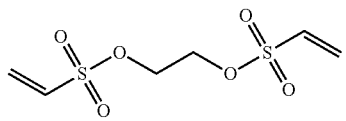
(3)

Advantage of the Invention

In the present invention, as one of characteristic features, a sulfonic acid ester having a specific structure is used for a nonaqueous electrolyte battery. Usually, an alkyl alkanesulfonate compound as typified by Patent Document 2 reacts on an electrode and thereby enhances the battery characteristics. However, electrode deterioration due to a side reaction proceeds at the same time. Also, an alkynyl alkanesulfonate compound or a dialkylsulfonic acid ester as typified by Patent Documents 3 and 4 forms a passivation film on the negative electrode, but the stability thereof is low and it is impossible to completely inhibit the reaction of an electrolyte solution on the negative electrode. For these reasons, there is a problem that even when such an additive is incorporated into a nonaqueous electrolyte, storage characteristics and cycle characteristics of the battery are insufficient.

The present inventors have taken note of this point and found that the stability of a film formed on the negative electrode is greatly improved by introducing an unsaturated bond into the sulfonic acid moiety and furthermore, the effect of enhancing high-temperature storage characteristics or enhancing cycle characteristics is outstandingly brought out by selecting the ester moiety. The present invention has been accomplished based on this finding.

MODE FOR CARRYING OUT THE INVENTION

The mode for carrying out the present invention is described below, but the present invention is not limited to the following embodiments and can be implemented by making any modifications therein without departing from the purport of the present invention.

Here, "wt %", "ppm by weight" and "parts by weight" have the same meanings as "mass %", "ppm by mass" and "parts by mass", respectively. Also, when simply referred to as ppm, this indicates "ppm by weight".

1. Nonaqueous Electrolyte Solution 1-1. Sulfonic Acid Ester Represented by Formula (1)

The present invention is characterized by containing a sulfonic acid ester represented by the following formula (1) in a nonaqueous electrolyte solution.

[Chem. 4]

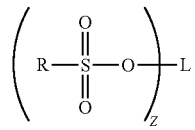

(1)

In the formula, L represents a Z-valent organic group which may have a substituent.

R represents a chain hydrocarbon group having an unsaturated bond, which may have a substituent.

Z is an integer of 1 or more, and when Z is 2 or more, each R may be the same as or different from every other R.

However, a case where R is a vinyl group and L is an alkyl group and a case where R and L are an allyl group are excluded. Incidentally, R and L do not combine with each other to form a ring.

Here, the organic group in L of formula (1) indicates a functional group composed of an atom selected from the group consisting of a carbon atom, a hydrogen atom, a nitrogen atom, an oxygen atom and a halogen atom, and the carbon number of the organic group is preferably 1 to 10.

Specific examples of the substituent include an alkyl group, an alkenyl group, an alkynyl group, an aryl group, an alkoxy group, a nitrile group, an isocyanate group, a carbonate group, a carbonyl group, a carboxyl group, a sulfonyl group, and a phosphoryl group, which may be substituted with a halogen atom.

Out of the compounds represented by formula (1), a compound where in the formula, L is any one organic group selected form the group consisting of an alkyl group, an alkylene group, an alkenyl group, an alkenylene group, an alkynyl group and an alkynylene group, each having a carbon number of 1 to 8, which may have a substituent, and R is an alkenyl group having a carbon number of 2 to 8, which may have a substituent, is preferred.

However, a case where R is a vinyl group and L is an alkyl group and a case where R and L are an allyl group are excluded.

Out of the compounds represented by formula (1), a compound where in the formula (1), L is any one organic group selected form the group consisting of an alkylene group, an alkenyl group, an alkenylene group, an alkynyl group and an alkynylene group, which may have a substituent, and R is any one group selected from the group consisting of a vinyl group, an allyl group and a propargyl group, which may have a substituent, is more preferred.

However, a case where R and L are an allyl group is excluded, and more preferably, a case where L is an allyl group is excluded.

Out of the compounds represented by formula (1), a compound where in the formula, L is any one organic group selected form the group consisting of an alkylene group, a vinyl group, an alkenylene group, an alkynyl group and an alkynylene group, which may have a substituent, and R is any one group selected from the group consisting of a vinyl group, an allyl group and a propargyl group, which may have a substituent, is most preferred.

The molecular weight of the sulfonic acid ester represented by formula (1) is not particularly limited and may be arbitrary as long as the effects of the present invention are not seriously impaired. The molecular weight is preferably from 100 or more, more preferably 130 or more, still more preferably 145 or more, and is 500 or less, preferably 300 or less, more preferably 270 or less. Within this range, it is easy to ensure the solubility of the sulfonic acid ester for a nonaqueous electrolyte solution and bring out the effects of the present invention.

Specific examples of the sulfonic acid ester represented by formula (1) include the following compounds.

[Chem. 5]

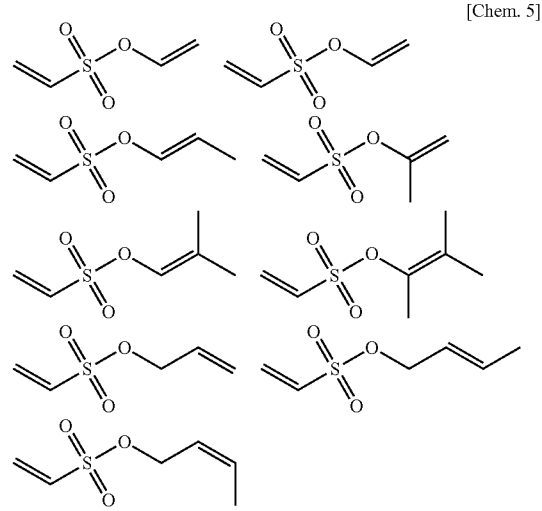

[Chem. 6]

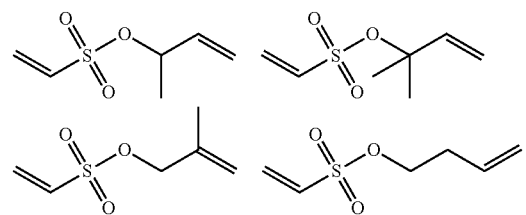

-continued
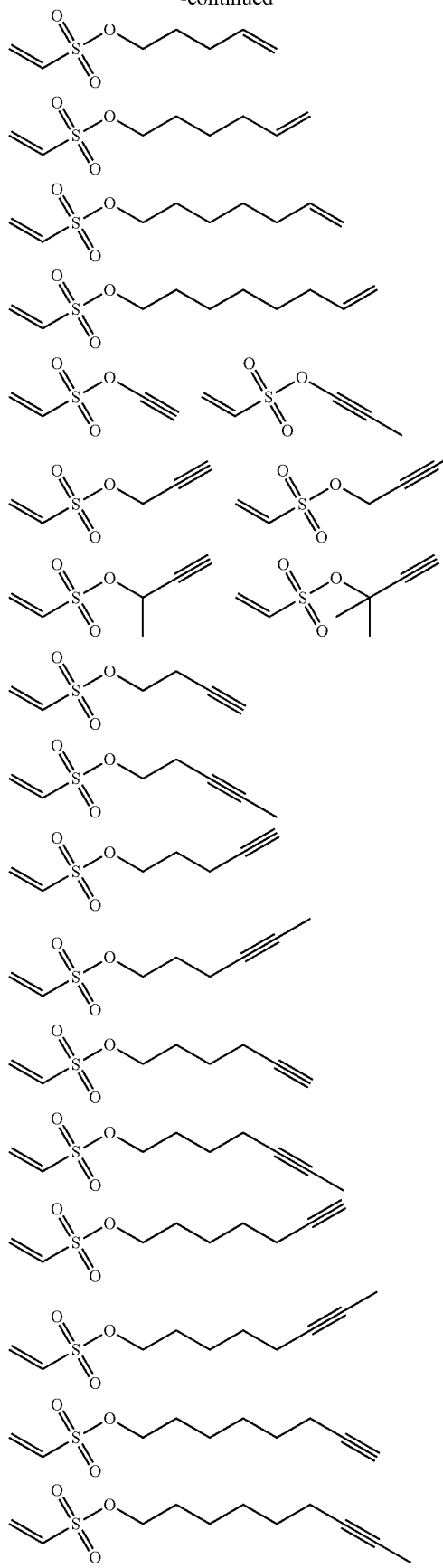
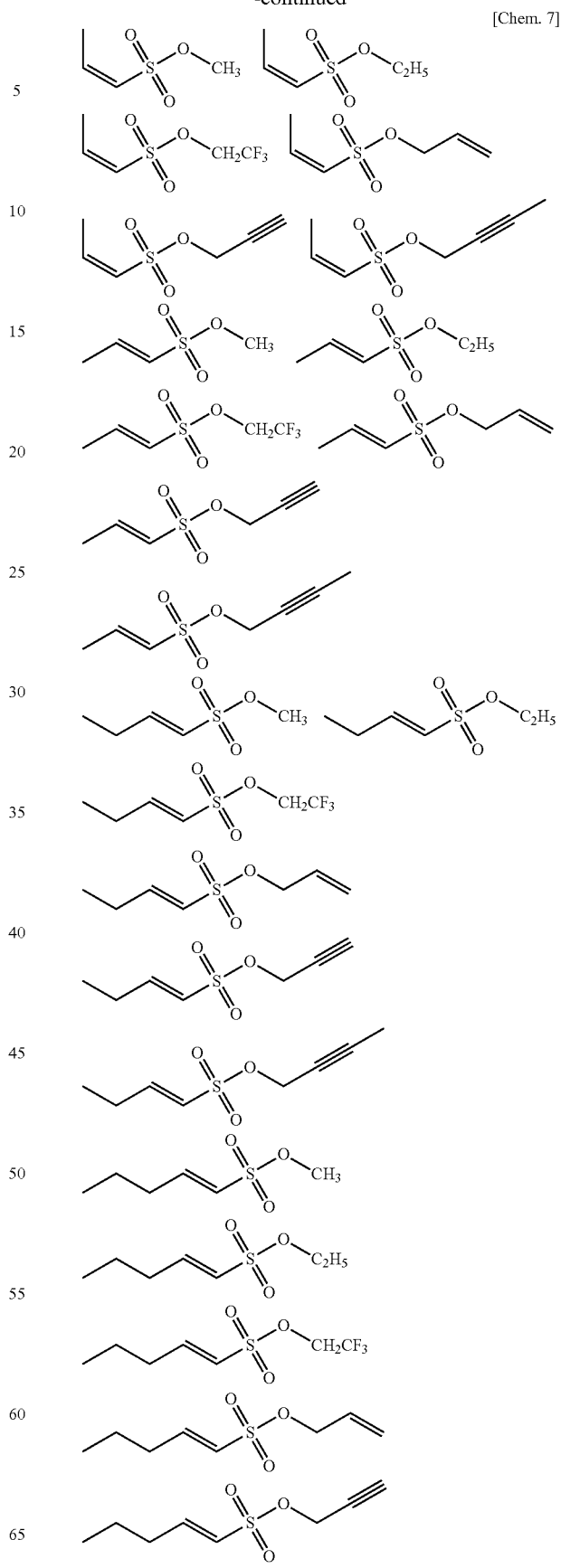

-continued
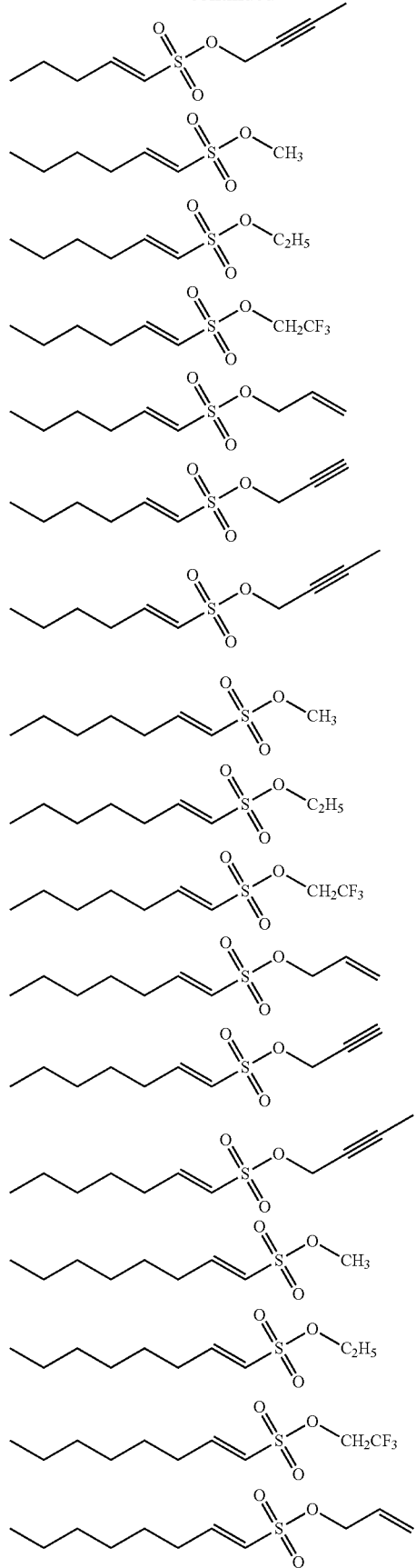
[Chem. 8]
-continued
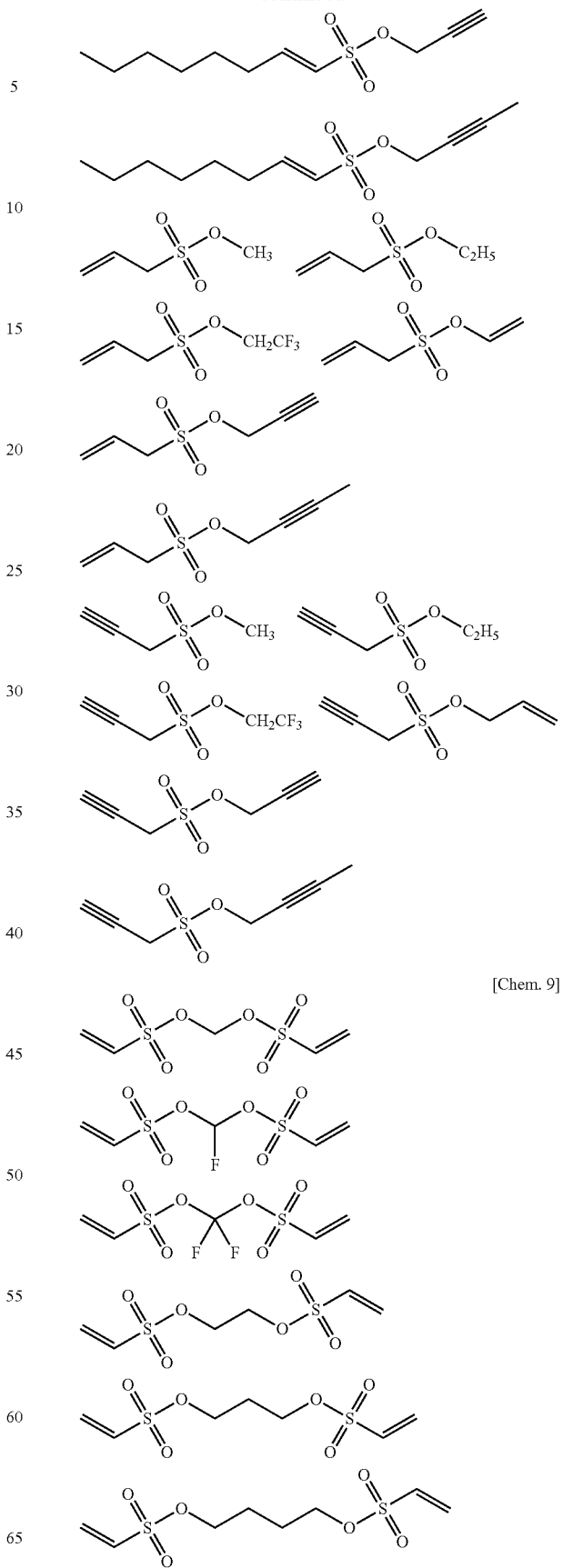
[Chem. 9]

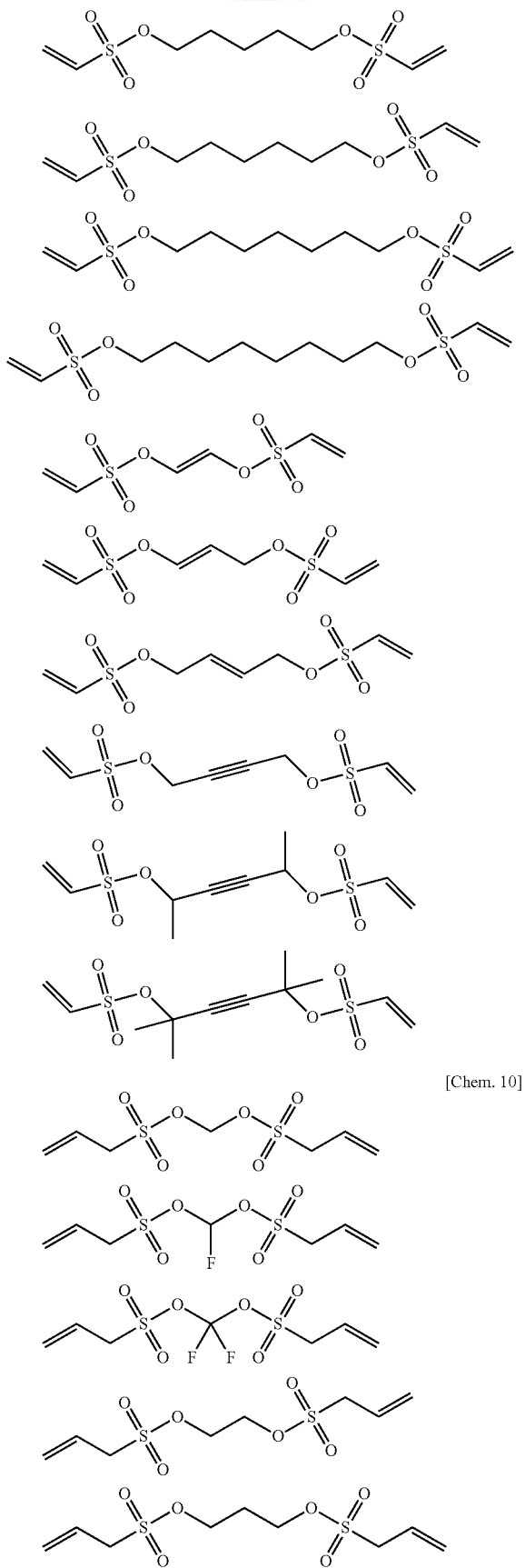
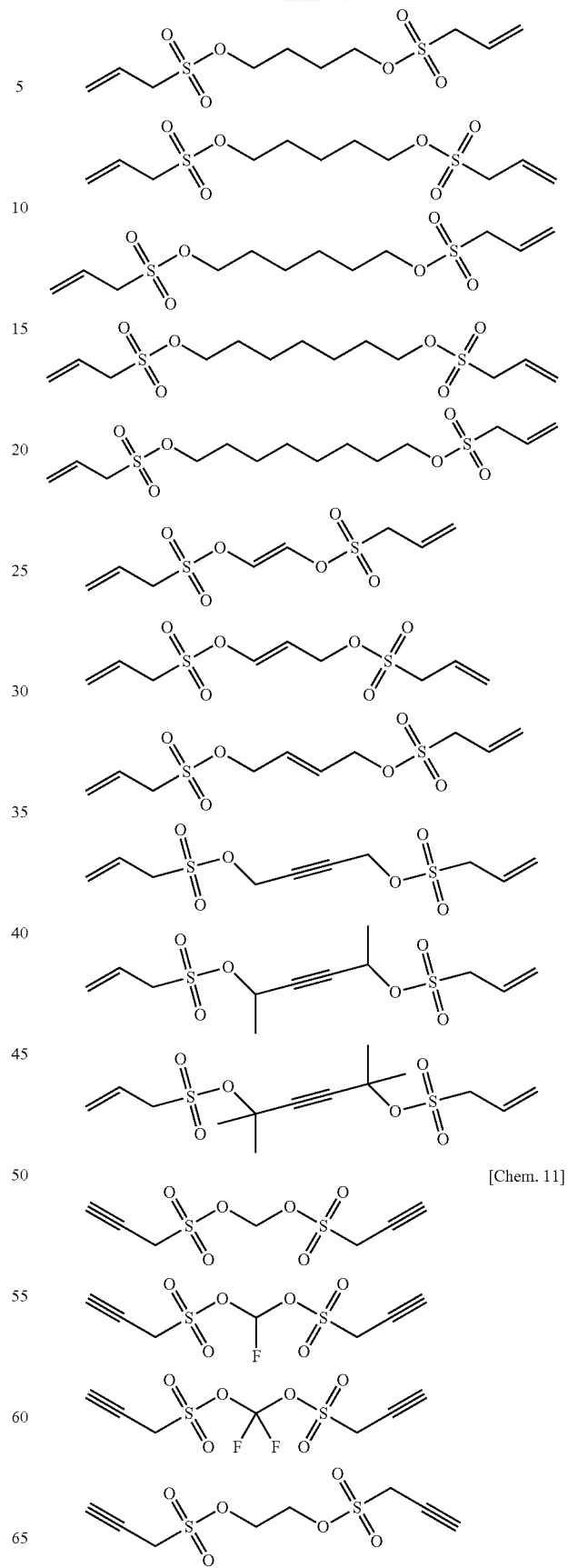
[Chem. 10]
[Chem. 11]

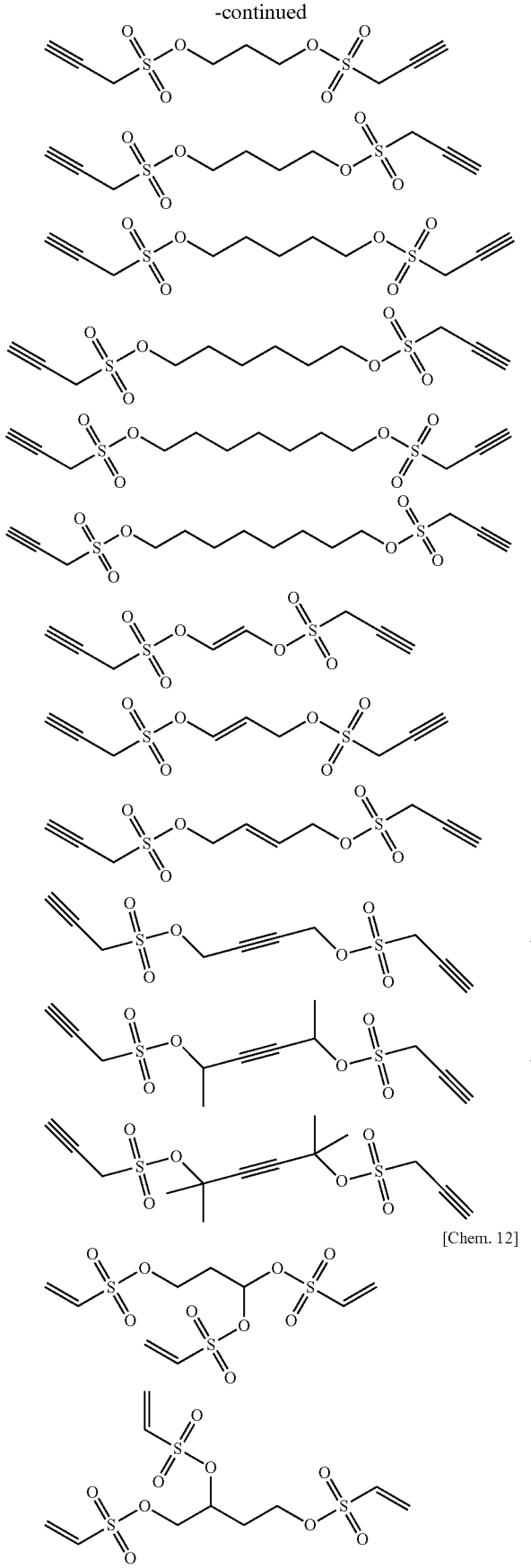
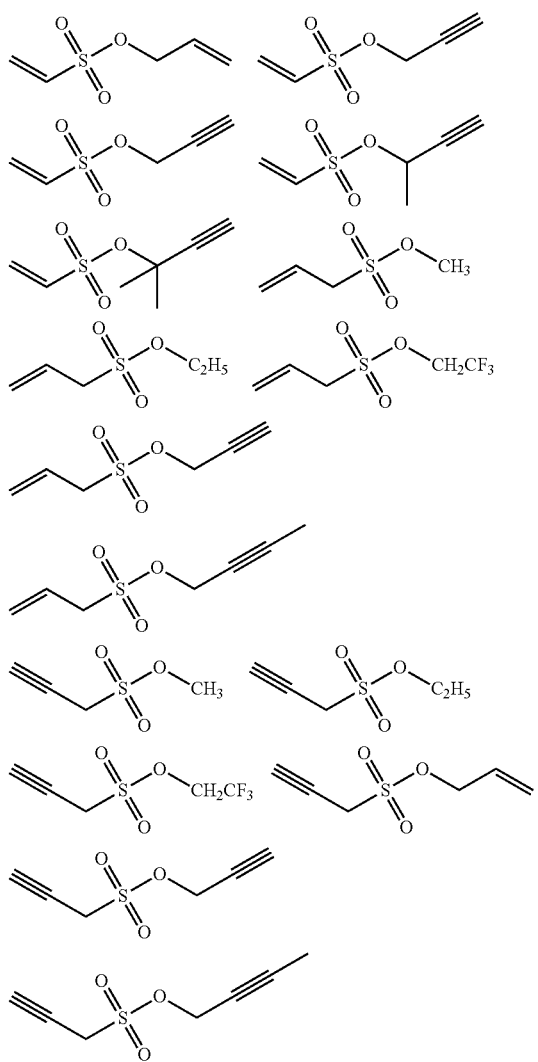
Among these compounds, preferred are:

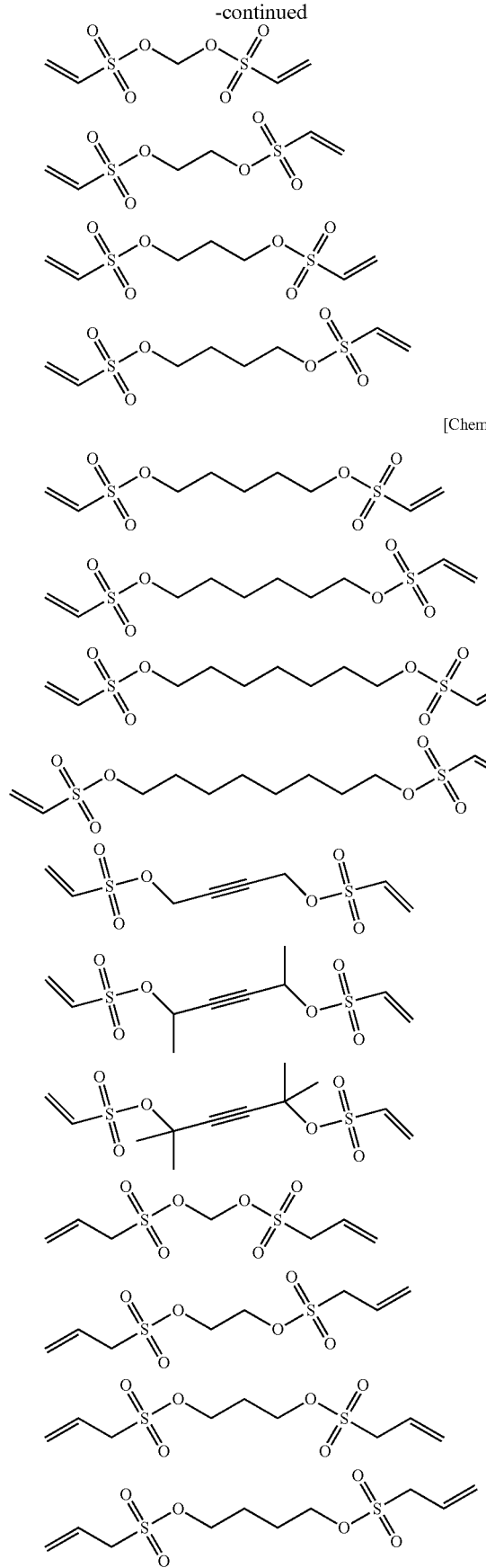
[Chem. 14]
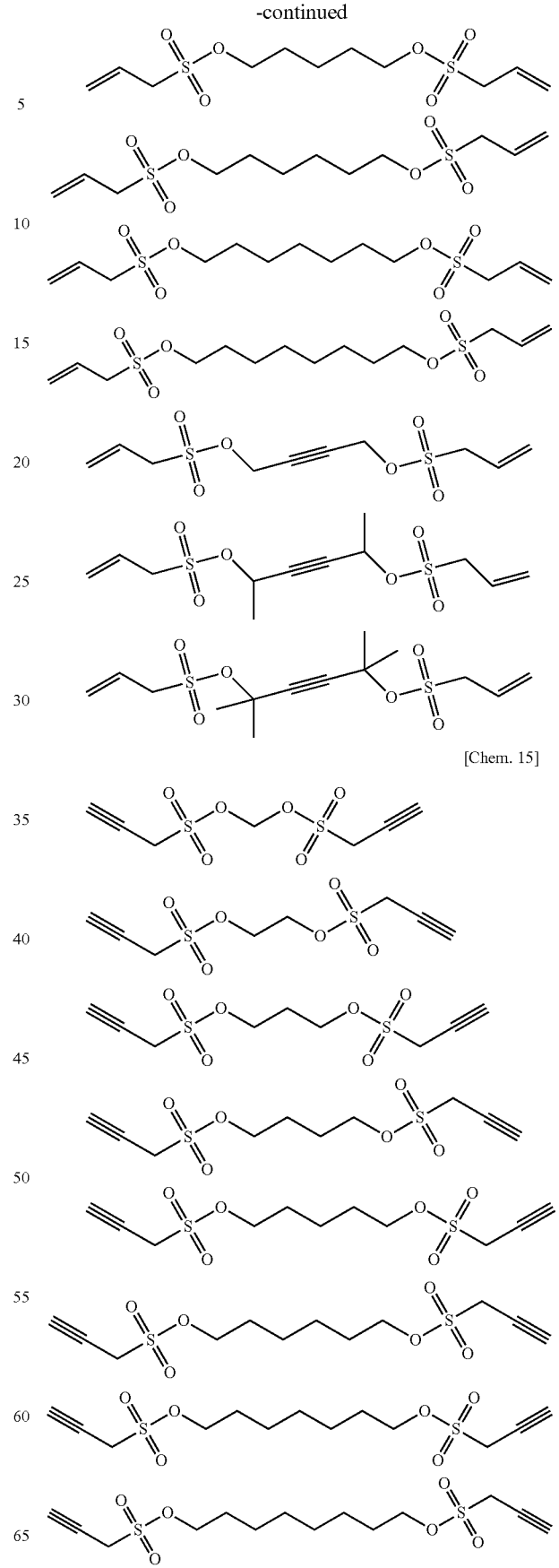
[Chem. 15]

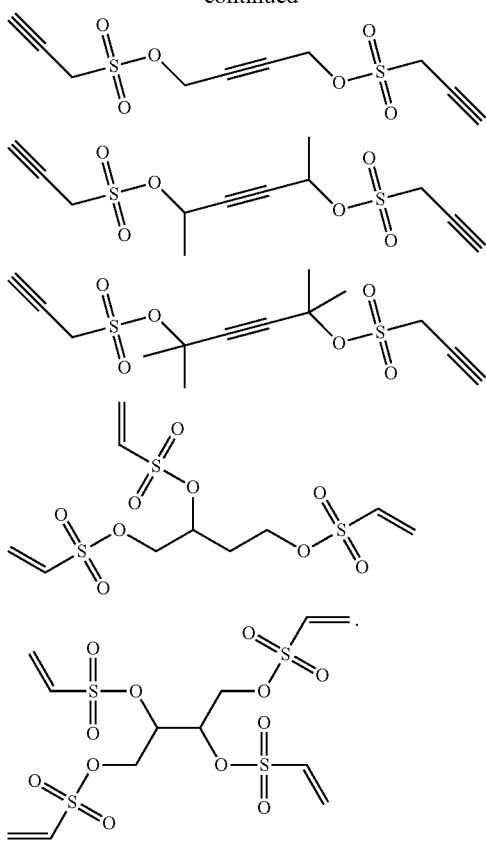

because such a sulfonic acid ester forms, on an electrode, a composite film with at least one compound selected from the group consisting of a fluorine atom-containing cyclic carbonate, a carbon-carbon unsaturated bond-containing cyclic carbonate, a monofluorophosphate, a difluorophosphate, an isocyanate compound and a cyclic sulfonic acid ester and thereby can enhance storage characteristics and cycle characteristics. Also, sulfonic acid esters such as:

[Chem. 16]

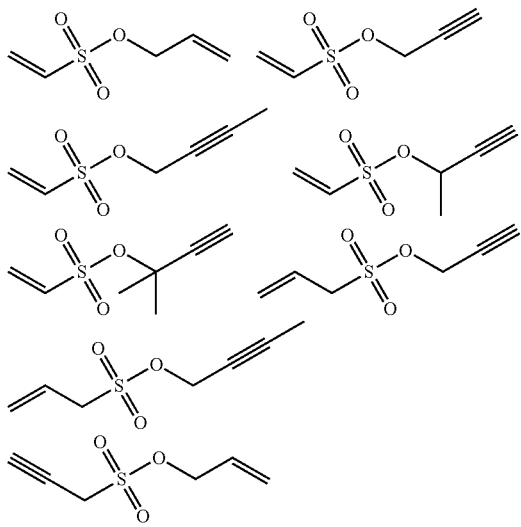

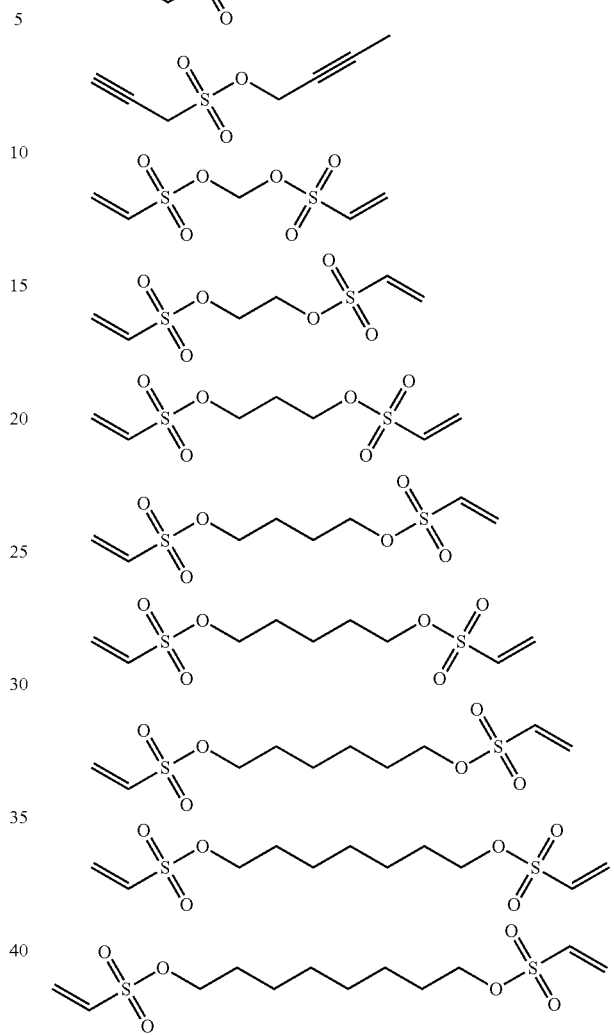

[Chem. 17]

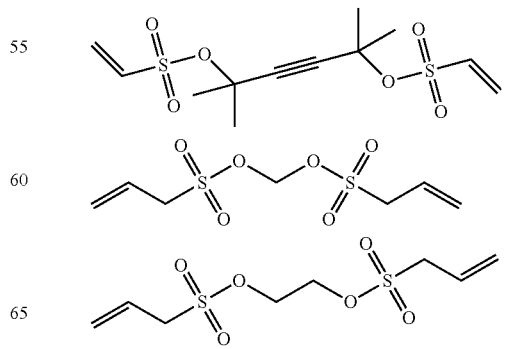

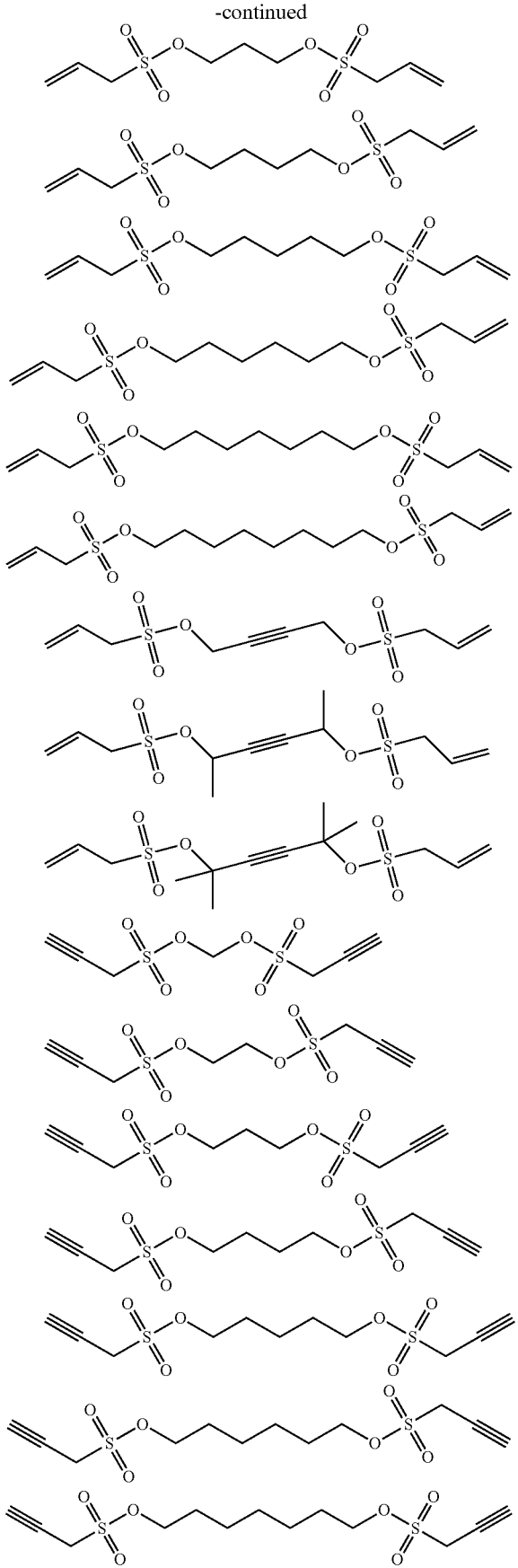
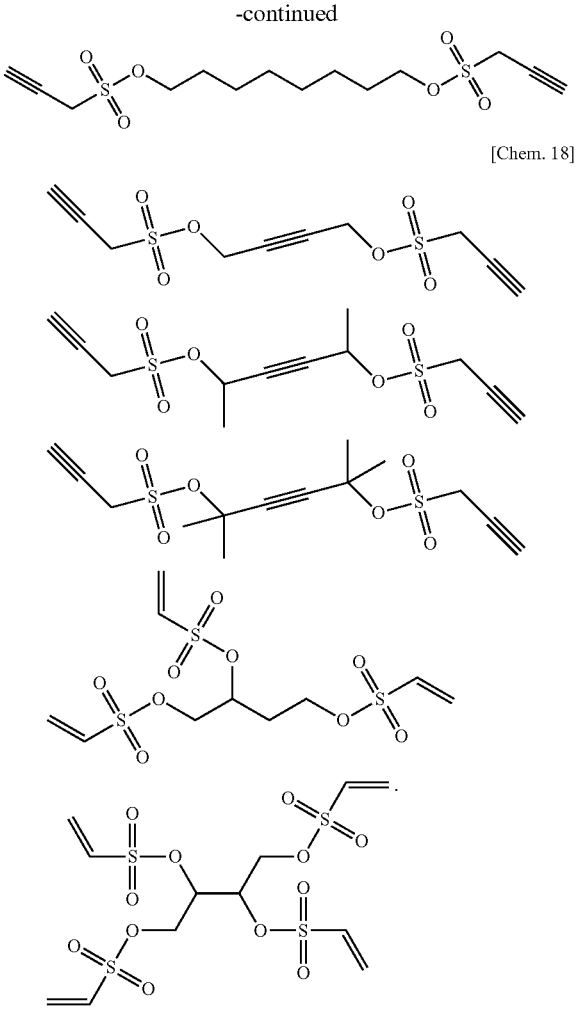
have a plurality of unsaturated bonds per molecule, so that such a sulfonic acid ester by itself can form, on an electrode, a film excellent in storage characteristics and cycle characteristics and in turn, the effects can be obtained by the addition of the sulfonic acid ester alone.
Furthermore, sulfonic acid esters such as:
[Chem. 19]
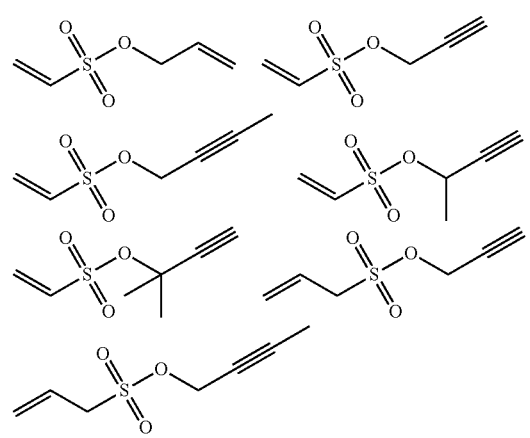

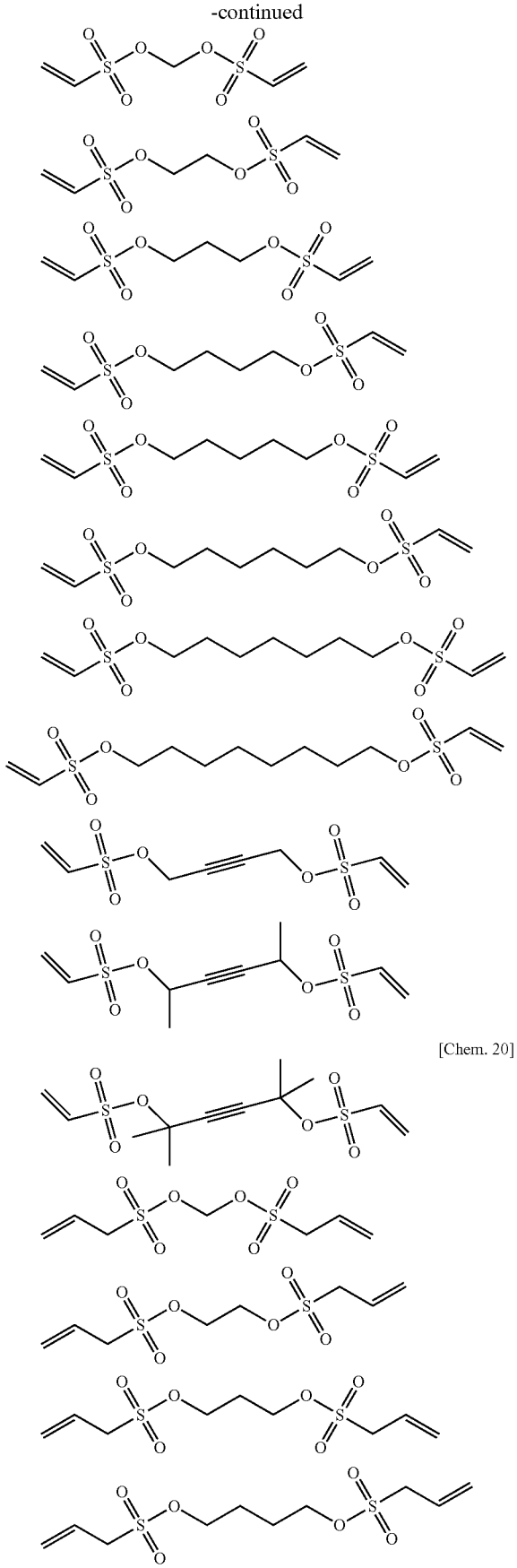
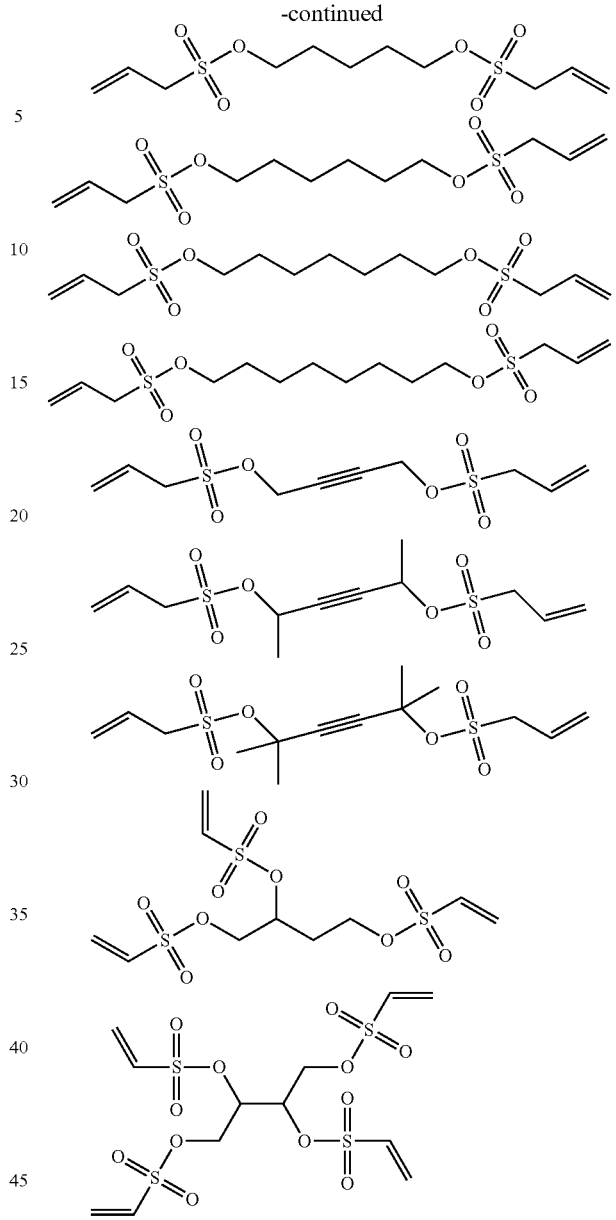

are particularly preferred, because these sulfonic acid esters have a plurality of double bonds per molecule, making it possible to form a crosslinked film that is stable and causes little increase in the resistance, and the battery is excellent in storage characteristics and cycle characteristics.

As for the sulfonic acid ester represented by formula (1), one kind may be used alone, or two or more kinds may be used together in any combination in an arbitrary ratio. The blending amount of the sulfonic acid ester based on the entire nonaqueous electrolyte solution of the present invention is not limited and may be arbitrary as long as the effects of the present invention are not seriously impaired, but the sulfonic acid ester is incorporated into the nonaqueous electrolyte solution of the present invention at a concentration of usually 0.001 mass % or more, preferably 0.01 mass % or more, more preferably 0.1 mass % or more, and usually 10 mass % or less, preferably 5 mass % or less, more preferably 3 mass % or less. When the ranges above are satisfied, the effects in terms of output characteristics, load characteristics, low-temperature characteristics, cycle characteristics, high-temperature storage characteristics and the like are more enhanced.

In the case where R is a vinyl group and L is an alkyl group, an elimination reaction in the L moiety and a gasification reaction are likely to occur when the compound is subject to a reduction reaction on the negative electrode. This gives rise to an increase in the amount of gas evolved during storage and a worsening of the battery characteristics after storage. In the case where R is an allyl group or a propyl group, the reduction reaction on the negative electrode is weak as compared with the case of a vinyl group and therefore, an elimination reaction does not proceed so much.

In the case where R and L are an allyl group, two allyl groups with poor oxidation resistance are present in the molecule and the size of the entire molecule is small. Therefore, an oxidation decomposition reaction readily proceeds on the positive electrode and in turn, the battery capacity after storage is reduced.

1-2. Fluorine Atom-Containing Cyclic Carbonate, Carbon-Carbon Unsaturated Bond-Containing Cyclic Carbonate, Monofluorophosphate, Difluorophosphate, Isocyanate Compound, Cyclic Sulfonic Acid Ester and Nitrile Compound The nonaqueous electrolyte solution according to the present invention preferably further contains at least one compound selected from the group consisting of a fluorine atom-containing cyclic carbonate, a carbon-carbon unsaturated bond-containing cyclic carbonate, a monofluorophosphate, a difluorophosphate, an isocyanate compound, a cyclic sulfonic acid ester and a nitrile compound. Because, by using such a compound in combination, a side reaction caused by each additive can be efficiently suppressed.

A fluorine atom-containing cyclic carbonate, a carbon-carbon unsaturated bond-containing cyclic carbonate and a cyclic sulfonic acid ester are more preferred, because each of these compounds forms a stable protective film on the negative electrode surface in cooperation with the sulfonic acid ester represented by formula (1) and thereby can suppress a side reaction of the negative electrode with the electrolyte solution and enhance high-temperature storage characteristics and cycle characteristics.

<Fluorine Atom-Containing Cyclic Carbonate>

The fluorine atom-containing cyclic carbonate (hereinafter, sometimes referred to as "fluorinated cyclic carbonate") is not particularly limited as long as it is a cyclic carbonate having a fluorine atom.

The fluorinated cyclic carbonate includes a fluorination product of a cyclic carbonate having an alkylene group with a carbon number of 2 to 6, and a derivative thereof, and examples thereof include a fluorination product of an ethylene carbonate, and a derivative thereof. The derivative of a fluorination product of an ethylene carbonate includes, for example, a fluorination product of an ethylene carbonate substituted with an alkyl group (for example, an alkyl group having a carbon number of 1 to 4). Above all, an ethylene carbonate having from 1 to 8 fluorine atoms and a derivative thereof are preferred.

Specific examples thereof include monofluoroethylene carbonate, 4,4-difluoroethylene carbonate, 4,5-difluoroethylene carbonate, 4-fluoro-4-methylethylene carbonate, 4,5-difluoro-4-methylethylene carbonate, 4-fluoro-5-methylethylene carbonate, 4,4-difluoro-5-methylethylene carbonate, 4-(fluoromethyl)-ethylene carbonate, 4-(difluoromethyl)-ethylene carbonate, 4-(trifluoromethyl)-ethylene carbonate, 4-(fluoromethyl)-4-fluoroethylene carbonate, 4-(fluoromethyl)-5-fluoroethylene carbonate, 4-fluoro-4,5-dimethylethylene carbonate, 4,5-difluoro-4,5-dimethylethylene carbonate, and 4,4-difluoro-5,5-dimethylethylene carbonate.

Among others, at least one member selected from the group consisting of monofluoroethylene carbonate, 4,4-difluoroethylene carbonate and 4,5-difluoroethylene carbonate is preferred in terms of imparting high ionic conductivity and appropriately forming an interface protective film.

As for the fluorinated cyclic carbonate, one kind may be used alone, or two or more kinds may be used together in any combination in an arbitrary ratio.

The content of the fluorinated cyclic carbonate is preferably 0.1 mass % or more, more preferably 0.5 mass % or more, still more preferably 1 mass % or more, and preferably 10 mass % or less, more preferably 5 mass % or less, still more preferably 3 mass % or less, based on the nonaqueous electrolyte solution. Also, in the case of using the fluorinated cyclic carbonate as a nonaqueous solvent, the blending amount thereof is preferably 1 vol % or more, more preferably 5 vol % or more, still more preferably 10 vol % or more, and preferably 50 vol % or less, more preferably 35 vol % or less, still more preferably 25 vol % or less, per 100 vol % of the nonaqueous solvent.

Within these ranges, it is easy for the nonaqueous electrolyte secondary battery to exert a sufficient enhancing effect on cycle characteristics and avoid reduction in high-temperature storage characteristics or prevent the discharge capacity retention ratio from decreasing due to an increase in the amount of gas evolved.

In the nonaqueous electrolyte solution of the present invention, the sulfonic acid ester represented by formula (1) and the fluorine atom-containing cyclic carbonate form a composite film on the negative electrode. From the standpoint of successfully forming such a film, the blending ratio by mass between the compound represented by formula (1) and the fluorinated cyclic carbonate is preferably from 0.4:100 to 100:100, more preferably from 1:100 to 50:100, still more preferably from 1.4:100 to 35:100. When blended within this range, a side reaction of each additive on positive or negative electrode can be efficiently suppressed, and the battery characteristics are enhanced, <Carbon-Carbon Unsaturated Bond-Containing Cyclic Carbonate>

The carbon-carbon unsaturated bond-containing cyclic carbonate (hereinafter, sometimes referred to as "unsaturated cyclic carbonate") is not particularly limited as long as it is a cyclic carbonate having a carbon-carbon double bond or a carbon-carbon triple bond, and an arbitrary unsaturated carbonate can be used. Incidentally, a cyclic carbonate having an aromatic ring is also encompassed by the unsaturated cyclic carbonate.

Examples of the unsaturated cyclic carbonate include:
vinylene carbonates, ethylene carbonates substituted with an aromatic ring or a substituent having a carbon-carbon double bond or a carbon-carbon triple bond, phenyl carbonates, vinyl carbonates, allyl carbonates, and catechol carbonates.

Examples of vinylene carbonates include:
vinylene carbonate, methylvinylene carbonate, 4,5-dimethylvinylene carbonate, phenylvinylene carbonate, 4,5-diphenylvinylene carbonate, vinylvinylene carbonate, 4,5-divinylvinylene carbonate, allylvinylene carbonate, 4,5-diallylvinylene carbonate, 4-fluorovinylene carbonate, 4-fluoro-5-methylvinylene carbonate, 4-fluoro-5-phenylvinylene carbonate, 4-fluoro-5-vinylvinylene carbonate, and 4-allyl-5-fluorovinylene carbonate.

Specific examples of ethylene carbonates substituted with an aromatic ring or a substituent having a carbon-carbon double bond or a carbon-carbon triple bond include:

vinylethylene carbonate, 4,5-divinylethylene carbonate, 4-methyl-5-vinylethylene carbonate, 4-allyl-5-vinylethylene carbonate, ethynylethylene carbonate, 4,5-diethynylethylene carbonate, 4-methyl-5-ethynylethylene carbonate, 4-vinyl-5-ethynylethylene carbonate, 4-allyl-5-ethynylethylene carbonate, phenylethylene carbonate, 4,5-diphenylethylene carbonate, 4-phenyl-5-vinylethylene carbonate, 4-allyl-5-phenylethylene carbonate, allylethylene carbonate, 4,5-diallylethylene carbonate, and 4-methyl-5-allylethylene carbonate.

Among these, unsaturated cyclic carbonates preferred for use in combination with the sulfonic acid ester represented by formula (1) include:

vinylene carbonate, methylvinylene carbonate, 4,5-dimethylvinylene carbonate, vinylvinylene carbonate, 4,5-vinylvinylene carbonate, allylvinylene carbonate, 4,5-diallylvinylene carbonate, vinylethylene carbonate, 4,5-divinylethylene carbonate, 4-methyl-5-vinylethylene carbonate, allylethylene carbonate, 4,5-diallylethylene carbonate, 4-methyl-5-allylethylene carbonate, 4-allyl-5-vinylethylene carbonate, ethynylethylene carbonate, 4,5-diethynylethylene carbonate, 4-methyl-5-ethynylethylene carbonate, and 4-vinyl-5-ethynylethylene carbonate.

In particular, vinylene carbonate, vinylethylene carbonate and ethynylethylene carbonate are more preferred, because a further stable interface protective film is formed.

The molecular weight of the unsaturated cyclic carbonate is not particularly limited and may be arbitrary as long as the effects of the present invention are not seriously impaired. The molecular weight is preferably from 80 to 250. Within this range, it is easy to ensure the solubility of the unsaturated cyclic carbonate for the nonaqueous electrolyte solution and sufficiently bring out the effects of the present invention. The molecular weight of the unsaturated cyclic carbonate is more preferably 85 or more, and more preferably 150 or less.

The unsaturated cyclic carbonate is not particularly limited in its production method and can be produced by arbitrarily selecting a known method.

As for the unsaturated cyclic carbonate, one kind may be used alone, or two or more kinds may be used together in any combination in an arbitrary ratio. Also, the blending amount of the unsaturated cyclic carbonate is not particularly limited and may be arbitrary as long as the effects of the present invention are not seriously impaired. The blending amount of the unsaturated cyclic carbonate is preferably 0.001 mass % or more, more preferably 0.01 mass % or more, still more preferably 0.1 mass % or more, and preferably 5 mass % or less, more preferably 4 mass % or less, still more preferably 3 mass % or less, per 100 mass % of the nonaqueous electrolyte solution. Within these ranges, it is easy for the nonaqueous electrolyte battery to exert a sufficient enhancing effect on cycle characteristics and avoid a trouble that high-temperature storage characteristics are reduced or the amount of gas evolved is increased to cause a decrease in the discharge capacity retention ratio.

<Monofluorophosphate and Difluorophosphate>

Counter cations of the monofluorophosphate and the difluorophosphate are not particularly limited, but examples thereof include lithium, sodium, potassium, magnesium, calcium, and ammonium represented by $NR^{11}R^{12}R^{13}R^{14}$ (wherein each of $R^{11}$ to $R^{14}$ independently represents a hydrogen atom or an organic group having a carbon number of 1 to 12).

The organic group having a carbon number of 1 to 12 represented by $R^{11}$ to $R^{14}$ in the ammonium above is not particularly limited, but examples thereof include an alkyl group which may be substituted with a halogen atom, a cycloalkyl group which may be substituted with a halogen atom or an alkyl group, an aryl group which may be substituted with a halogen atom or an alkyl group, and a nitrogen atom-containing heterocyclic group which may have a substituent. Among others, each of $R^{11}$ to $R^{14}$ is independently, preferably a hydrogen atom, an alkyl group, a cycloalkyl group or a nitrogen atom-containing heterocyclic group.

Specific examples of the monofluorophosphate and difluorophosphate include:

lithium monofluorophosphate, sodium monofluorophosphate, potassium monofluorophosphate, lithium difluorophosphate, sodium difluorophosphate, and potassium difluorophosphate.

Lithium monofluorophosphate and lithium difluorophosphate are preferred, and lithium difluorophosphate is more preferred.

As for the monofluorophosphate and difluorophosphate, one kind may be used alone, or two or more kinds may be used together in any combination in an arbitrary ratio. The blending amount of each of the monofluorophosphate and the difluorophosphate is not particularly limited and may be arbitrary as long as the effects of the present invention are not seriously impaired.

The blending amount of each of the monofluorophosphate and the difluorophosphate is preferably 0.001 mass % or more, more preferably 0.01 mass % or more, still more preferably 0.1 mass % or more, and preferably 5 mass % or less, more preferably 4 mass % or less, still more preferably 3 mass % or less, per 100 mass % of the nonaqueous electrolyte solution.

Within these ranges, it is easy for the nonaqueous electrolyte battery to exert a sufficient enhancing effect on cycle characteristics and avoid a trouble that high-temperature storage characteristics are reduced or the amount of gas evolved is increased to cause a decrease in the discharge capacity retention ratio.

<Isocyanate Compound>

The isocyanate compound is not particularly limited in its kind as long as it is a compound having an isocyanate group in the molecule.

Specific examples of the isocyanate compound include:

a monoisocyanate compound such as methyl isocyanate, ethyl isocyanate, propyl isocyanate, isopropyl isocyanate, butyl isocyanate, tertiary-butyl isocyanate, pentyl isocyanate, hexyl isocyanate, cyclohexyl isocyanate, vinyl isocyanate, allyl isocyanate, ethynyl isocyanate, propynyl isocyanate, phenyl isocyanate, and fluorophenyl isocyanate; and a diisocyanate compound such as monomethylene diisocyanate, dimethylene diisocyanate, trimethylene diisocyanate, tetramethylene diisocyanate, pentamethylene diisocyanate, hexamethylene diisocyanate, heptamethylene diisocyanate, octamethylene diisocyanate, nonamethylene diisocyanate, decamethylene diisocyanate, 1,3-diisocyanatopropane, 1,4-diisocyanato-2-butene, 1,4-diisocyanato-2-fluorobutane, 1,4-diisocyanato-2,3-difluorobutane, 1,5-diisocyanato-2-pentene, 1,5-diisocyanato-2-methylpentane, 1,6-diisocyanato-2-hexene, 1,6-diisocyanato-3-hexene, 1,6-diisocyanato-3-fluorohexane, 1,6-diisocyanato-3,4-difluorohexane, toluene diisocyanate, xylene diisocyanate, tolylene diisocyanate, 1,2-bis(isocyanatomethyl)cyclohexane, 1,3-bis(isocyanatomethyl)cyclohexane, 1,4-bis(isocyanatomethyl)cyclohexane, 1,2-diisocyanatocyclohexane, 1,3-diisocyanatocyclohexane, 1,4-diisocyanatocyclohexane, dicyclohexylmethane-1,1'-diisocyanate, dicyclohexylmethane-2,2'-diisocyanate, dicyclohexylmethane-3,3'-diisocyanate, dicyclohexylmethane-4,4'-diisocyanate and isophorone diisocyanate.

Among these, from the standpoint of enhancing storage characteristics, dimethylene diisocyanate, tetramethylene diisocyanate, hexamethylene diisocyanate, octamethylene diisocyanate, decamethylene diisocyanate, 1,3-bis(isocyanatomethyl)cyclohexane and dicyclohexylmethane-4,4'-diisocyanate are preferred.

As for the compound having an isocyanate group, one compound may be used alone, or two or more compounds may be used together in any combination in an arbitrary ratio.

The blending amount of the isocyanate group-containing compound based on the entire nonaqueous electrolyte solution of the present invention is not limited and may be arbitrary as long as the effects of the present invention are not seriously impaired, but the compound is incorporated into the nonaqueous electrolyte solution of the present invention at a concentration of usually 0.001 mass % or more, preferably 0.1 mass % or more, more preferably 0.3 mass % or more, and usually 10 mass % or less, preferably 5 mass % or less, more preferably 3 mass % or less.

When the ranges above are satisfied, the effects in terms of output characteristics, load characteristics, low-temperature characteristics, cycle characteristics, high-temperature storage characteristics and the like are more enhanced.

<Cyclic Sulfonic Acid Ester>

The cyclic sulfonic acid ester is not particularly limited in its kind as long as it is a sulfonic acid ester having a cyclic structure.

Specific examples of the cyclic sulfonic acid ester include:

a sultone compound such as 1,3-propanesultone, 1-fluoro-1,3-propanesultone, 2-fluoro-1,3-propanesultone, 3-fluoro-1,3-propanesultone, 1-methyl-1,3,-propanesultone, 2-methyl-1,3-propanesultone, 3-methyl-1,3-propanesultone, 1-propene-1,3-sultone, 2-propene-1,3-sultone, 1-fluoro-1-propene-1,3-sultone, 2-fluoro-1-propene-1,3-sultone, 3-fluoro-1-propene-1,3-sultone, 1-fluoro-2-propene-1,3-sultone, 2-fluoro-2-propene-1,3-sultone, 3-fluoro-2-propene-1,3-sultone, 1-methyl-1-propene-1,3-sultone, 2-methyl-1-propene-1,3-sultone, 3-methyl-1-propene-1,3-sultone, 1-methyl-2-propene-1,3-sultone, 2-methyl-2-propene-1,3-sultone, 3-methyl-2-propene-1,3-sultone, 1,4-butanesultone, 1-fluoro-1,4-butanesultone, 2-fluoro-1,4-butanesultone, 3-fluoro-1,4-butanesultone, 4-fluoro-1,4-butanesultone, 1-methyl-1,4-butanesultone, 2-methyl-1,4-butanesultone, 3-methyl-1,4-butanesultone, 4-methyl-1,4-butanesultone, 1-butene-1,4-sultone, 2-butene-1,4-sultone, 3-butene-1,4-sultone, 1-fluoro-1-butene-1,4-sultone, 2-fluoro-1-butene-1,4-sultone, 3-fluoro-1-butene-1,4-sultone, 4-fluoro-1-butene-1,4-sultone, 1-fluoro-2-butene-1,4-sultone, 2-fluoro-2-butene-1,4-sultone, 3-fluoro-2-butene-1,4-sultone, 4-fluoro-2-butene-1,4-sultone, 1-fluoro-3-butene-1,4-sultone, 2-fluoro-3-butene-1,4-sultone, 3-fluoro-3-butene-1,4-sultone, 4-fluoro-3-butene-1,4-sultone, 1-methyl-1-butene-1,4-sultone, 2-methyl-1-butene-1,4-sultone, 3-methyl-1-butene-1,4-sultone, 4-methyl-1-butene-1,4-sultone, 1-methyl-2-butene-1,4-sultone, 2-methyl-2-butene-1,4-sultone, 3-methyl-2-butene-1,4-sultone, 4-methyl-2-butene-1,4-sultone, 1-methyl-3-butene-1,4-sultone, 2-methyl-3-butene-1,4-sultone, 3-methyl-3-butene-1,4-sultone, 4-methyl-3-butene-1,4-sultone, 1,5-pentanesultone, 1-fluoro-1,5-pentanesultone, 2-fluoro-1,5-pentanesultone, 3-fluoro-1,5-pentanesultone, 4-fluoro-1,5-pentanesultone, 5-fluoro-1,5-pentanesultone, 1-methyl-1,5-pentanesultone, 2-methyl-1,5-pentanesultone, 3-methyl-1,5-pentanesultone, 4-methyl-1,5-pentanesultone, 5-methyl-1,5-pentanesultone, 1-pentene-1,5-sultone, 2-pentene-1,5-sultone, 3-pentene-1,5-sultone, 4-pentene-1,5-sultone, 1-fluoro-1-pentene-1,5-sultone, 2-fluoro-1-pentene-1,5-sultone, 3-fluoro-1-pentene-1,5-sultone, 4-fluoro-1-pentene-1,5-sultone, 5-fluoro-1-pentene-1,5-sultone, 1-fluoro-2-pentene-1,5-sultone, 2-fluoro-2-pentene-1,5-sultone, 3-fluoro-2-pentene-1,5-sultone, 4-fluoro-2-pentene-1,5-sultone, 5-fluoro-2-pentene-1,5-sultone, 1-fluoro-3-pentene-1,5-sultone, 2-fluoro-3-pentene-1,5-sultone, 3-fluoro-3-pentene-1,5-sultone, 4-fluoro-3-pentene-1,5-sultone, 5-fluoro-3-pentene-1,5-sultone, 1-fluoro-4-pentene-1,5-sultone, 2-fluoro-4-pentene-1,5-sultone, 3-fluoro-4-pentene-1,5-sultone, 4-fluoro-4-pentene-1,5-sultone, 5-fluoro-4-pentene-1,5-sultone, 1-methyl-1-pentene-1,5-sultone, 2-methyl-1-pentene-1,5-sultone, 3-methyl-1-pentene-1,5-sultone, 4-methyl-1-pentene-1,5-sultone, 5-methyl-1-pentene-1,5-sultone, 1-methyl-2-pentene-1,5-sultone, 2-methyl-2-pentene-1,5-sultone, 3-methyl-2-pentene-1,5-sultone, 4-methyl-2-pentene-1,5-sultone, 5-methyl-2-pentene-1,5-sultone, 1-methyl-3-pentene-1,5-sultone, 2-methyl-3-pentene-1,5-sultone, 3-methyl-3-pentene-1,5-sultone, 4-methyl-3-pentene-1,5-sultone, 5-methyl-3-pentene-1,5-sultone, 1-methyl-4-pentene-1,5-sultone, 2-methyl-4-pentene-1,5-sultone, 3-methyl-4-pentene-1,5-sultone, 4-methyl-4-pentene-1,5-sultone and 5-methyl-4-pentene-1,5-sultone;

a sulfate compound such as methylene sulfate, ethylene sulfate and propylene sulfate;

a disulfonate compound such as methylene methanedisulfonate and ethylene methanedisulfonate;

a nitrogen-containing compound such as 1,2,3-oxathiazolidine-2,2-dioxide, 3-methyl-1,2,3-oxathiazolidine-2,2-dioxide, 3H-1,2,3-oxathiazole-2,2-dioxide, 5H-1,2,3-oxathiazole-2,2-dioxide, 1,2,4-oxathiazolidine-2,2-dioxide, 4-methyl-1,2,4-oxathiazolidine-2,2-dioxide, 3H-1,2,4-oxathiazole-2,2-dioxide, 5H-1,2,4-oxathiazole-1,2,5-oxathiazolidine-2,2-dioxide, 5-methyl-1,2,5-oxathiazolidine-2,2-dioxide, 3H-1,2,5-oxathiazole-2,2-dioxide, 5H-1,2,5-oxathiazole-2,2-dioxide, 1,2,3-oxathiazinane-2,2-dioxide, 3-methyl-1,2,3-oxathiazinane-2,2-dioxide, 5,6-dihydro-1,2,3-oxathiazine-2,2-dioxide, 1,2,4-oxathiazinane-2,2-dioxide, 4-methyl-1,2,4-oxathiazinane-2,2-dioxide, 5,6-dihydro-1,2,4-oxathiazine-2,2-dioxide, 3,6-dihydro-1,2,4-oxathiazine-2,2-dioxide, 3,4-dihydro-1,2,4-oxathiazine-2,2-dioxide, 1,2,5-oxathiazinane-2,2-dioxide, 5-methyl-1,2,5-oxathiazinane-2,2-dioxide, 5,6-dihydro-1,2,5-oxathiazine-2,2-dioxide, 3,6-dihydro-1,2,5-oxathiazine-2,2-dioxide, 3,4-dihydro-1,2,5-oxathiazine-2,2-dioxide, 1,2,6-oxathiazinane-2,2-dioxide, 6-methyl-1,2,6-oxathiazinane-2,2-dioxide, 5,6-dihydro-1,2,6-oxathiazine-2,2-dioxide, 3,4-dihydro-1,2,6-oxathiazine-2,2-dioxide and 5,6-dihydro-1,2,6-oxathiazine-2,2-dioxide; and a phosphorus-containing compound such as 1,2,3-oxathiaphoslane-2,2-dioxide, 3-methyl-1,2,3-oxathiaphoslane-2,2-dioxide, 3-methyl-1,2,3-oxathiaphoslane-2,2,3-trioxide, 3-methoxy-1,2,3-oxathiaphoslane-2,2,3-trioxide, 1,2,4-oxathiaphoslane-2,2-dioxide, 4-methyl-1,2,4-oxathiaphoslane-2,2-dioxide, 4-methyl-1,2,4-oxathiaphoslane-2,2,4-trioxide, 4-methoxy-1,2,4-oxathiaphoslane-2,2,4-trioxide, 1,2,5-oxathiaphoslane-2,2-dioxide, 5-methyl-1,2,5-oxathiaphoslane-2,2-dioxide, 5-methyl-1,2,5-oxathiaphoslane-2,2,5-trioxide, 5-methoxy-1,2,5-oxathiaphoslane-2,2,5-trioxide, 1,2,3-oxathiaphosphinane-2,2-dioxide, 3-methyl-1,2,3-oxathiaphosphinane-2,2-dioxide, 3-methyl-1,2,3-oxathiaphosphinane-2,2,3-trioxide, 3-methoxy-1,2,3-oxathiaphosphinane-2,2,3- trioxide, 1,2,4-oxathiaphosphinane-2,2-dioxide, 4-methyl-1,2,4-oxathiaphosphinane-2,2-dioxide, 4-methyl-1,2,4-oxathiaphosphinane-2,2,3-trioxide, 4-methyl-1,5,2,4-dioxathiaphosphinane-2,4-dioxide, 4-methoxy-1,5,2,4-dioxathiaphosphinane-2,4-dioxide, 3-methoxy-1,2,4-oxathiaphosphinane-2,2,3-trioxide, 1,2,5-oxathiaphosphinane-2,2-dioxide, 5-methyl-1,2,5-oxathiaphosphinane-2,2-dioxide, 5-methyl-1,2,5-oxathiaphosphinane-2,2,3-trioxide, 5-methoxy-1,2,5-oxathiaphosphinane-2,2,3-trioxide, 1,2,6-oxathiaphosphinane-2,2-dioxide, 6-methyl-1,2,6-oxathiaphosphinane-2,2-dioxide, 6-methyl-1,2,6-oxathiaphosphinane-2,2,3-trioxide, and 6-methoxy-1,2,6-oxathiaphosphinane-2,2,3-trioxide.

Among these, 1,3-propanesultone, 1-fluoro-1,3-propanesultone, 2-fluoro-1,3-propanesultone, 3-fluoro-1,3-propanesultone, 1-propene-1,3-sultone, 1-fluoro-1-propene-1,3-sultone, 2-fluoro-1-propene-1,3-sultone, 3-fluoro-1-propene-1,3-sultone, 1,4-butanesultone, methylene methanedisulfonate and ethylene methanedisulfonate are preferred from the standpoint of enhancing storage characteristics, and 1,3-propanesultone, 1-fluoro-1,3-propanesultone, 2-fluoro-1,3-propanesultone, 3-fluoro-1,3-propanesultone and 1-propene-1,3-sultone are more preferred.

As for the cyclic sulfonic acid ester, one kind may be used alone, or two or more kinds may be used in any combination in an arbitrary ratio. The blending amount of the cyclic sulfonic acid ester based on the entire nonaqueous electrolyte solution of the present invention is not limited and may be arbitrary as long as the effects of the present invention are not seriously impaired, but the ester sulfonic acid ester is incorporated into the nonaqueous electrolyte solution of the present invention at a concentration of usually 0.001 mass % or more, preferably 0.1 mass % or more, more preferably 0.3 mass % or more, and usually 10 mass % or less, preferably 5 mass % or less, more preferably 3 mass % or less. When the ranges above are satisfied, the effects in terms of output characteristics, load characteristics, low-temperature characteristics, cycle characteristics, high-temperature storage characteristics and the like are more enhanced.

<Nitrile Compound>

The nitrile compound is not limited in its kind as long as it is a compound having a nitrile group in the molecule.

Specific examples of the nitrile compound include:

a compound having one nitrile group, such as acetonitrile, propionitrile, butyronitrile, isobutyronitrile, valeronitrile, isovaleronitrile, lauronitrile, 2-methylbutyronitrile, trimethylacetonitrile, hexanenitrile, cyclopentanecarbonitrile, cyclohexanecarbonitrile, acrylonitrile, methacrylonitrile, crotononitrile, 3-methylcrotononitrile, 2-methyl-2-butenenitrile, 2-pentenenitrile, 2-methyl-2-pentenenitrile, 3-methyl-2-pentenenitrile, 2-hexenenitrile, fluoroacetonitrile, difluoroacetonitrile, trifluoroacetonitrile, 2-fluoropropionitrile, 3-fluoropropionitrile, 2,2-difluoropropionitrile, 2,3-difluoropropionitrile, 3,3-difluoropropionitrile, 2,2,3-trifluoropropionitrile, 3,3,3-trifluoropropionitrile, 3,3'-oxydipropionitrile, 3,3'-thiodipropionitrile, 1,2,3-propanetricarbonitrile, 1,3,5-pentanetricarbonitrile and pentafluoropropionitrile; and a compound having two nitrile groups, such as malononitrile, succinonitrile, glutaronitrile, adiponitrile, pimelonitrile, suberonitrile, azelanitrile, sebaconitrile, undecanedinitrile, dodecanedinitrile, methylmalononitrile, ethylmalononitrile, isopropylmalononitrile, tert-butylmalononitrile, methylsuccinonitrile, 2,2-dimethylsuccinonitrile, 2,3-dimethylsuccinonitrile, 2,3,3-trimethylsuccinonitrile, 2,2,3,3-tetramethylsuccinonitrile, 2,3-diethyl-2,3-dimethylsuccinonitrile, 2,2-diethyl-3,3-dimethylsuccinonitrile, bicyclohexyl-1,1-dicarbonitrile, bicyclohexyl-2,2-dicarbonitrile, bicyclohexyl-3,3-dicarbonitrile, 2,5-dimethyl-2,5-hexanedicarbonitrile, 2,3-diisobutyl-2,3-dimethylsuccinonitrile, 2,2-diisobutyl-3,3-dimethylsuccinonitrile, 2-methylglutaronitrile, 2,3-dimethylglutaronitrile, 2,4-dimethylglutaronitrile, 2,2,3,3-tetramethylglutaronitrile, 2,2,4,4-tetramethylglutaronitrile, 2,2,3,4-tetramethylglutaronitrile, 2,3,3,4-tetramethylglutaronitrile, maleonitrile, fumaronitrile, 1,4-dicyanopentane, 2,6-dicyanoheptane, 2,7-dicyanooctane, 2,8-dicyanononane, 1,6-dicyanodecane, 1,2-dicyanobenzene, 1,3-dicyanobenzene, 1,4-dicyanobenzene, 3,3'-(ethylenedioxy)dipropionitrile and 3,3'-(ethylenedithio)dipropionitrile.

Among these, lauronitrile, crotononitrile, succinonitrile, glutaronitrile, adiponitrile, pimelonitrile, suberonitrile, azelanitrile, sebaconitrile, undecanedinitrile, dodecanedinitrile and fumaronitrile are preferred from the standpoint of enhancing storage characteristics.

As for the nitrile compound, one compound may be used alone, or two or more compounds may be used together in any combination in an arbitrary ratio. The blending amount of the nitrile compound based on the entire nonaqueous electrolyte solution of the present invention is not limited and may be arbitrary as long as the effects of the present invention are not seriously impaired, but the nitrile compound is incorporated into the nonaqueous electrolyte solution of the present invention at a concentration of usually 0.001 mass % or more, preferably 0.1 mass % or more, more preferably 0.3 mass % or more, and usually 10 mass % or less, preferably 5 mass % or less, more preferably 3 mass % or less. When the ranges above are satisfied, the effects in terms of output characteristics, load characteristics, low-temperature characteristics, cycle characteristics, high-temperature storage characteristics and the like are more enhanced.

1-3. Electrolyte

<Lithium Salt>

The electrolyte usually used is a lithium salt. A lithium salt whose use in this application is known can be used without any particular limitation, and specific examples thereof include the followings:

inorganic lithium salts such as $LiPF_6$, $LiBF_4$, $LiClO_4$, $LiAlF_4$, $LiSbF_6$, $LiTaF_6$ and $LiWF_7$;

lithium tungstates such as $LiWOF_5$;

lithium carboxylate salts such as $HCO_2Li$, $CH_3CO_2Li$, $CH_2FCO_2Li$, $CHF_2CO_2Li$, $CF_3CO_2Li$, $CF_3CH_2CO_2Li$, $CF_3CF_2CO_2Li$, $CF_3CF_2CF_2CO_2Li$ and $CF_3CF_2CF_2CF_2CO_2Li$;

lithium sulfonate salts such as $FSO_3Li$, $CH_3SO_3Li$, $CH_2FSO_3Li$, $CHF_2SO_3Li$, $CF_3SO_3Li$, $CF_3CF_2SO_3Li$, $CF_3CF_2CF_2SO_3Li$ and $CF_3CF_2CF_2CF_2SO_3Li$;

lithium imide salts such as $LiN(FCO)_2$, $LiN(FCO)(FSO_2)$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide and $LiN(CF_3SO_2)(C_4F_9SO_2)$;

lithium methide salts such as $LiC(FSO_2)_3$, $LiC(CF_3SO_2)_3$ and $LiC(C_2F_5SO_2)_3$;

lithium oxalatoborate salts such as lithium difluorooxalatoborate and lithium bis(oxalato)borate;

lithium oxalatophosphate salts such as lithium tetrafluorooxalatophosphate, lithium difluorobis(oxalato)phosphate and lithium tris(oxalato)phosphate; and fluorine-containing organic lithium salts such as $LiPF_4(CF_3)_2$, $LiPF_4(C_2F_5)_2$, $LiPF_4(CF_3SO_2)_2$, $LiPF_4(C_2F_5SO_2)_2$, $LiBF_3CF_3$, $LiBF_3C_2F_5$, $LiBF_3C_3F_7$, $LiBF_2(CF_3)_2$, $LiBF_2(C_2F_5)_2$, $LiBF_2(CF_3SO_2)_2$ and $LiBF_2(C_2F_5SO_2)_2$.

Among these, $LiPF_6$, $LiBF_4$, $LiSbF_6$, $LiTaF_6$, $FSO_3Li$, $CF_3SO_3Li$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide, $LiC(FSO_2)_3$, $LiC(CF_3SO_2)_3$, $LiC(C_2F_5SO_2)_3$, lithium bisoxalatoborate, lithium difluorooxalatoborate, lithium tetrafluorooxalatophosphate, lithium difluorobisoxalatophosphate, $LiBF_3CF_3$, $LiBF_3C_2F_5$, $LiPF_3(CF_3)_3$, $LiPF_3(C_2F_5)_3$ and the like are preferred, because of their effect of enhancing, for example, output characteristics, high-rate charge/discharge characteristics, high-temperature storage characteristics, and cycle characteristics.

One of these lithium salts may be used alone, or two or more thereof may be used in combination. In the case of using two or more lithium salts in combination, preferred examples thereof include a combination of $LiPF_6$ and $LiBF_4$, and a combination of $LiPF_6$ and $FSO_3Li$, and these combinations have an effect of enhancing load characteristics or cycle characteristics.

In this case, the blending amount of $LiBF_4$ or $FSO_3Li$ in terms of concentration per 100 mass % of the entire nonaqueous electrolyte solution is not limited and may be arbitrary as long as the effects of the present invention are not seriously impaired, but the blending amount is usually 0.01 mass % or more, preferably 0.1 mass % or more, and usually 30 mass % or less, preferably 20 mass % or less, based on the nonaqueous electrolyte solution of the present invention.

Other examples include a combination of an inorganic lithium salt and an organic lithium salt, and the combination use of these two members has an effect of reducing deterioration due to high-temperature storage. The organic salt is preferably, for example, $CF_3SO_3Li$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide, $LiC(FSO_2)_3$, $LiC(CF_3SO_2)_3$, $LiC(C_2F_5SO_2)_3$, lithium bisoxalatoborate, lithium difluorooxalatoborate, lithium tetrafluorooxalatophosphate, lithium difluorobisoxalatophosphate, $LiBF_3CF_3$, $LiBF_3C_2F_5$, $LiPF_3(CF_3)_3$ or $LiPF_3(C_2F_5)_3$. In this case, the ratio of the organic lithium salt per 100 mass % of the entire nonaqueous electrolyte solution is preferably 0.1 mass % or more, more preferably 0.5 mass % or more, and preferably 30 mass % or less, more preferably 20 mass % or less.

As for the concentration of such a lithium salt in the nonaqueous electrolyte solution, the content of the lithium salt is not particularly limited as long as the effects of the present invention are not seriously impaired, but from the standpoint of adjusting the electric conductivity of the nonaqueous electrolyte solution to a proper range and ensuring good battery performance, the total molar concentration of lithium in the nonaqueous electrolyte solution is preferably 0.3 mol/L or more, more preferably 0.4 mol/L or more, still more preferably 0.5 mol/L or more, and preferably 3 mol/L or less, more preferably 2.5 mol/L or less, still more preferably 2.0 mol/L or less.

If the total molar concentration of lithium is too low, the electrolyte solution may be caused to have an insufficient electric conductivity, whereas if the concentration is too high, the electric conductivity may decrease due to a rise in the viscosity and the battery performance may be reduced.

1-4. Nonaqueous Solvent

The nonaqueous solvent for use in the present invention is not particularly limited, and a known organic solvent may be used. Examples thereof include a fluorine atom-free cyclic carbonate, a chain carbonate, a cyclic or chain carboxylic acid ester, an ether compound, and a sulfone-based compound.

<Fluorine Atom-Free Cyclic Carbonate>

The fluorine atom-free cyclic carbonate includes a cyclic carbonate having an alkylene group with a carbon number of 2 to 4.

Specific examples of the fluorine atom-free cyclic carbonate having an alkylene group with a carbon number of 2 to 4 include ethylene carbonate, propylene carbonate, and butylene carbonate. Among these, ethylene carbonate and propylene carbonate are preferred in view of enhancement of the battery characteristics owing to an increase in the lithium ion dissociation degree.

As for the fluorine atom-free cyclic carbonate, one kind may be used alone, or two or more kinds may be used together in any combination in an arbitrary ratio.

The blending amount of the fluorine atom-free cyclic carbonate is not particularly limited and may be arbitrary as long as the effects of the present invention are not seriously impaired, but in the case of using one kind of a fluorine atom-free cyclic carbonate alone, the blending amount is 5 vol % or more, preferably 10 vol % or more, per 100 vol % of the nonaqueous solvent. By setting the blending amount to this range, it becomes easy to prevent the electric conductivity from reduction due to a decrease in the dielectric constant of the nonaqueous electrolyte solution and provide a nonaqueous electrolyte battery excellent in large-current discharge characteristics, stability to negative electrode and cycle characteristics. Also, the blending amount is 95 vol % or less, preferably 90 vol % or less, more preferably 85 vol % or less. By setting the blending amount to this range, it becomes easy to adjust the viscosity of the nonaqueous electrolyte solution to an appropriate range, thereby suppressing reduction in the ionic conductivity, and provide a nonaqueous electrolyte battery excellent in load characteristics.

<Chain Carbonate>

The chain carbonate is preferably a chain carbonate having a carbon number of 3 to 7, more preferably a dialkyl carbonate having a carbon number of 3 to 7.

Specific examples of the chain carbonate include dimethyl carbonate, diethyl carbonate, di-n-propyl carbonate, diisopropyl carbonate, n-propyl isopropyl carbonate, ethyl methyl carbonate, methyl n-propyl carbonate, n-butyl methyl carbonate, isobutyl methyl carbonate, tert-butyl methyl carbonate, ethyl n-propyl carbonate, n-butyl ethyl carbonate, isobutyl ethyl carbonate, and tert-butyl ethyl carbonate.

Among these, dimethyl carbonate, diethyl carbonate, di-n-propyl carbonate, diisopropyl carbonate, n-propyl isopropyl carbonate, ethyl methyl carbonate and methyl-n-propyl carbonate are preferred, and dimethyl carbonate, diethyl carbonate and ethyl methyl carbonate are more preferred.

In addition, fluorine atom-containing chain carbonates (hereinafter, sometimes referred to as "fluorinated chain carbonate") may be also suitably used.

The number of fluorine atoms contained in the fluorinated chain carbonate is not particularly limited as long as it is 1 or more, but the number of fluorine atoms is usually 6 or less, preferably 4 or less. In the case where the fluorinated chain carbonate has a plurality of fluorine atoms, these fluorine atoms may be bonded to the same carbon or may be bonded to different carbons.

Examples of the fluorinated chain carbonate include a fluorinated dimethyl carbonate and a derivative thereof, a fluorinated ethyl methyl carbonate and a derivative thereof, and a fluorinated diethyl carbonate and a derivative thereof.

Examples of the fluorinated dimethyl carbonate and a derivative thereof include fluoromethyl methyl carbonate, difluoromethyl methyl carbonate, trifluoromethyl methyl carbonate, bis(fluoromethyl)carbonate, bis(difluoro)methyl carbonate, and bis(trifluoromethyl)carbonate.

Examples of the fluorinated ethyl methyl carbonate and a derivative thereof include 2-fluoroethyl methyl carbonate, ethyl fluoromethyl carbonate, 2,2-difluoroethyl methyl carbonate, 2-fluoroethyl fluoromethyl carbonate, ethyl difluoromethyl carbonate, 2,2,2-trifluoroethyl methyl carbonate, 2,2-difluoroethyl fluoromethyl carbonate, 2-fluoroethyl difluoromethyl carbonate, and ethyl trifluoromethyl carbonate.

Examples of the fluorinated diethyl carbonate and a derivative thereof include ethyl-(2-fluoroethyl)carbonate, ethyl-(2,2-difluoroethyl)carbonate, bis(2-fluoroethyl)carbonate, ethyl-(2,2,2-trifluoroethyl) carbonate, 2,2-difluoroethyl-2'-fluoroethyl carbonate, bis(2,2-difluoroethyl)carbonate, 2,2,2-trifluoroethyl-2'-fluoroethyl carbonate, 2,2,2-trifluoroethyl-2',2'-difluoroethyl carbonate, and bis(2,2,2-trifluoroethyl)carbonate.

As for the chain carbonate, one kind may be used alone, or two or more kinds may be used together in any combination in an arbitrary ratio.

The blending amount of the chain carbonate is preferably 5 vol % or more, more preferably 10 vol % or more, still more preferably 15 mol % or more, per 100 vol % of the nonaqueous solvent. By setting the lower limit as above, it becomes easy to adjust the viscosity of the nonaqueous electrolyte solution to an appropriate range, thereby suppressing reduction in the ionic conductivity, and provide a nonaqueous electrolyte battery excellent in large-current discharge characteristics. Also, the blending amount of the chain carbonate is preferably 90 vol % or less, more preferably 85 vol % or less, per 100 vol % the nonaqueous solvent. By setting the upper limit as above, it becomes easy to prevent the electric conductivity from reduction due to a decrease in the dielectric constant of the nonaqueous electrolyte solution and provide a nonaqueous electrolyte battery excellent in large-current discharge characteristics.

<Cyclic Carboxylic Acid Ester>

The cyclic carboxylic acid ester is preferably a cyclic carboxylic acid ester having a carbon number of 3 to 12.

Specific examples thereof include γ-butyrolactone, γ-valerolactone, γ-caprolactone, and ε-caprolactone. Among these, γ-butyrolactone is preferred in view of enhancement of the battery characteristics owing to an increase in the lithium ion dissociation degree.

As for the cyclic carboxylic acid ester, one kind may be used alone, or two or more kinds may be used together in any combination in an arbitrary ratio.

The blending amount of the cyclic carboxylic acid ester is usually, preferably 5 vol % or more, more preferably 10 vol % or more, per 100 vol % of the nonaqueous solvent. Within this range, it is easy to improve the electric conductivity of the nonaqueous electrolyte solution and enhance the large-current discharge characteristics of the nonaqueous electrolyte battery. Also, the blending amount of the cyclic carboxylic acid ester is preferably 50 vol % or less, more preferably 40 vol % or less. By setting the upper limit as above, it becomes easy to adjust the viscosity of the nonaqueous electrolyte solution to an appropriate range, thereby avoiding reduction in the ionic conductivity and suppressing increase in the resistance of the negative electrode, and provide a nonaqueous electrolyte secondary battery excellent in large-current discharge characteristics.

<Chain Carboxylic Acid Ester>

The chain carboxylic acid ester is preferably a chain carboxylic acid ester having a carbon number of 3 to 7. Specific examples thereof include:

methyl acetate, ethyl acetate, n-propyl acetate, isopropyl acetate, n-butyl acetate, isobutyl acetate, tert-butyl acetate, methyl propionate, ethyl propionate, n-propyl propionate, isopropyl propionate, n-butyl propionate, isobutyl propionate, tert-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

Among these, methyl acetate, ethyl acetate, n-propyl acetate, n-butyl acetate, methyl propionate, ethyl propionate, n-propyl propionate, isopropyl propionate, methyl butyrate, ethyl butyrate, and the like are preferred in view of enhancement of the ionic conductivity owing to a decrease in the viscosity.

As for the chain carboxylic acid ester, one kind may be used alone, or two or more kinds may be used together in any combination in an arbitrary ratio.

The blending amount of the chain carboxylic acid ester is usually, preferably 10 vol % or more, more preferably 15 vol % or more, per 100 vol % of the nonaqueous solvent. By setting the lower limit as above, it becomes easy to improve the electric conductivity of the nonaqueous electrolyte solution and enhance the large-current discharge characteristics of the nonaqueous electrolyte battery. Also, the blending amount of the chain carboxylic acid ester is preferably 60 vol % or less, more preferably 50 vol % or less, per 100 vol % of the nonaqueous solvent. By setting the upper limit as above, it becomes easy to suppress increase in the resistance of the negative electrode and provide a nonaqueous electrolyte battery excellent in large-current discharge characteristics and cycle characteristics.

<Ether-Based Compound>

The ether-based compound is preferably a chain ether having a carbon number of 3 to 10, in which a part of hydrogens may be substituted for by fluorine, or a cyclic ethers having a carbon number of 3 to 6.

Examples of the chain ether having a carbon number of 3 to 10 include:

diethyl ether, di(2-fluoroethyl)ether, di(2,2-difluoroethyl)ether, di(2,2,2-trifluoroethyl)ether, ethyl (2-fluoroethyl) ether, ethyl (2,2,2-trifluoroethyl)ether, ethyl (1,1,2,2-tetrafluoroethyl)ether, (2-fluoroethyl)(2,2,2-trifluoroethyl)ether, (2-fluoroethyl)(1,1,2,2-tetrafluoroethyl)ether, (2,2,2-trifluoroethyl)(1,1,2,2-tetrafluoroethyl)ether, ethyl-n-propyl ether, ethyl (3-fluoro-n-propyl)ether, ethyl (3,3,3-trifluoro-n-propyl)ether, ethyl (2,2,3,3-tetrafluoro-n-propyl)ether, ethyl (2,2,3,3,3-pentafluoro-n-propyl)ether, 2-fluoroethyl n-propyl ether, (2-fluoroethyl)(3-fluoro-n-propyl)ether, (2-fluoroethyl)(3,3,3-trifluoro-n-propyl)ether, (2-fluoroethyl)(2,2,3,3-tetrafluoro-n-propyl)ether, (2-fluoroethyl)(2,2,3,3,3-pentafluoro-n-propyl)ether, 2,2,2-trifluoroethyl-n-propyl ether, (2,2,2-trifluoroethyl)(3-fluoro-n-propyl)ether, (2,2,2-trifluoroethyl)(3,3,3-trifluoro-n-propyl)ether, (2,2,2-trifluoroethyl)(2,2,3,3-tetrafluoro-n-propyl)ether, (2,2,2-trifluoroethyl)(2,2,3,3,3-pentafluoro-n-propyl)ether, 1,1,2,2-tetrafluoroethyl-n-propyl ether, (1,1,2,2-tetrafluoroethyl)(3-fluoro-n-propyl)ether, (1,1,2,2-tetrafluoroethyl)(3,3,3-trifluoro-n-propyl)ether, (1,1,2,2-tetrafluoroethyl) (2,2,3,3-tetrafluoro-n-propyl)ether, (1,1,2,2-tetrafluoroethyl)(2,2,3,3,3-pentafluoro-n-propyl)ether, di-n-propyl ether, (n-propyl) (3-fluoro-n-propyl)ether, (n-propyl)(3,3,3-trifluoro-n-propyl)ether, (n-propyl)(2,2,3,3-tetrafluoro-n-propyl)ether, (n-propyl)(2,2,3,3,3-pentafluoro-n-propyl)ether, di(3- fluoro-n-propyl)ether, (3-fluoro-n-propyl)(3,3,3-trifluoro-n-propyl)ether, (3-fluoro-n-propyl)(2,2,3,3-tetrafluoro-n-propyl)ether, (3-fluoro-n-propyl)(2,2,3,3,3-pentafluoro-n-propyl)ether, di(3,3,3-trifluoro-n-propyl)ether, (3,3,3-trifluoro-n-propyl)(2,2,3,3-tetrafluoro-n-propyl)ether, (3,3,3-trifluoro-n-propyl)(2,2,3,3,3-pentafluoro-n-propyl)ether, di(2,2,3,3-tetrafluoro-n-propyl)ether, (2,2,3,3-tetrafluoro-n-propyl) (2,2,3,3,3-pentafluoro-n-propyl)ether, di(2,2,3,3,3-pentafluoro-n-propyl)ether, di-n-butyl ether, dimethoxymethane, methoxyethoxymethane, methoxy(2-fluoroethoxy)methane, methoxy(2,2,2-trifluoroethoxy)methane methoxy(1,1,2,2-tetrafluoroethoxy)methane, diethoxymethane, ethoxy(2-fluoroethoxy)methane, ethoxy(2,2,2-trifluoroethoxy)methane, ethoxy(1,1,2,2-tetrafluoroethoxy)methane, di(2-fluoroethoxy)methane, (2-fluoroethoxy)(2,2,2-trifluoroethoxy)methane, (2-fluoroethoxy)(1,1,2,2-tetrafluoroethoxy)methane di(2,2,2-trifluoroethoxy)methane, (2,2,2-trifluoroethoxy)(1,1,2,2-tetrafluoroethoxy)methane, di(1,1,2,2-tetrafluoroethoxy)methane, dimethoxyethane, methoxyethoxyethane, methoxy(2-fluoroethoxy)ethane, methoxy(2,2,2-trifluoroethoxy)ethane, methoxy(1,1,2,2-tetrafluoroethoxy)ethane, diethoxyethane, ethoxy(2-fluoroethoxy)ethane, ethoxy(2,2,2-trifluoroethoxy)ethane, ethoxy(1,1,2,2-tetrafluoroethoxy)ethane, di(2-fluoroethoxy)ethane, (2-fluoroethoxy)(2,2,2-trifluoroethoxy)ethane, (2-fluoroethoxy)(1,1,2,2-tetrafluoroethoxy) ethane, di(2,2,2-trifluoroethoxy)ethane, (2,2,2-trifluoroethoxy)(1,1,2,2-tetrafluoroethoxy)ethane, di(1,1,2,2-tetrafluoroethoxy)ethane, ethylene glycol di-n-propyl ether, ethylene glycol di-n-butyl ether, and diethylene glycol dimethyl ether.

Examples of the cyclic ether having a carbon number of 3 to 6 include tetrahydrofuran, 2-methyltetrahydrofuran, 3-methyltetrahydrofuran, 1,3-dioxane, 2-methyl-1,3-dioxane, 4-methyl-1,3-dioxane, 1,4-dioxane, and fluorination products of these compounds.

Among these, dimethoxymethane, diethoxymethane, ethoxymethoxymethane, ethylene glycol di-n-propyl ether, ethylene glycol di-n-butyl ether and diethylene glycol dimethyl ether are preferred in terms of having high solvation ability for lithium ion and thereby enhancing the ion dissociating property, and dimethoxymethane, diethoxymethane and ethoxymethoxymethane are more preferred, because the viscosity is low and in turn, high ionic conductivity is obtained.

As for the ether-based compound, one kind may be used alone, or two or more kinds may be used together in an combination and in an ratio.

The blending amount of the ether-based compound is usually, preferably 5 vol % or more, more preferably 10 vol % or more, still more preferably 15 vol % or more, and preferably 70 vol % or less, more preferably 60 vol % or less, still more preferably 50 vol % or less, per 100 vol % of the nonaqueous solvent.

Within these ranges, it is easy to ensure the effect of the chain ether on enhancing the lithium ion dissociation degree and enhancing the ionic conductivity due to a decrease in the viscosity, and in the case where the negative electrode active material is a carbonaceous material, it is easy to avoid a trouble that the chain ether is inserted together with lithium ion and the capacity is reduced.

<Sulfone-Based Compound>

The sulfone-based compound is preferably a cyclic sulfone having a carbon number of 3 to 6 or a chain sulfone having a carbon number of 2 to 6. The number of sulfonyl groups per molecule is preferably 1 or 2.

Examples of the cyclic sulfone having a carbon number of 3 to 6 include:

trimethylene sulfones, tetramethylene sulfones and hexamethylene sulfones, which are a monosulfone compound; and trimethylene disulfones, tetramethylene disulfones and hexamethylene disulfones, which are a disulfone compound.

Among these, in view of dielectric constant and viscosity, tetramethylene sulfones, tetramethylene disulfones, hexamethylene sulfones and hexamethylene disulfones are preferred, and tetramethylene sulfones (sulfolanes) are more preferred.

As the sulfolanes, sulfolane and/or a sulfolane derivative (hereinafter, sometimes collectively referred to, including sulfolane, as "sulfolanes") are preferred. The sulfolane derivative is preferably a derivative in which one or more hydrogen atoms bonded on carbon atoms constituting the sulfolane ring are substituted for by a fluorine atom or an alkyl group.

Among others, 2-methylsulfolane, 3-methylsulfolane, 2-fluorosulfolane, 3-fluorosulfolane, 2,2-difluorosulfolane, 2,3-difluorosulfolane, 2,4-difluorosulfolane, 2,5-difluorosulfolane, 3,4-difluorosulfolane, 2-fluoro-3-methylsulfolane, 2-fluoro-2-methylsulfolane, 3-fluoro-3-methylsulfolane, 3-fluoro-2-methylsulfolane, 4-fluoro-3-methylsulfolane, 4-fluoro-2-methylsulfolane, 5-fluoro-3-methylsulfolane, 5-fluoro-2-methylsulfolane, 2-fluoromethylsulfolane, 3-fluoromethylsulfolane, 2-difluoromethylsulfolane, 3-difluoromethylsulfolane, 2-trifluoromethylsulfolane, 3-trifluoromethylsulfolane, 2-fluoro-3-(trifluoromethyl)sulfolane, 3-fluoro-3-(trifluoromethyl)sulfolane, 4-fluoro-3-(trifluoromethyl)sulfolane, 5-fluoro-3-(trifluoromethyl)sulfolane and the like are preferred in terms of having high ionic conductivity and ensuring high input/output characteristics.

Examples of the chain sulfone having a carbon number of 2 to 6 include:

dimethyl sulfone, ethyl methyl sulfone, diethyl sulfone, n-propyl methyl sulfone, n-propyl ethyl sulfone, di-n-propyl sulfone, isopropyl methyl sulfone, isopropyl ethyl sulfone, diisopropyl sulfone, n-butyl methyl sulfone, n-butyl ethyl sulfone, tert-butyl methyl sulfone, tert-butyl ethyl sulfone, monofluoromethyl methyl sulfone, difluoromethyl methyl sulfone, trifluoromethyl methyl sulfone, monofluoroethyl methyl sulfone, difluoroethyl methyl sulfone, trifluoroethyl methyl sulfone, pentafluoroethyl methyl sulfone, ethyl monofluoromethyl sulfone, ethyl difluoromethyl sulfone, ethyl trifluoromethyl sulfone, perfluoroethyl methyl sulfone, ethyl trifluoroethyl sulfone, ethyl pentafluoroethyl sulfone, di(trifluoroethyl)sulfone, perfluorodiethyl sulfone, fluoromethyl-n-propyl sulfone, difluoromethyl-n-propyl sulfone, trifluoromethyl-n-propyl sulfone, fluoromethyl isopropyl sulfone, difluoromethyl isopropyl sulfone, trifluoromethyl isopropyl sulfone, trifluoroethyl-n-propyl sulfone, trifluoroethyl isopropyl sulfone, pentafluoroethyl-n-propyl sulfone, pentafluoroethyl isopropyl sulfone, trifluoroethyl-n-butyl sulfone, trifluoroethyl-tert-butyl sulfone, pentafluoroethyl-n-butyl sulfone, and pentafluoroethyl-tert-butyl sulfone.

Among these, dimethyl sulfone, ethyl methyl sulfone, diethyl sulfone, n-propyl methyl sulfone, isopropyl methyl sulfone, n-butyl methyl sulfone, tert-butyl methyl sulfone, monofluoromethyl methyl sulfone, difluoromethyl methyl sulfone, trifluoromethyl methyl sulfone, monofluoroethyl methyl sulfone, difluoroethyl methyl sulfone, trifluoroethyl methyl sulfone, pentafluoroethyl methyl sulfone, ethyl monofluoromethyl sulfone, ethyl difluoromethyl sulfone, ethyl trifluoromethyl sulfone, ethyl trifluoroethyl sulfone, ethyl pentafluoroethyl sulfone, trifluoromethyl-n-propyl sulfone, trifluoromethyl isopropyl sulfone, trifluoroethyl-n-butyl sulfone, trifluoroethyl-tert-butyl sulfone, trifluoromethyl-n-butyl sulfone, trifluoromethyl-tert-butyl sulfone and the like are preferred in terms of having high ionic conductivity and ensuring high input/output characteristics.

As for the sulfone-based compound, one kind may be used alone, or two or more kinds may be used together in any combination in an arbitrary ratio.

The blending amount of the sulfone-based compound is usually, preferably 0.3 vol % or more, more preferably 1 vol % or more, still more preferably 5 vol % or more, and preferably 40 vol % or less, more preferably 35 vol % or less, still more preferably 30 vol % or less, per 100 vol % of the nonaqueous solvent.

Within these ranges, the effect of enhancing durability such as cycle characteristics and storage characteristics is likely to be obtained and in addition, it is possible to adjust the viscosity of the nonaqueous electrolyte solution to an appropriate range and prevent reduction in the electric conductivity. Also, in the case of performing charging/discharging of the nonaqueous electrolyte battery at a high current density, a trouble such as decrease in the charge/discharge capacity retention ratio is less likely caused.

<In Case of Using Fluorine Atom-Containing Cyclic Carbonate as Nonaqueous Solvent>

In the present invention, in the case of using a fluorine atom-containing cyclic carbonate as a nonaqueous solvent, as for the nonaqueous solvent other than the fluorine atom-containing cyclic carbonate, one of nonaqueous solvents exemplified above may be combined with the fluorine atom-containing cyclic carbonate, or two or more thereof may be combined with the fluorine atom-containing cyclic carbonate and used together.

For example, one preferred combination of nonaqueous solvents is a combination mainly composed of a fluorine atom-containing cyclic carbonate and a chain carbonate. In particular, the total content of a fluorine atom-containing cyclic carbonate and a chain carbonate in the nonaqueous solvent is preferably 60 vol % or more, more preferably 80 vol % or more, still more preferably 90 vol % or more, and at the same time, the ratio of a fluorine atom-containing cyclic carbonate to the total of a fluorine atom-containing cyclic carbonate and a chain carbonate is 3 vol % or more, preferably 5 vol % or more, more preferably 10 vol % or more, still more preferably 15 vol % or more, and preferably 60 vol % or less, more preferably 50 vol % or less, still more preferably 40 vol % or less, yet still more preferably 35 vol % or less.

When such a combination of the nonaqueous solvent is used, the battery produced using the combination may be improved in the balance between cycle characteristics and high-temperature storage characteristics (particularly, the residual capacity and high-load discharge capacity after high-temperature storage).

Specific examples of the preferred combination of a fluorine atom-containing cyclic carbonate and a chain carbonate include:

a combination of monofluoroethylene carbonate and dimethyl carbonate, a combination of monofluoroethylene carbonate and diethyl carbonate, a combination of monofluoroethylene carbonate and ethyl methyl carbonate, a combination of monofluoroethylene carbonate, dimethyl carbonate and diethyl carbonate, a combination of monofluoroethylene carbonate, dimethyl carbonate and ethyl methyl carbonate, a combination of monofluoroethylene carbonate, diethyl carbonate and ethyl methyl carbonate, and a combination of monofluoroethylene carbonate, dimethyl carbonate, diethyl carbonate and ethyl methyl carbonate.

Among the combinations of a fluorine atom-containing cyclic carbonate and a chain carbonate, a combination containing symmetric chain alkyl carbonates as the chain carbonate is more preferred, and a combination containing monofluoroethylene carbonate, symmetric chain carbonates and asymmetric chain carbonates, such as a combination of monofluoroethylene carbonate, dimethyl carbonate and ethyl methyl carbonate, a combination of monofluoroethylene carbonate, diethyl carbonate and ethyl methyl carbonate and a combination of monofluoroethylene carbonate, dimethyl carbonate, diethyl carbonate and ethyl methyl carbonate, is more preferred because of good balance between cycle characteristics and large-current discharge characteristics. Above all, it is preferred that the symmetric chain carbonate is dimethyl carbonate, and the alkyl group of the chain carbonate is preferably an alkyl group having a carbon number of 1 to 2.

A combination in which a fluorine atom-free cyclic carbonate is further added to the above-described combination of a fluorine atom-containing cyclic carbonate and a chain carbonate, is also a preferred combination. Among others, the total content of a fluorine atom-containing cyclic carbonate and a fluorine atom-free cyclic carbonate in the nonaqueous solvent is preferably 10 vol % or more, more preferably 15 vol % or more, still more preferably 20 vol % or more, and at the same time, the ratio of a fluorine atom-containing cyclic carbonate to the total of a fluorine atom-containing cyclic carbonate and a fluorine atom-free cyclic carbonate is 5 vol % or more, preferably 10 vol % or more, more preferably 15 vol % or more, still more preferably 25 vol % or more, and preferably 95 vol % or less, more preferably 85 vol % or less, still more preferably 75 vol % or less, yet still more preferably 60 vol % or less.

When a fluorine atom-free cyclic carbonate is contained in this concentration range, the electric conductivity of the electrolyte solution can be maintained while forming a stable protective film on the negative electrode.

Specific examples of the preferred combination of a fluorine atom-containing cyclic carbonate, a fluorine atom-free cyclic carbonate and a chain carbonate include:

a combination of monofluoroethylene carbonate, ethylene carbonate and dimethyl carbonate, a combination of monofluoroethylene carbonate, ethylene carbonate and diethyl carbonate, a combination of monofluoroethylene carbonate, ethylene carbonate and ethyl methyl carbonate, a combination of monofluoroethylene carbonate, ethylene carbonate, dimethyl carbonate and diethyl carbonate, a combination of monofluoroethylene carbonate, ethylene carbonate, dimethyl carbonate and ethyl methyl carbonate, a combination of monofluoroethylene carbonate, ethylene carbonate, diethyl carbonate and ethyl methyl carbonate, a combination of monofluoroethylene carbonate, ethylene carbonate, dimethyl carbonate, diethyl carbonate and ethyl methyl carbonate, a combination of monofluoroethylene carbonate, propylene carbonate and dimethyl carbonate, a combination of monofluoroethylene carbonate, propylene carbonate and diethyl carbonate, a combination of monofluoroethylene carbonate, propylene carbonate and ethyl methyl carbonate, a combination of monofluoroethylene carbonate, propylene carbonate, dimethyl carbonate and diethyl carbonate, a combination of monofluoroethylene carbonate, propylene carbonate, dimethyl carbonate and ethyl methyl carbonate, a combination of monofluoroethylene carbonate, propylene carbonate, diethyl carbonate and ethyl methyl carbonate, a combination of monofluoroethylene carbonate, propylene carbonate, dimethyl carbonate, diethyl carbonate and ethyl methyl carbonate, a combination of monofluoroethylene carbonate, ethylene carbonate, propylene carbonate and dimethyl carbonate, a combination of monofluoroethylene carbonate, ethylene carbonate, propylene carbonate and diethyl carbonate, a combination of monofluoroethylene carbonate, ethylene carbonate, propylene carbonate and ethyl methyl carbonate, a combination of monofluoroethylene carbonate, ethylene carbonate, propylene carbonate, dimethyl carbonate and diethyl carbonate, a combination of monofluoroethylene carbonate, ethylene carbonate, propylene carbonate, dimethyl carbonate and ethyl methyl carbonate, a combination of monofluoroethylene carbonate, ethylene carbonate, propylene carbonate, diethyl carbonate and ethyl methyl carbonate, and a combination of monofluoroethylene carbonate, ethylene carbonate, propylene carbonate, dimethyl carbonate, diethyl carbonate and ethyl methyl carbonate.

Among the combinations of a fluorine atom-containing cyclic carbonate, a fluorine atom-free cyclic carbonate and a chain carbonate, a combination further containing symmetric alkyl carbonates as the chain carbonate is more preferred, and a combination containing monofluoroethylene carbonate, symmetric chain carbonates and asymmetric chain carbonates, such as:

a combination of monofluoroethylene carbonate, ethylene carbonate, dimethyl carbonate and ethyl methyl carbonate, a combination of monofluoroethylene carbonate, propylene carbonate, dimethyl carbonate and ethyl methyl carbonate, a combination of monofluoroethylene carbonate, ethylene carbonate, propylene carbonate, dimethyl carbonate and ethyl methyl carbonate, a combination of monofluoroethylene carbonate, ethylene carbonate, diethyl carbonate and ethyl methyl carbonate, a combination of monofluoroethylene carbonate, propylene carbonate, diethyl carbonate and ethyl methyl carbonate, a combination of monofluoroethylene carbonate, ethylene carbonate, propylene carbonate, diethyl carbonate and ethyl methyl carbonate, a combination of monofluoroethylene carbonate, ethylene carbonate, dimethyl carbonate, diethyl carbonate and ethyl methyl carbonate, a combination of monofluoroethylene carbonate, propylene carbonate, dimethyl carbonate, diethyl carbonate and ethyl methyl carbonate, and a combination of monofluoroethylene carbonate, ethylene carbonate, propylene carbonate, dimethyl carbonate, diethyl carbonate and ethyl monomethyl carbonate, is more preferred because of good balance between cycle characteristics and large-current discharge characteristics. Above all, it is preferred that the symmetric chain carbonate is dimethyl carbonate, and the alkyl group of the chain carbonate is preferably an alkyl group having a carbon number of 1 to 2.

In the case of incorporating dimethyl carbonate into the nonaqueous solvent, when dimethyl carbonate is contained in a ratio of preferably 10 vol % or more, more preferably 20 vol % or more, still more preferably 25 vol % or more, yet still more preferably 30 vol % or more, and preferably 90 vol % or less, more preferably 80 vol % or less, still more preferably 75 vol % or less, yet still more preferably 70 vol % or less, based on all nonaqueous solvents, the load characteristics of the battery may be enhanced.

In particular, it is preferred to contain dimethyl carbonate and ethyl methyl carbonate and set the content ratio of dimethyl carbonate to be larger than the content ratio of ethyl methyl carbonate, because battery characteristics after high-temperature storage are enhanced while allowing it to maintain the electric conductivity of the electrolyte solution.

From the standpoint of increasing the electric conductivity of the electrolyte solution and enhancing the battery characteristics after storage, the volume ratio of dimethyl carbonate to ethyl methyl carbonate (dimethyl carbonate/ethyl methyl carbonate) in all nonaqueous solvents is preferably 1.1 or more, more preferably 1.5 or more, still more preferably 2.5 or more.

In terms of enhancing the battery characteristics at low temperature, the volume ratio above (dimethyl carbonate/ethyl methyl carbonate) is preferably 40 or less, more preferably 20 or less, still more preferably 10 or less, yet still more preferably 8 or less.

In the combination mainly composed of a fluorine atom-containing cyclic carbonate and a chain carbonate, other solvents such as cyclic carboxylic acid esters, chain carboxylic acid esters, cyclic ethers, chain ethers, sulfur-containing organic solvents, phosphorus-containing organic solvents and fluorine-containing aromatic solvents may be mixed, in addition to the fluorine atom-free cyclic carbonate.

<In Case of Using Fluorine Atom-Containing Cyclic Carbonate as Auxiliary Agent>

In the present invention, in the case of using a fluorine atom-containing cyclic carbonate as an auxiliary agent, as for the nonaqueous solvent other than the fluorine atom-containing cyclic carbonate, one of nonaqueous solvents exemplified above may be used alone, or two or more thereof may be used together in any combination in an arbitrary ratio.

For example, one preferred combination of nonaqueous solvents is a combination mainly composed of a fluorine atom-free cyclic carbonate and a chain carbonate.

In particular, the total content of a fluorine atom-free cyclic carbonate and a chain carbonate in the nonaqueous solvent is preferably 70 vol % or more, more preferably 80 vol % or more, still more preferably 90 vol % or more, and at the same time, the ratio of a fluorine atom-free cyclic carbonate to the total of a cyclic carbonate and a chain carbonate is preferably 5 vol % or more, more preferably 10 vol % or more, still more preferably 15 vol % or more, and preferably 50 vol % or less, more preferably 35 vol % or less, still more preferably 30 vol % or less, yet still more preferably 25 vol % or less.

When such a combination of the nonaqueous solvent is used, the battery produced using the combination may be improved in the balance between cycle characteristics and high-temperature storage characteristics (particularly, the residual capacity and high-load discharge capacity after high-temperature storage).

Specific examples of the preferred combination of a fluorine atom-free cyclic carbonate and a chain carbonate include:

a combination of ethylene carbonate and dimethyl carbonate, a combination of ethylene carbonate and diethyl carbonate, a combination of ethylene carbonate and ethyl methyl carbonate, a combination of ethylene carbonate, dimethyl carbonate and diethyl carbonate, a combination of ethylene carbonate, dimethyl carbonate and ethyl methyl carbonate, a combination of ethylene carbonate, diethyl carbonate and ethyl methyl carbonate, and a combination of ethylene carbonate, dimethyl carbonate, diethyl carbonate and ethyl methyl carbonate.

Among the combinations of a fluorine atom-free cyclic carbonate and a chain carbonate, a combination containing asymmetric chain alkyl carbonates as the chain carbonate is more preferred, and a combination containing ethylene carbonate, symmetric chain carbonates and asymmetric chain carbonates, such as a combination of ethylene carbonate, dimethyl carbonate and ethyl methyl carbonate, a combination of ethylene carbonate, diethyl carbonate and ethyl methyl carbonate and a combination of ethylene carbonate, dimethyl carbonate, diethyl carbonate and ethyl methyl carbonate, is more preferred because of good balance between cycle characteristics and large-current discharge characteristics.

Above all, it is preferred that the asymmetric chain carbonate is ethyl methyl carbonate, and the alkyl group of the chain carbonate is preferably an alkyl group having a carbon number of 1 to 2.

A combination in which propylene carbonate is further added to the above-described combination of ethylene carbonate and a chain carbonate, is also a preferred combination.

In the case of containing propylene carbonate, the volume ratio between ethylene carbonate and propylene carbonate is preferably from 99:1 to 40:60, more preferably 95:5 to 50:50. Furthermore, the proportion of propylene carbonate in the entire nonaqueous solvent is preferably 0.1 vol % or more, more preferably 1 vol % or more, still more preferably 2 vol % or more, and preferably 20 vol % or less, more preferably 8 vol % or less, still more preferably 5 vol % or less.

When propylene carbonate is contained in this concentration range, the low-temperature characteristics may become more excellent while maintaining the characteristics of the combination of ethylene carbonate and a chain carbonate and therefore, the concentration range above is preferred.

In the case of incorporating dimethyl carbonate into the nonaqueous solvent, when dimethyl carbonate is contained in a ratio of preferably 10 vol % or more, more preferably 20 vol % or more, still more preferably 25 vol % or more, yet still more preferably 30 vol % or more, and preferably 90 vol % or less, more preferably 80 vol % or less, still more preferably 75 vol % or less, yet still more preferably 70 vol % or less, based on all nonaqueous solvents, the load characteristics of the battery may be enhanced.

In particular, it is preferred to contain dimethyl carbonate and ethyl methyl carbonate and set the content ratio of dimethyl carbonate to be larger than the content ratio of ethyl methyl carbonate, because battery characteristics after high-temperature storage are enhanced while allowing it to maintain the electric conductivity of the electrolyte solution.

From the standpoint of increasing the electric conductivity of the electrolyte solution and enhancing the battery characteristics after storage, the volume ratio of dimethyl carbonate to ethyl methyl carbonate (dimethyl carbonate/ethyl methyl carbonate) in all nonaqueous solvents is preferably 1.1 or more, more preferably 1.5 or more, still more preferably 2.5 or more. In terms of enhancing the battery characteristics at low temperature, the volume ratio above (dimethyl carbonate/ethyl methyl carbonate) is preferably 40 or less, more preferably 20 or less, still more preferably 10 or less, yet still more preferably 8 or less.

In the combination mainly composed of a fluorine atom-free cyclic carbonate and a chain carbonate, other solvents such as cyclic carboxylic acid esters, chain carboxylic acid esters, cyclic ethers, chain ethers, sulfur-containing organic solvents, phosphorus-containing organic solvents and fluorine-containing aromatic solvents may be mixed.

In the description of the present invention, the volume of the nonaqueous solvent is a value measured at 25° C., but as for a nonaqueous solvent that is solid at 25° C., such as ethylene carbonate, a value measured at the melting point is used.

1-5. Auxiliary Agent

In the nonaqueous electrolyte battery of the present invention, in addition to the sulfonic acid ester represented by formula (1), an auxiliary agent may be appropriately used according to the purpose. Examples of the auxiliary agent include a fluorine atom-containing unsaturated cyclic carbonate, an overcharge inhibitor, and other auxiliary agents, which are described below.

<Fluorinated Unsaturated Cyclic Carbonate>

As the fluorinated cyclic carbonate, a cyclic carbonate having an unsaturated bond and a fluorine atom (hereinafter, sometimes referred to as "fluorinated unsaturated cyclic carbonate") is also preferably used. The number of fluorine atoms in the fluorinated unsaturated cyclic carbonate is not particularly limited as long as it is 1 or more. The number of fluorine atoms is usually 6 or less, preferably 4 or less, and most preferably 1 or 2.

The fluorinated unsaturated cyclic carbonate includes, for example, a fluorinated vinylene carbonate derivative and a fluorinated ethylene carbonate derivative substituted with an aromatic ring or a substituent having a carbon-carbon double bond.

Examples of the fluorinated vinylene carbonate derivative include 4-fluorovinylene carbonate, 4-fluoro-5-methylvinylene carbonate, 4-fluoro-5-phenylvinylene carbonate, 4-allyl-5-fluorovinylene carbonate, and 4-fluoro-5-vinylvinylene carbonate.

Examples of the fluorinated ethylene carbonate derivative substituted with an aromatic ring or a substituent having a carbon-carbon double bond include:

4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, 4,5-difluoro-4,5-diallylethylene carbonate, 4-fluoro-4-phenylethylene carbonate, 4-fluoro-5-phenylethylene carbonate, 4,4-difluoro-5-phenylethylene carbonate, and 4,5-difluoro-4-phenylethylene carbonate.

Among others, as the fluorinated unsaturated cyclic carbonate preferred for combination use with the sulfonic acid ester represented by formula (1):

4-fluorovinylethylene carbonate, 4-fluoro-5-methylvinylene carbonate, 4-fluoro-5-vinylvinylene carbonate, 4-allyl-5-fluorovinylene carbonate, 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate and 4,5-difluoro-4,5-diallylethylene carbonate are more preferably used, because these form a stable interface protective film.

The molecular weight of the fluorinated unsaturated cyclic carbonate is not particularly limited and may be arbitrary as long as the effects of the present invention are not seriously impaired. The molecular weight is preferably 50 or more and preferably 250 or less. Within this range, it is easy to ensure the solubility of the fluorinated cyclic carbonate for the nonaqueous electrolyte solution and bring out the effects of the present invention.

The fluorinated unsaturated cyclic carbonate is not particularly limited in its production method and may be produced by arbitrarily selecting a known method. The molecular weight is more preferably 100 or more and more preferably 200 or less.

As for the fluorinated unsaturated cyclic carbonate, one kind may be used alone, or two or more kinds may be used together in any combination in an arbitrary ratio. The blending amount of the fluorinated unsaturated cyclic carbonate is not particularly limited and may be arbitrary as long as the effects of the present invention are not seriously impaired.

The blending amount of the fluorinated unsaturated cyclic carbonate is preferably 0.01 mass % or more, more preferably 0.1 mass % or more, still more preferably 0.2 mass % or more, and preferably 5 mass % or less, more preferably 4 mass % or less, still more preferably 3 mass % or less, per 100 mass % of the nonaqueous electrolyte solution.

Within these ranges, it is easy for the nonaqueous electrolyte battery to exert a sufficient enhancing effect on cycle characteristics and avoid a trouble that high-temperature storage characteristics are reduced or the discharge capacity retention ratio decreases due to an increase in the amount of gas evolved.

<Overcharge Inhibitor>

In the nonaqueous electrolyte solution of the present invention, an overcharge inhibitor can be used so as to effectively inhibit the nonaqueous electrolyte battery from bursting or firing when brought into an overcharged state or the like.

Examples of the overcharge inhibitor include:

an aromatic compound such as biphenyl, alkylbiphenyl, terphenyl, partially hydrogenated terphenyl, cyclohexylbenzene, tert-butylbenzene, tert-amylbenzene, diphenyl ether and dibenzofuran; a partial fluorination product of the aromatic compound, such as 2-fluorobiphenyl, o-cyclohexylfluorobenzene and p-cyclohexylfluorobenzene; and a fluorine-containing anisole compound such as 2,4-difluoroanisole, 2,5-difluoroanisole, 2,6-difluoroanisole and 3,5-difluoroanisole.

Among these, an aromatic compound such as biphenyl, alkylbiphenyl, terphenyl, partially hydrogenated terphenyl, cyclohexylbenzene, tert-butylbenzene, tert-amylbenzene, diphenyl ether and dibenzofuran is preferred.

One of these compounds may be used alone, or two or more thereof may be used in combination. In the case of using two or more compounds in combination, in view of balance between overcharge inhibiting characteristics and high-temperature storage characteristics, it is preferred to use a combination of cyclohexylbenzene and tert-butylbenzene or tert-amylbenzene or a combination of at least one member selected from oxygen-free aromatic compounds such as biphenyl, alkylbiphenyl, terphenyl, partially hydrogenated terphenyl, cyclohexylbenzene, tert-butylbenzene and tart-amylbenzene, and at least one member selected from oxygen-containing aromatic compounds such as diphenyl ether and dibenzofuran.

The blending amount of the overcharge inhibitor is not particularly limited and may be arbitrary as long as the effects of the present invention are not seriously impaired. The blending amount of the overcharge inhibitor is preferably 0.1 mass % or more and preferably 5 mass % or less, per 100 mass % of the nonaqueous electrolyte solution. Within this range, it is easy to sufficiently bring out the effect of the overcharge inhibitor and avoid a trouble that battery characteristics such as high-temperature storage characteristics are reduced.

The blending amount of the overcharge inhibitor is more preferably 0.2 mass % or more, still more preferably 0.3 mass % or more, yet still more preferably 0.5 mass % or more, and more preferably 3 mass % or less, still more preferably 2 mass % or less.

<Other Auxiliary Agents>

In the nonaqueous electrolyte solution of the present invention, other known auxiliary agents can be used. Examples of other auxiliary agents include:

a carbonate compound such as erythritan carbonate, spirobis-dimethylene carbonate and methoxyethyl-methyl carbonate; a carboxylic acid anhydride such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride and phenylsuccinic anhydride;

a spiro compound such as 2,4,8,10-tetraoxaspiro[5.5]undecane and 3,9-divinyl-2,4,8,10-tetraoxaspiro[5.5]undecane;

a sulfur-containing compound such as ethylene sulfite, methyl fluorosulfonate, ethyl fluorosulfonate, methyl methanesulfonate, ethyl methanesulfonate, busulfan, sulfolene, diphenyl sulfone, N,N-dimethylmethanesulfonamide and N,N-diethylmethanesulfonamide;

a nitrogen-containing compound such as 1-methyl-2-pyrrolidinone, 1-methyl-2-piperidone, 3-methyl-2-oxazolidinone, 1,3-dimethyl-2-imidazolidinone and N-methylsuccinimide;

a hydrocarbon compound such as heptane, octane, nonan, decane and cycloheptane; and a fluorine-containing aromatic compound such as fluorobenzene, difluorobenzene, hexafluorobenzene and benzotrifluoride.

One of these compounds may be used alone, or two or more thereof may be used in combination. By adding such an auxiliary agent, capacity retention characteristics and cycle characteristics after high-temperature storage can be enhanced.

The blending amount of the other auxiliary agent is not particularly limited and may be arbitrary as long as the effects of the present invention are not seriously impaired. The blending amount of the other auxiliary agent is preferably 0.01 mass % or more and preferably 5 mass % or less, per 100 mass % of the nonaqueous electrolyte solution. Within this range, it is easy to sufficiently bring out the effects of the other auxiliary agent and avoid a trouble that battery characteristics such as high-load discharge characteristics are reduced.

The blending amount of the other auxiliary agent is more preferably 0.1 mass % or more, still more preferably 0.2 mass % or more, and more preferably 3 mass % or less, still more preferably 1 mass % or less.

The nonaqueous electrolyte solution described above encompasses a nonaqueous electrolyte solution present in the inside of the nonaqueous electrolyte battery referred to in the present invention.

Specifically, the nonaqueous electrolyte solution encompasses a nonaqueous electrolyte solution in a nonaqueous electrolyte battery, which is obtained by separately synthesizing constituent elements for a nonaqueous electrolyte solution, such as lithium salt, solvent and auxiliary agent, preparing a nonaqueous electrolyte solution from these substantially isolated constituent elements, and injecting the nonaqueous electrolyte solution into a battery separately assembled by the method described later; a nonaqueous electrolyte solution obtained by separately putting constituent elements for the nonaqueous electrolyte solution of the present invention into a battery and mixing the constituent elements in the battery to give the same composition as that of the nonaqueous electrolyte solution of the present invention; and a nonaqueous electrolyte solution obtained by generating compounds constituting the nonaqueous electrolyte solution of the present invention in the nonaqueous electrolyte battery to give the same composition as that of the nonaqueous electrolyte solution of the present invention.

2. Battery Configuration

The nonaqueous electrolyte solution of the present invention is suitably used as an electrolyte solution for a secondary battery, for example, a lithium secondary battery, out of nonaqueous electrolyte batteries. A nonaqueous electrolyte battery using the nonaqueous electrolyte solution of the present invention is described below.

The nonaqueous electrolyte battery of the present invention can employ a known structure and typically has negative and positive electrodes capable of occluding•releasing an ion (for example, lithium ion), and the above-described nonaqueous electrolyte solution of the present invention.

2-1. Negative Electrode

The negative electrode active material is not particularly limited as long as it is a material capable of electrochemically occluding-releasing a lithium ion. Specific examples thereof include a carbonaceous material, an alloy-based material, and a lithium-containing metal composite oxide material. One of these materials may be used alone, or two or more thereof may be used together in any combination.

<Negative Electrode Active Material>

Out of the carbonaceous materials, the carbonaceous material used as the negative electrode active material is preferably selected from:

(1) natural graphite, (2) a carbonaceous material obtained by heat-treating an artificial carbonaceous substance and an artificial graphitic substance at least once at 400 to 3,200° C., (3) a carbonaceous material giving a negative electrode active material layer that is composed of at least two or more carbonaceous substances differing in the crystallinity and/or has an interface at which the carbonaceous substances differing in the crystallinity are in contact with each other, and (4) a carbonaceous material giving a negative electrode active material layer that is composed of at least two or more carbonaceous substances differing in the orientation and/or has an interface at which the carbonaceous substances differing in the orientation are in contact with each other, because a good balance is obtained between initial irreversible capacity and high current density charge/discharge characteristics. Also, one of these carbonaceous materials of (1) to (4) may be used alone, or two or more thereof may be used together in any combination in an arbitrary ratio.

Examples of the artificial carbonaceous substance and artificial graphitic substance of (2) include:

natural graphite, coal coke, petroleum coke, coal pitch, petroleum pitch, a carbonaceous substance obtained by oxidizing such a pitch, needle coke, pitch coke, a carbon material obtained by partially graphitizing such a coke, a pyrolysis product of an organic material, such as furnace black, acetylene black and pitch-derived carbon fiber, a carbonizable organic material, a carbonization product of the carbonizable organic material, a solution obtained by dissolving a carbonizable organic material in a low molecular organic solvent such as benzene, toluene, xylene, quinoline and n-hexane, and a carbonization product of such a solution.

The alloy-based material used as the negative electrode active material is not particularly limited as long as it is a material capable of occluding•releasing lithium, and may be any one of simple lithium, a simple metal or alloy for forming a lithium alloy, and its compound such as oxide, carbide, nitride, silicide, sulfide and phosphide.

The simple metal or alloy for forming a lithium alloy is preferably a material containing a metal•semimetal element (that is, excluding carbon) belonging to Groups 13 and 14, more preferably a simple metal of aluminum, silicon or tin (hereafter, these sometimes referred to as "specific metal element"), or an alloy or compound containing such an atom.

One of these may be used alone, or two or more thereof may be used together in any combination and in an arbitrary ratio.

The negative electrode active material having at least one atom selected from specific metal elements includes: a simple metal of any one kind of a specific metal element; an alloy composed of two or more kinds of specific metal elements; an alloy composed of one kind or two or more kinds of specific metal elements and one kind or two or more kinds of other metal elements; a compound containing one kind or two or more kinds of specific metal elements; and a composite compound such as oxide, carbide, nitride, silicide, sulfide and phosphide of the compound above.

By using such a simple metal, alloy or metal compound as the negative electrode active material, the capacity of the battery can be increased.

The composite compound includes a compound to which several kinds of elements such as simple metal, alloy and nonmetallic element are connected in a complex manner. Specifically, for example, in the case of silicon and tin, an alloy of such an element and a metal incapable of acting as a negative electrode may be used. In the case of tin, a complicated compound containing five or six kinds of elements obtained by combining tin with a metal capable of acting a negative electrode except for silicon, a metal incapable of acting as a negative electrode, and a nonmetallic element may be also used.

Among these negative electrode active materials, for example, a simple metal of any one kind of a specific metal element, an alloy of two or more kinds of specific metal elements, and an oxide, carbide or nitride of a specific metal element are preferred because of large capacity per unit mass of the battery fabricated, and a simple metal, an alloy, an oxide, a carbide, a nitride and the like of silicon and/or tin are more preferred in view of capacity per unit mass and environmental load.

The lithium-containing metal composite oxide material used as the negative electrode active material is not particularly limited as long as it is a material capable of occluding•releasing lithium, but, in view of high current density charge/discharge characteristics, the lithium-containing metal composite oxide material is preferably a material containing titanium and lithium, more preferably a lithium-containing composite metal oxide material containing titanium, still more preferably a composite oxide of lithium and titanium (hereinafter, sometimes referred to as "lithium-titanium composite oxide"). That is, when a lithium-titanium composite oxide having a spinel structure is used by incorporating it into a negative electrode active material for a nonaqueous electrolyte battery, the output resistance can be greatly reduced and therefore, this is particularly preferred.

In addition, a metal oxide where lithium or titanium in a lithium-titanium composite oxide is substituted with another metal element, for example, at least one element selected from the group consisting of Na, K, Co, Al, Fe, Ti, Mg, Cr, Ga, Cu, Zn and Nb, is also preferred.

It is preferred that the metal oxide is a lithium-titanium composite oxide represented by formula (A) and in formula (A), 0.7≤x≤1.5, 1.5≤y≤2.3 and 0≤z≤1.6, because the structure at the time of doping and dedoping of a lithium ion is stable.

$$Li_xTi_yM_zO_4 \quad (A)$$

(wherein M represents at least one element selected from the group consisting of Na, K, Co, Al, Fe, Ti, Mg, Cr, Ga, Cu, Zn and Nb).

Among the compositions represented by formula (A), structures where
  (a) 1.2≤x≤1.4, 1.5≤y≤1.7, z=0,
  (b) 0.9≤x≤1.1, 1.9≤y≤2.1, z=0, and
  (c) 0.7≤x≤0.9, 2.1≤y≤2.3, z=0
are preferred, because the battery performance balance is good.

Particularly preferred representative compositions of the compound above are $Li_{4/3}Ti_{5/3}O_4$ for (a), $Li_1Ti_2O_4$ for (b) and $Li_{4/5}Ti_{11/5}O_4$ for (c). With respect to the structure where Z≠0, for example, $Li_{4/3}Ti_{4/3}Al_{1/3}O_4$ is preferred.

<Physical Properties of Carbonaceous Material>

In the case of using a carbonaceous material as the negative electrode active material, the carbonaceous material preferably has the following physical properties.

(X-Ray Parameter)

The d-value (interplanar spacing) between lattice planes (002) of the carbonaceous material as determined by X-ray diffractometry according to the method by Gakushin (the Japan Society for the Promotion of Science) is preferably 0.335 nm or more and is usually 0.360 nm or less, preferably 0.350 nm or less, more preferably 0.345 nm or less. Also, the crystallite size (Lc) of the carbonaceous material as determined by X-ray diffractometry according to the Gakushin method is preferably 1.0 nm or more, more preferably 1.5 nm or more.

(Volume Average Particle Diameter)

The volume average particle diameter of the carbonaceous material is an average particle diameter (median diameter) on the volume basis as determined by the laser diffraction/scattering method and is usually 1 μm or more, preferably 3 μm or more, still more preferably 5 μm or more, yet still more preferably 7 μm or more, and usually 100 μm or less, preferably 50 μm or less, more preferably 40 μm or less, still more preferably 30 μm or less, yet still more preferably 25 μm or less.

If the volume average particle diameter is less than the ranges above, irreversible capacity may be increased to cause loss of the initial battery capacity. If the volume average particle diameter exceeds the above-described ranges, a non-uniform coating surface is likely to be formed when producing an electrode by coating and this is sometimes disadvantageous in view of the battery production process.

The volume average particle diameter is measured by dissolving the carbon powder in a 0.2 mass % aqueous solution (about 10 mL) of polyoxyethylene (20) sorbitan monolaurate as a surfactant and using a laser diffraction/scattering particle size distribution analyzer (LA-700, manufactured by Horiba Ltd.).

(Raman R. Value, Raman Half-Value Width)

The Raman R value of the carbonaceous material is a value measured by the argon-ion laser Raman spectroscopy and is usually 0.01 or more, preferably 0.03 or more, more preferably 0.1 or more, and usually 1.5 or less, preferably 1.2 or less, more preferably 1 or less, still more preferably 0.5 or less.

The Raman half-value width around 1580 cm$^{-1}$ of the carbonaceous material is not particularly limited and is usually 10 cm$^{-1}$ or more, preferably 15 cm$^{-1}$ or more, and usually 100 cm$^{-1}$ or less, preferably 80 cm$^{-1}$ or less, more preferably 60 cm$^{-1}$ or less, still more preferably 40 cm$^{-1}$ or less.

The Raman R value and Raman half-value width are indices indicative of crystallinity on the carbonaceous material surface, and the carbonaceous material preferably has appropriate crystallinity in view of chemical stability and does not lose a site for Li intercalation between layers upon charging/discharging, that is, has crystallinity high enough not to cause a decrease in the charging acceptance. Incidentally, in the case of increasing the density of the negative electrode by pressing after coating on a collector, crystals are liable to be oriented in the direction parallel to the electrode plate and therefore, it is preferred to take this fact into consideration. When the Raman R value and Raman half-value width are in the ranges above, not only a suitable film can be formed on the negative electrode surface to enhance storage characteristics, cycle characteristics and load characteristics but also reduction in the efficiency or evolution of a gas, accompanying the reaction with the nonaqueous electrolyte solution, can be suppressed.

The Raman spectrum is measured using a Raman spectrometer (Raman spectrometer manufactured by JASCO Corp.) by naturally dropping a sample into a measurement cell to fill the cell and rotating the cell within a plane perpendicular to an argon ion laser beam while irradiating the sample surface in the cell with the laser beam. In the obtained Raman spectrum, the intensity Ia of peak PA around 1580 cm$^{-1}$ and the intensity Ib of peak PB around 1360 cm$^{-1}$ are measured, and the intensity ratio R (R=Ib/Ia) therebetween is calculated.

The measurement conditions of Raman spectroscopic analysis are as follows.
  Argon-ion laser wavelength: 514.5 nm
  Laser power on sample: from 15 to 25 mW
  Resolution: from 10 to 20 cm$^{-1}$
  Measurement range: from 1,100 to 1,730 cm$^{-1}$
  Raman R value, Raman half-value width analysis:
  background processing
  Smoothing: simple average, 5-point convolution (BET Specific Surface Area)

The BET specific surface area of the carbonaceous material is a value of the specific surface area measured by the BET method and is usually 0.1 m$^2$·g$^{-1}$ or more, preferably 0.7 m$^2$·g$^{-1}$ or more, more preferably 1.0 m$^2$·g$^{-1}$ or more, still more preferably 1.5 m$^2$·g$^{-1}$ or more, and usually 100 m$^2$·g$^{-1}$ or less, preferably 25 m$^2$·g$^{-1}$ or less, more preferably 15 m$^2$·g$^{-1}$ or less, still more preferably 10 m$^2$·g$^{-1}$ or less.

When the value of the BET specific surface area is in the ranges above, deposition of lithium on the electrode surface can be reduced and at the same time, evolution of a gas due to reaction with the nonaqueous electrolyte solution can be suppressed.

In measuring the specific surface area by the BET method, a surface area meter (a fully automatic surface area measuring apparatus manufactured by Ohkura Riken Co., Ltd.) is used and after preliminarily drying a sample at 350° C. for 15 minutes in a nitrogen gas stream, the measurement is performed by the nitrogen adsorption BET one-point method in accordance with a gas-flow process using a nitrogen-helium mixed gas that is precisely adjusted to give a relative nitrogen pressure value of 0.3 with respect to atmospheric pressure.

(Roundness)

The roundness, when measured to determine the degree of sphericity of the carbonaceous material, preferably falls in the following range. Incidentally, the roundness is defined by "roundness=(peripheral length of equivalent circle having the same area as projected particle shape)/(actual peripheral length of projected particle shape)", and when the roundness is 1, the particle is a theoretically perfect sphere.

When the carbonaceous material has a particle diameter of 3 to 40 μm, the roundness of the particle is preferably closer to 1 and is preferably 0.1 or more, more preferably 0.5 or more, still more preferably 0.8 or more, yet still more preferably 0.85 or more, even yet still more preferably 0.9 or more.

As the roundness is higher, the packing property is more enhanced, reducing the resistance between particles, and therefore, the high current density charge/discharge characteristics are more improved. For this reason, the roundness is preferably higher as in the range above.

The roundness is measured using a flow-type particle image analyzer (FPIA manufactured by Sysmex Industrial Corp.). About 0.2 g of a sample is dispersed in a 0.2 mass % aqueous solution (about 50 mL) of polyoxyethylene (20) sorbitan monolaurate as a surfactant and after irradiating the dispersion with an ultrasonic wave of 28 kHz at an output of 60 W for 1 minute, the roundness is measured on particles having a particle diameter of 3 to 40 μm by setting the detection range to the range of 0.6 to 400 μm.

The method for enhancing the roundness is not particularly limited, but a carbonaceous material rounded by applying a rounding treatment is preferred, because in the electrode produced, interstices between particles become uniform in shape. Examples of the rounding treatment include a method of applying a shear force or a compressive force and thereby mechanically making the shape close to sphere, and a mechanical•physical treatment method of achieving granulation by utilizing the adhesive force of the particle itself.

(Tap Density)

The tap density of the carbonaceous material is usually 0.1 g·cm$^{-3}$ or more, preferably 0.5 g·cm$^{-3}$ or more, more preferably 0.7 g·cm$^{-3}$ or more, still more preferably 1 g·cm$^{-3}$ or more, and preferably 2 g·cm$^{-3}$ or less, more preferably 1.8 g·cm$^{-3}$ or less, still more preferably 1.6 g·cm$^{-3}$ or less. When the tap density in the ranges above, the battery capacity can be ensured and at the same time, an increase in the resistance between particles can be suppressed.

In the measurement of the tap density, a sample is dropped through a sieve having an opening size of 300 μm into a 20 cm$^3$ tapping cell until the cell is filled up to the top surface, and after tapping 1,000 times with a stroke length of 10 mm by using a powder densitometer (for example, Tap Denser manufactured by Seishin Enterprise Co., Ltd.), the tap density is calculated from the volume at that time and the mass of the sample.

(Orientation Ratio)

The orientation ratio of the carbonaceous material is usually 0.005 or more, preferably 0.01 or more, more preferably 0.015 or more, and usually 0.67 or less. When the orientation ratio is in these ranges, excellent high density charge/discharge characteristics can be ensured. Incidentally, the upper limit of the range above is a theoretical upper limit of the orientation ratio of the carbonaceous material.

The orientation ratio is measured by X-ray diffractometry after a sample is pressure-molded. A molded product obtained by packing 0.47 g of a sample into a molding machine with a diameter of 17 mm and compressing the sample at 58.8 MN·m$^{-2}$ is set using clay to become flush with the surface of a measurement sample holder and measured by X-ray diffraction. The ratio represented by (110) diffraction peak intensity/(004) diffraction peak intensity is calculated from the obtained peak intensities of (110) diffraction and (004) diffraction for carbon.

The measurement conditions of X-ray diffractometry are as follows. Here, "2θ" indicates a diffraction angle.

Target: Cu (Kα line) graphite monochromator
Slit:
Divergence slit=0.5°
Receiving slit=0.15 mm
Scattering slit=0.5°
Measurement range and step angle/measuring time:
(110) plane: 75°≤2θ≤80°, 1°/60 sec
(004) plane: 52°≤2θ≤57°, 1°/60 sec (Aspect Ratio (Powder))

The aspect ratio of the carbonaceous material is usually 1 or more and usually 10 or less, preferably 8 or less, more preferably 5 or less. Within these ranges, streaking during electrode plate formation is suppressed and more uniform coating becomes possible, so that excellent high current density charge/discharge characteristics can be ensured. Incidentally, the lower limit of the range above is a theoretical lower limit of the aspect ratio of the carbonaceous material.

The aspect ratio is measured by observing particles of the carbonaceous material through a scanning electron microscope (SEM) in an enlarged manner. By selecting arbitrary 50 graphite particles fixed to an edge face of a metal having a thickness of 50 μm or less, the longest diameter A of the carbonaceous material particle when three-dimensionally observed and the shortest diameter B perpendicular to the longest diameter are measured on each particle by rotating and inclining the stage to which the sample is fixed, and the average value of A/B is determined.

<Configuration and Production Method of Negative Electrode>

The electrode can be produced using any known method as long as the effects of the present invention are not seriously impaired. For example, a binder, a solvent and, if desired, a thickener, an electrical conductive material, a filler and the like, are added to the negative electrode active material to make a slurry, and the slurry is coated onto a collector, then dried and pressed, whereby the negative electrode can be formed.

In the case of using an alloy-based material, a method of forming a negative electrode active material-containing thin film layer (negative electrode active material layer) by a technique such as vapor deposition, sputtering or plating may be also used.

(Collector)

As the collector for holding the negative electrode active material, a known collector can be arbitrarily used. Examples of the collector of the negative electrode include a metallic material such as aluminum, copper, nickel, stainless steel and nickel-plated steel, and in view of ease of processing and cost, copper is preferred.

Examples of the shape of the collector include, when the collector is a metallic material, a metal foil, a metal cylinder, a metal coil, a metal plate, a metal thin film, an expanded metal, a punching metal, and a metal foam. Among these, a metal thin film is preferred, a copper foil is more preferred, and a rolled copper foil by rolling and an electrolytic copper foil by electrolysis are still more preferred, each of which can be used as the collector.

In view of ensuring of the battery capacity and handleability, the thickness of the collector is usually 1 μm or more, preferably 5 μm or more, and usually 100 μm or less, preferably 50 μm or less.

(Thickness Ratio Between Collector and Negative Electrode Active Material Layer)

The thickness ratio between the collector and the negative electrode active material layer is not particularly limited, but the value of "(thickness of negative electrode active material layer on one surface immediately before injection of nonaqueous electrolyte solution)/(thickness of collector)" is preferably 150 or less, more preferably 20 or less, still more preferably 10 or less, and preferably 0.1 or more, more preferably 0.4 or more, still more preferably 1 or more. When the thickness ratio between the collector and the negative electrode active material layer is in the ranges above, the battery capacity can be maintained and at the same time, heat generation of the collector during high current density charging/discharging can be suppressed.

(Binding Material (Binder))

The binder for binding the negative electrode active material is not particularly limited as long as it is a material stable to the nonaqueous electrolyte solution or the solvent used at the electrode production.

Specific examples thereof include:

a resin-based polymer such as polyethylene, polypropylene, polyethylene terephthalate, polymethyl methacrylate, aromatic polyamides, cellulose and nitrocellulose;

a rubbery polymer such as SBR (styrene•butadiene rubber), isoprene rubber, butadiene rubber, fluororubber, NBR (acrylonitrile•butadiene rubber) and ethylene•propylene rubber;

a styrene•butadiene•styrene block copolymer and a hydrogenation product thereof;

a thermoplastic elastomeric polymer such as EPDM (ethylene•propylene•diene terpolymer), styrene•ethylene•butadiene•styrene copolymer, styrene•soprene•styrene block copolymer and hydrogenation product thereof;

a soft resinous polymer such as syndiotactic 1,2-polybutadiene, polyvinyl acetate, ethylene•vinyl acetate copolymer and propylene•α-olefin copolymer;

a fluorine-based polymer such as polyvinylidene fluoride, polytetrafluoroethylene, fluorinated polyvinylidene fluoride and polytetrafluoroethylene•ethylene copolymer; and a polymer composition having ion conductivity of an alkali metal ion (particularly, lithium ion).

One of these may be used alone, or two or more thereof may be used in any combination in an arbitrary ratio.

The ratio of the binder to the negative electrode active material is preferably 0.1 mass % or more, more preferably 0.5 mass % or more, still more preferably 0.6 mass % or more, and preferably 20 mass % or less, more preferably 15 mass % or less, still more preferably 10 mass % or less, yet still more preferably 8 mass % or less.

When the ratio of the binder to the negative electrode active material is in the ranges above, the battery capacity and the strength of the negative electrode can be sufficiently ensured.

Particularly, in the case of containing a rubbery polymer typified by SBR as a major component, the ratio of the binder to the negative electrode active material is usually 0.1 mass % or more, preferably 0.5 mass % or more, more preferably 0.6 mass % or more, and usually 5 mass % or less, preferably 3 mass % or less, more preferably 2 mass % or less.

Also, in the case of containing a fluorine-based polymer typified by polyvinylidene fluoride as a major component, the ratio to the negative electrode active material is usually 1 mass % or more, preferably 2 mass % or more, more preferably 3 mass % or more, and usually 15 mass % or less, preferably 10 mass % or less, more preferably 8 mass % or less.

(Solvent for Slurry Formation)

The solvent for forming a slurry is not particularly limited in its kind as long as it is a solvent capable of dissolving or dispersing a negative electrode active material and a binder as well as a thickener and an electrically conductive material which are used, if desired, and either an aqueous solvent or a nonaqueous solvent may be used.

Examples of the aqueous solvent include water and alcohol. Examples of the nonaqueous solvent include N-methylpyrrolidone (NMP), dimethylformamide, dimethylacetamide, methyl ethyl ketone, cyclohexanone, methyl acetate, methyl acrylate, diethyltriamine, N,N-dimethylaminopropylamine, tetrahydrofuran (THF), toluene, acetone, diethyl ether, hexamethylphosphoramide, dimethyl sulfoxide, benzene, xylene, quinoline, pyridine, methylnaphthalene, and hexane.

Particularly, in the case of using an aqueous solvent, it is preferred to incorporate a dispersant or the like together with a thickener and make a slurry by using a latex such as SBR. One of these solvents may be used alone, or two or more thereof may be used in any combination in an arbitrary ratio.

(Thickener)

A thickener is usually used so as to adjust the viscosity of the slurry. The thickener is not particularly limited, but specific examples thereof include carboxymethyl cellulose, methyl cellulose, hydroxymethyl cellulose, ethyl cellulose, polyvinyl alcohol, oxidized starch, phosphorylated starch, casein, and salts of these. One of these thickeners may be used alone, or two or more thereof may be used in any combination in an arbitrary ratio.

In the case of further using a thickener, the ratio of the thickener to the negative electrode active material is usually 0.1 mass % or more, preferably 0.5 mass % or more, more preferably 0.6 mass % or more, and usually 5 mass % or less, preferably 3 mass % or less, more preferably 2 mass % or less. When the ratio of the thickener to the negative electrode active material is in the ranges above, a decrease in the battery capacity or an increase in the resistance can be suppressed and at the same time, good coatability can be ensured.

(Electrode Density)

The electrode structure when the negative electrode active material is formed into an electrode is not particularly limited, but the density of the negative electrode active material present on the collector is preferably 1 g·cm$^{-3}$ or more, more preferably 1.2 g·cm$^3$ or more, still more preferably 1.3 g·cm$^{-3}$ or more, and preferably 2.2 g·cm$^{-3}$ or less, more preferably 2.1 g·cm$^{-3}$ or less, still more preferably 2.0 g·cm$^{-3}$ or less, yet still more preferably 1.9 g·cm$^{-3}$ or less.

When the density of the negative electrode active material present on the collector is in the ranges above, not only the negative electrode active material particle can be prevented from breakage, making it possible to suppress worsening of the high current density charge/discharge characteristics due to a rise in the initial irreversible capacity or a drop in the permeability of the nonaqueous electrolyte solution near the collector/negative electrode active material interface, but also a decrease in the battery capacity or an increase in the resistance can be suppressed.

(Thickness of Negative Electrode Plate)

The thickness of the negative electrode plate is designed in accordance with the positive electrode plate used and is not particularly limited, but the thickness of the mixture layer after subtracting the thickness of the metal foil serving as the core is usually 15 µm or more, preferably 20 µm or more, more preferably 30 µm or more, and usually 300 µm or less, preferably 280 µm or less, more preferably 250 µm or less.

(Surface Coating of Negative Electrode Plate)

A negative electrode plate having deposited on the surface thereof a substance differing in the composition from the electrode plate may be also used. Examples of the surface deposition substance include an oxide such as aluminum oxide, silicon oxide, titanium oxide, zirconium oxide, magnesium oxide, calcium oxide, boron oxide, antimony oxide and bismuth oxide; a sulfate such as lithium sulfate, sodium sulfate, potassium sulfate, magnesium sulfate, calcium sulfate and aluminum sulfate; and a carbonate such as lithium carbonate, calcium carbonate and magnesium carbonate.

2-2. Positive Electrode

<Positive Electrode Active Material>

The positive electrode active material used for the positive electrode is described below.

(Composition)

The positive electrode active material is not particularly limited as long as it is a material capable of electrochemically occluding•releasing a lithium ion, but, for example, a substance containing lithium and at least one transition metal is preferred. Specific examples thereof include a lithium-transition metal composite oxide and a lithium-containing transition metal phosphate compound.

Preferred examples of the transition metal in the lithium-transition metal composite oxide include V, Ti, Cr, Mn, Fe, Co, Ni and Cu, and specific examples thereof include:

a lithium•cobalt composite oxide such as $LiCoO_2$, a lithium•nickel composite oxide such as $LiNiO_2$, a lithium•manganese composite oxide such as $LiMnO_2$, $LiMn_2O_4$ and $Li_2MnO_4$, and an oxide where a part of transition metal atoms as the main constituent of the lithium-transition metal composite oxide above is replaced by another element such as Na, K, B, F, Al, Ti, V, Cr, Mn, Fe, Co, Li, Ni, Cu, Zn, Mg, Ga, Zr, Si, Nb, Mo, Sn and W.

Specific examples of the oxide formed by partial replacement include $LiNi_{0.5}Mn_{0.5}O_2$, $LiNi_{0.85}Co_{0.10}Al_{0.05}O_2$, $LiNi_{0.33}Co_{0.33}Mn_{0.33}O_2$, $LiNi_{0.45}Co_{0.10}Al_{0.45}O_2$, $LiMn_{1.8}Al_{0.2}O_4$, and $LiMn_{1.5}Ni_{0.5}O_4$.

The transition metal in the lithium-containing transition metal phosphate compound is preferably, for example, V, Ti, Cr, Mn, Fe, Co, Ni or Cu. Specific examples of the compound include iron phosphates such as $LiFePO_4$, $Li_3Fe_2(PO_4)_3$ and $LiFeP_2O_7$, cobalt phosphates such as $LiCoPO_4$, and a compound where a part of transition metal atoms as the main component of the lithium transition metal phosphate compound above is replaced by another element such as Al, Ti, V, Cr, Mn, Fe, Co, Li, Ni, Cu, Zn, Mg, Ga, Zr, Nb and Si.

Lithium phosphate is preferably incorporated into the positive electrode active material, because continuous charge characteristics are enhanced. Use of lithium phosphate is not limited, but lithium phosphate is preferably used by mixing it with the above-described positive electrode active material. The amount of lithium phosphate used is preferably 0.1 mass % or more, more preferably 0.3 mass % or more, still more preferably 0.5 mass % or more, and preferably 10 mass % or less, more preferably 8 mass % or less, still more preferably 5 mass % or less, based on the total of the positive electrode active material and lithium phosphate.

(Surface Coating)

A positive electrode active material having deposited on the surface thereof a substance differing in the composition from the electrode active material may be also used. Examples of the surface deposition substance include an oxide such as aluminum oxide, silicon oxide, titanium oxide, zirconium oxide, magnesium oxide, calcium oxide, boron oxide, antimony oxide and bismuth oxide; a sulfate such as lithium sulfate, sodium sulfate, potassium sulfate, magnesium sulfate, calcium sulfate and aluminum sulfate; a carbonate such as lithium carbonate, calcium carbonate and magnesium carbonate; and carbon.

The surface deposition substance can be deposited on the surface of the positive electrode active material, for example, by a method where the surface deposition substance is dissolved or suspended in a solvent, added by impregnation to the positive electrode active material, and dried, a method where a surface deposition substance precursor is dissolved or suspended in a solvent, added by impregnation to the positive electrode active material, and reacted by heating or the like, or a method where the surface deposition substance is added to a positive electrode active material precursor and fired at the same time. Incidentally, in the case of depositing carbon, a method of afterward mechanically depositing a carbonaceous substance, for example, in the form of activated carbon may be also used.

The amount of the surface deposition substance is, by mass, preferably 0.1 ppm or more, more preferably 1 ppm or more, still more preferably 10 ppm or more, and preferably 20% or less, more preferably 10% or less, still more preferably 5% or less, based on the positive electrode active material. Thanks to the surface deposition substance, an effect of suppressing an oxidation reaction of the electrolyte solution on the positive electrode active material surface is obtained and the battery life can be enhanced, but if the deposition amount is too small, the effect is not sufficiently brought out, whereas if the deposition amount is too large, the entrance/exit of a lithium ion may be hindered to cause an increase in the interface resistance.

In the present invention, a positive electrode active material having deposited on the surface thereof a substance differing in the composition from the electrode active material is encompassed by the "positive electrode active material".

(Shape)

Examples of the shape of the positive electrode active material particle include a lump, a polyhedron, a sphere, an oval sphere, a plate, a needle, and a column, which are conventionally employed. Also, primary particles may be aggregated to form a secondary particle.

(Tap Density)

The tap density of the positive electrode active material is preferably 0.5 g/cm$^3$ or more, more preferably 0.8 g/cm$^3$ or more, still more preferably 1.0 g/cm$^3$ or more. When the tap density of the positive electrode active material is in the range above, the amount of the dispersion medium necessary for the formation of the positive electrode active material layer or the required amount of the electrically conductive material or binder can be reduced, as a result, the packing ratio of the positive electrode active material and the battery capacity can be ensured.

By using a composite oxide powder having a high tap density, a high-density positive electrode active material layer can be formed. The tap density is preferably higher in general and has no particular upper limit but is preferably 4.0 g/cm$^3$ or less, more preferably 3.7 g/cm$^3$ or less, still more preferably 3.5 g/cm$^3$ or less. Within this range, reduction in the load characteristics can be suppressed.

In the present invention, the tap density is determined as a powder packing density (tap density) g/cc when from 5 to 10 g of the positive electrode active material powder is put in a 10 ml glass-made measuring cylinder and tapped 200 times with a stroke of about 20 mm.

(Median Diameter d50)

The median diameter d50 (when primary particles are aggregated to form a secondary particle, the secondary particle diameter) of the positive electrode active material particle is preferably 0.3 μm or more, more preferably 0.5 μm or more, still more preferably 0.8 μm or more, most preferably 1.0 μm or more, and preferably 30 μm or less, more preferably 27 μm or less, still more preferably 25 μm or less, most preferably 22 μm or less. Within these ranges, a high tap-density product is obtained and not only reduction in the battery performance can be suppressed but also a problem such as streaking at the production of a positive electrode of a battery, that is, at the time of slurrying an active material, an electrically conductive material, a binder and the like with a solvent and coating the slurry in a thin film manner, can be prevented. Here, by mixing two or more kinds of positive electrode active materials different in the median diameter d50, the packing property at the production of a positive electrode can be more enhanced.

In the present invention, the median diameter d50 is measured by a known laser diffraction/scattering particle size distribution measuring apparatus. In the case of employing LA-920 manufactured by HORIBA as the particle size distribution analyzer, the measurement is performed by using an aqueous 0.1 mass % sodium hexametaphosphate solution as the dispersion medium used at the measurement and setting the measurement refractive index to 1.24 after ultrasonic dispersion for 5 minutes.

(Average Primary Particle Diameter)

In the case where primary particles are aggregated to form a secondary particle, the average primary particle diameter of the positive electrode active material is preferably 0.05 μm or more, more preferably 0.1 μm or more, still more preferably 0.2 μm or more, and preferably 5 μm or less, more preferably 4 μm or less, still more preferably 3 μm or less, most preferably 2 μm or less. Within this range, not only the powder packing property and the specific surface area can be ensured to thereby suppress reduction in the battery performance but also appropriate crystallinity is obtained, making it possible to ensure charge/discharge reversibility.

In the present invention, the primary particle diameter is measured by observation using a scanning electron microscope (SEM). Specifically, the longest length value of a section defined by left and right boundary lines of a primary particle with respect to the horizontal straight line is determined on arbitrary 50 particles in a photograph at a magnification of 10,000 times, and the average value thereof is calculated, whereby the primary particle diameter is determined.

(BET Specific Surface Area)

The BET specific surface area of the positive electrode active material is preferably 0.1 m$^2$/g or more, more preferably 0.2 m$^2$/g or more, still more preferably 0.3 m$^2$/g or more, and is 50 m$^2$/g or less, preferably 40 m$^2$/g or less, more preferably 30 m$^2$/g or less. When the BET specific surface area is in the ranges above, the battery performance can be ensured and at the same time, the coatability of the positive electrode active material can be kept good.

In the present invention, the BET specific surface area is defined as a value determined using a surface area meter (for example, a fully automatic surface area measuring apparatus manufactured by Ohkura Riken Co., Ltd.) by preliminarily drying a sample at 150° C. for 30 minutes in a nitrogen gas stream and thereafter, measuring the sample by the nitrogen adsorption BET one-point method in accordance with a gas-flow process flowing a nitrogen-helium mixed gas that is precisely adjusted to give a relative nitrogen pressure value of 0.3 with respect to atmospheric pressure.

(Production Method of Positive Electrode Active Material)

As for the production method of the positive electrode material, a method generally used as the production method of an inorganic compound is used. In particular, for producing a spherical or oval-spherical active material, various methods may be considered, and examples thereof include a method where the raw material of the transition metal is dissolved or pulverized/dispersed in a solvent such as water, the pH is adjusted with stirring to produce and recover a spherical precursor, and the spherical precursor is dried, if desired, and after addling an Li source such as LiOH, Li$_2$CO$_3$ and LiNO$_3$, fired at a high temperature to obtain the active material.

For the production of the positive electrode, the above-described positive electrode active material may be used alone, or one or more kinds differing in the composition may be used together in any combination in arbitrary ratio. In this case, the preferred composition is a combination of LiCoO$_2$ with LiMn$_2$O$_4$ or the material where a part of Mn is replaced by another transition metal or the like (for example, LiNi$_{0.33}$Co$_{0.33}$Mn$_{0.33}$O$_2$), or a combination with LiCoO$_2$ or the material where a part of Co is replaced with another transition metal or the like.

<Configuration and Production Method of Positive Electrode>

The configuration of the positive electrode is described below. In the present invention, the positive electrode can be produced by forming, on a collector, a positive electrode active material layer containing a positive electrode active material and a binder. The production of the positive electrode using a positive electrode active material can be performed in a conventional manner. That is, a positive electrode active material layer is formed on a collector by dry mixing a positive electrode active material, a binder and, if desired, an electrically conductive material, a thickener and the like, forming the mixture into a sheet, and pressure-bonding the sheet against a positive electrode collector, or by dissolving or dispersing these materials in a liquid medium to make a slurry and coating and drying the slurry on a positive electrode collector, and a positive electrode can be thus obtained.

The content of the positive electrode active material in the positive electrode active material layer is preferably 80 mass % or more, more preferably 82 mass % or more, still more preferably 84 mass % or more, and preferably 99 mass % or less, more preferably 98 mass % or less. Within these ranges, the electric capacity of the positive electrode active material in the positive electrode active material layer can be ensured and at the same time, the strength of the positive electrode can be maintained.

The positive electrode active material layer obtained by coating and drying is preferably compacted with a hand press, a roller press or the like so as to raise the packing density of the positive electrode active material. The density of the positive electrode active material layer is preferably 1.5 g/cm$^3$ or more, more preferably 2 g/cm$^3$, still more preferably 2.2 g/cm$^3$ or more, and preferably 5 g/cm$^3$ or less, more preferably 4.5 g/cm$^3$ or less, still more preferably 4 g/cm$^3$ or less. Within these ranges, good charge/discharge characteristics are obtained and at the same time, an increase in the electric resistance can be suppressed.

(Electrically Conductive Material)

As the electrically conductive material, any known electrically conductive material can be used. Specific examples thereof include a metallic material such as copper and nickel; a graphite such as natural graphite and artificial graphite; a carbon black such as acetylene black; and a carbon material such as amorphous carbon, e.g., needle coke. One of these may be used alone, or two or more thereof may be used together in any combination in an arbitrary ratio. The electrically conductive material is used such that the content thereof in the positive electrode active material layer is usually 0.01 mass % or more, preferably 0.1 mass % or more, more preferably 1 mass % or more, and usually 50 mass % or less, preferably 30 mass % or less, more preferably 15 mass % or less. Within these ranges, the electrical conductivity and the battery capacitance can be sufficiently ensured.

(Binder)

The binder for use in the production of the positive electrode active material layer is not particularly limited, and in the case of a coating method, the binder may suffice if it is a material capable of being dissolved or dispersed in the liquid medium used at the electrode production, but specific examples thereof include:

a resin-based polymer such as polyethylene, polypropylene, polyethylene terephthalate, polymethyl methacrylate, polyimide, aromatic polyamide, cellulose and nitrocellulose;

a rubbery polymer such as SBR (styrene-butadiene rubber), NBR (acrylonitrile-butadiene rubber), fluororubber, isoprene rubber, butadiene rubber and ethylene-propylene rubber;

a thermoplastic elastomeric polymer such as styrene•butadiene•styrene block copolymer or its hydrogenation product, EPDM (ethylene•propylene•diene terpolymer), styrene•ethylene•butadiene•ethylene copolymer, and styrene•isoprene•styrene block copolymer or its hydrogenation product;

a soft resinous polymer such as syndiotactic 1,2-polybutadiene, polyvinyl acetate, ethylene•vinyl acetate copolymer and propylene•α-olefin copolymer;

a fluorine-based polymer such as polyvinylidene fluoride (PVdF), polytetrafluoroethylene, fluorinated polyvinylidene fluoride and polytetrafluoroethylene•ethylene copolymer; and a polymer composition having ionic conductivity of an alkali metal ion (particularly, lithium ion).

One of these substances may be used alone, or two or more thereof may be used together in any combination in an arbitrary ratio.

The proportion of the binder in the positive electrode active material layer is usually 0.1 mass % or more, preferably 1 mass % or more, more preferably 1.5 mass % or more, and usually 80 mass % or less, preferably 60 mass % or less, more preferably 40 mass % or less, most preferably 10 mass % or less. If the proportion of the binder is too low, there may occur a case where the positive electrode active material cannot be sufficiently held and this causes a lack of mechanical strength of the positive electrode and in turn, a worsening of the battery performance such as cycle characteristics. On the other hand, if the proportion is too high, this may lead to reduction in the battery capacity or electrical conductivity.

(Solvent for Slurry Formation)

The solvent for forming a slurry is not particularly limited in its kind as long as it is a solvent capable of dissolving or dispersing a positive electrode active material, an electrically conductive material and a binder as well as a thickener which is used, if desired, and either an aqueous solvent or a nonaqueous solvent may be used. Examples of the aqueous solvent include water and a mixed solvent of alcohol and water. Examples of the organic solvent include:

aliphatic hydrocarbons such as hexane;

aromatic hydrocarbons such as benzene, toluene, xylene and methylnaphthalene;

heterocyclic compounds such as quinoline and pyridine;

ketones such as acetone, methyl ethyl ketone and cyclohexanone;

esters such as methyl acetate and methyl acrylate;

amines such as diethylenetriamine and N,N-dimethylaminopropylamine;

ethers such as diethyl ether, propylene oxide and tetrahydrofuran (THF);

amides such as N-methylpyrrolidone (NMP), dimethylformamide and dimethylacetamide; and aprotic polar solvents such as hexamethylphosphoramide and dimethyl sulfoxide.

Particularly, in the case of using an aqueous solvent, the slurry is preferably formed using a thickener and a latex such as styrene-butadiene rubber (SBR). The thickener is usually used so as to regulate the viscosity of the slurry. The thickener is not particularly limited, but specific examples thereof include carboxymethyl cellulose, methyl cellulose, hydroxymethyl cellulose, ethyl cellulose, polyvinyl alcohol, oxidized starch, phosphorylated starch, casein, and salts of these. One of these thickeners may be used alone, or two or more thereof may be used together in any combination in an arbitrary ratio. In the case of further adding a thickener, the ratio of the thickener to the active material is 0.1 mass % or more, preferably 0.2 mass % or more, more preferably 0.3 mass % or more, and is 5 mass % or less, preferably 3 mass % or less, more preferably 2 mass % or less. Within these ranges, good coatability is obtained and at the same time, a decrease in the battery capacity or an increase in the resistance can be suppressed.

(Collector)

The material of the positive electrode collector is not particularly limited, and any known material can be used. Specific examples thereof include a metallic material such as aluminum, stainless steel, nickel-plated metal, titanium and tantalum; and a carbon material such as carbon cloth and carbon paper. Among these, a metallic material is preferred, and aluminum is more preferred.

Examples of the shape of the collector include: in the case of a metallic material, a metal foil, a metal cylinder, a metal coil, a metal plate, a thin metal film, an expanded metal, a punching metal, and a metal foam; and in the case of a carbon material, a carbon plate, a carbon thin film, and a carbon cylinder. Among these, a metal thin film is preferred. The thin film may be appropriately formed into a mesh. The thickness of the thin film may be arbitrary, but in view of strength as a collector and handleability, the thickness is usually 1 μm or more, preferably 3 μm or more, more preferably 5 μm or more, and usually 1 mm or less, preferably 100 μm or less, more preferably 50 μm or less.

From the standpoint of reducing the electron contact resistance between the collector and the positive electrode active material layer, it is also preferred that an electrically conductive aid is coated on the surface of the collector. Examples of the electrically conductive aid include carbon and noble metals such as gold, platinum and silver.

The thickness ratio between the collector and the positive electrode active material layer is not particularly limited, but the value of (thickness of positive electrode active material layer on one surface immediately before injection of electrolyte solution)/(thickness of collector) is preferably 20 or less, more preferably 15 or less, most preferably 10 or less, and preferably 0.5 or more, more preferably 0.8 or more, most preferably 1 or more. If the thickness ratio exceeds the range above, the collector may generate heat due to Joule heat during high current density charging/discharging. Within the ranges above, the collector can be prevented from heat generation during high current density charging/discharging, and the battery capacity can be ensured.

(Electrode Area)

In the case of using the nonaqueous electrolyte solution of the present invention, from the standpoint of enhancing the stability during high-output high-temperature operation, the area of the positive electrode active material layer is preferably made larger than the outer surface area of the battery outer case. Specifically, the sum of electrode areas of the positive electrode is preferably made to be, in terms of the area ratio, 15 times or more, more preferably 40 times or more, larger than the surface area of the outer case of the secondary battery.

The outer surface area of the outer case indicates, in the case of having a bottomed square shape, the total area calculated from the height, width and thickness of the case in the portion filled with power generation elements, exclusive of the protruding portion of a terminal; and in the case of having a bottomed cylindrical shape, the geometric surface area determined by approximating the case in the portion filled with power generation elements, exclusive of the protruding portion of a terminal, to a cylinder.

The sum of electrode areas of the positive electrode indicates the geometric surface area of a positive electrode mixture layer opposing a negative electrode active material-containing mixture layer and in the case of a structure where a positive electrode mixture layer is formed on both surfaces through a collector foil, indicates the sum of areas separately calculated for each surface.

(Thickness of Positive Electrode Plate)

The thickness of the positive electrode plate is not particularly limited, but in view of high capacity and high output, the thickness of the mixture layer after subtracting the thickness of the metal foil serving as the core is, per one surface of the collector, preferably 10 μm or more, more preferably 20 μm or more, and preferably 500 μm or less, more preferably 450 μm or less.

(Surface Coating of Positive Electrode Plate)

A positive electrode plate having deposited on the surface thereof a substance differing in the composition from the electrode plate may be also used. Examples of surface deposition substance include an oxide such as aluminum oxide, silicon oxide, titanium oxide, zirconium oxide, magnesium oxide, calcium oxide, boron oxide, antimony oxide and bismuth oxide; a sulfate such as lithium sulfate, sodium sulfate, potassium sulfate, magnesium sulfate, calcium sulfate and aluminum sulfate; a carbonate such as lithium carbonate, calcium carbonate and magnesium carbonate; and carbon.

2-3. Separator

Usually, a separator is caused to intervene between the positive electrode and the negative electrode so as to prevent a short-circuit. In this case, the separator is usually impregnated with the nonaqueous electrolyte solution of the present invention.

The material and shape of the separator are not particularly limited, and any known material or shape can be employed as long as the effects of the present invention are not seriously impaired. Among others, a resin, a glass fibers, an inorganic material or the like each formed of a material stable to the nonaqueous electrolyte solution of the present invention is used, and it is preferred to use a thing, for example, in the form of a porous sheet or a nonwoven fabric, which are excellent in liquid retentivity.

Examples of the material of the resin or glass fiber separator, which can be used, include a polyolefin such as polyethylene and polypropylene, an aromatic polyamide, polytetrafluoroethylene, polyether sulfone, and a glass filters. Among these, a glass filter and a polyolefin are preferred, and a polyolefin is more preferred. One of these materials may be used alone, or two or more thereof may be used together in any combination in an arbitrary ratio.

The thickness of the separator may be arbitrary but is usually 1 μm or more, preferably 5 μm or more, more preferably 8 μm or more, and usually 50 μm or less, preferably 40 μm or less, more preferably 30 μm or less. Within these ranges, the insulating property and mechanical strength can be ensured and at the same time, the battery performance such as rate characteristic as well as the energy density can be ensured.

In the case of using a porous separator such as porous sheet and nonwoven fabric, the porosity of the separator may be arbitrary but is usually 20% or more, preferably 35% or more, more preferably 45% or more, and usually 90% or less, preferably 85% or less, more preferably 75% or less. When the porosity is in these ranges, the insulating property and mechanical strength can be ensured and at the same time, good rate characteristics with reduced membrane resistance can be obtained.

The average pore diameter of the separator may be also arbitrary but is usually 0.5 μm or less, preferably 0.2 μm or less, and usually 0.05 μm or more. If the average pore diameter exceeds the range above, a short-circuit is likely to occur. When the average pore diameter is in the ranges above, good rate characteristics with reduced membrane resistance can be obtained while preventing a shirt-circuit. On the other hand, as the inorganic material, for example, an oxide such as alumina and silicon dioxide, a nitride such as aluminum nitride and silicon nitride, or a sulfate such as barium sulfate and calcium sulfate, is used, and a particle-shaped or fiber-shaped material is used.

As for the form of the separator, a separator in the thin film form, such as nonwoven fabric, woven fabric and micro-porous film, is used. In the case of a thin film form, a thin film separator having a pore diameter of 0.01 to 1 μm and a thickness of 5 to 50 μm is suitably used.

Other than the independent thin film, a separator obtained by forming a composite porous layer containing particles of the above-described inorganic material as the surface layer of the positive electrode and/or the negative electrode with use of a resin-made binder, may be used. For example, a porous layer containing alumina particles having a 90% particle diameter of less than 1 μm may be formed on both surfaces of the positive electrode by using a fluororesin as the binder.

2-4. Battery Design

<Electrode Group>

The electrode group may have either a stacked structure where the above-described separator is interposed between the positive electrode plate and the negative electrode plate, or a structure where the positive electrode plate and the negative electrode plate are spirally wound with the above-described separator interposed therebetween. The proportion of the volume of the electrode group in the internal volume of the battery (hereafter, referred to as electrode group occupancy) is usually 40% or more, preferably 50% or more, and usually 90% or less, preferably 80% or less.

When the electrode group occupancy is in the ranges above, not only the battery capacity can be ensured but also the charge/discharge repetition performance and the characteristics such as high-temperature storage can be kept from deterioration due to an increase in the internal pressure and furthermore, operation of a gas release valve can be prevented.

<Collector Structure>

The collector structure is not particularly limited, but it is preferred to take a structure capable of reducing the resistance of the wiring portion or joint portion.

In the case where the electrode group has the stacked structure described above, a structure formed by bundling metal core portions of respective electrode layers and welding the bundle to a terminal is suitably used. When the electrode area of one sheet is large, the internal resistance increases. Therefore, a method of providing a plurality of terminals in the electrode and thereby reducing the resistance is also suitably used. In the case of an electrode group having the wound structure described above, the internal resistance can be reduced by providing a plurality of lead structures for each of the positive electrode and the negative electrode and bundling them into a terminal.

<Outer Case>

The material of the outer case is not particularly limited as long as it is a substance stable to the nonaqueous electrolyte solution used. Specifically, metals such as nickel-plated steel plate, stainless steel, aluminum, aluminum alloy and magnesium alloy, and a laminated film (laminate film) of a resin and an aluminum foil, are used. In view of reduction in the weight, a metal such as aluminum and aluminum alloy, and a laminate film are suitably used.

The outer case using metals includes those having a hermetically sealed structure formed by welding metals together by means of laser welding, resistance welding or ultrasonic welding, and those having a caulk structure formed by using the above-described metals via a resin-made gasket.

The outer case using the laminate film include, for example, those having a hermetically sealed structure formed by heat-sealing resin layers together. In order to enhance the sealing property, a resin different from the resin used for the laminate film may be interposed between the resin layers. Particularly, in the case of forming a hermetic structure by heat-sealing resin layers together through a collector terminal, because of jointing between a metal and a resin, a resin having a polar group or a modified resin having introduced thereinto a polar group is suitably used as the resin interposed. The shape of the housing case is also arbitrary and may be any of, for example, a cylindrical form, a prismatic form, a laminate form, a coin form and a large form.

<Protective Element>

For example, a PTC (Positive Temperature Coefficient) capable of increasing the resistance upon occurrence of abnormal heat generation or excessive current flow, a temperature fuse, a thermister, and a valve (current shutoff valve) for blocking the current flowing in the circuit due to an abrupt rise in the internal pressure or internal temperature of the battery upon occurrence of abnormal heat generation can be used as the protective element.

As for the protective element, those satisfying the condition that the element does not work in normal use of high current are preferably selected, and it is more preferred to design a battery free from abnormal heat generation or thermal runaway even without a protective element.

3. Synthesis Method of Compound

The sulfonic acid ester of the present invention is not limited in its production process but, for example, can be synthesized by adding a base such as triethylamine to a solution containing 2-chloroethanesulfonyl chloride and an alcohol such as 2-propin-1-ol and ethylene glycol, and allowing the reaction to proceed.

The base used for the synthesis reaction above may be arbitrary as long as the sulfonic acid ester of the present invention can be obtained, but, for example, triethylamine, tributylamine, pyridine and 2-6-lutidine can be used. As for the base, one kind may be used alone, or two or more kinds may be used together in any combination in an arbitrary ratio.

The synthesis reaction above is preferably performed in a reaction solvent. The reaction solvent used may be arbitrary as long as the sulfonic acid ester of the present invention can be obtained, but, for example, dichloromethane, chloroform and tetrahydrofuran can be used. As for the reaction solvent, one kind may be used alone, or two or more kinds may be used together in any combination in an arbitrary ratio.

The reaction temperature in the synthesis reaction above may be also arbitrary as long as the sulfonic acid ester of the present invention can be obtained, but the reaction temperature is usually −30° C. or more and usually 100° C. or less, preferably 80° C. or less, more preferably 50° C. or less. If the reaction temperature is less than the lower limit above, the reaction rate may be reduced to require a long reaction time, whereas if the reaction temperature exceeds the upper limit, alcohols used for the reaction may escape from the system. Particularly, in the case of adding dropwise a base such as triethylamine, the temperature is preferably kept at 40° C. or less.

The reaction time in the synthesis reaction above may be also arbitrary as long as the sulfonic acid ester of the present invention can be obtained, but the reaction time is usually 30 minutes or more, preferably 1 hour or more, and usually 48 hours or less, preferably 24 hours or less, more preferably 12 hours or less. If the reaction time is less than the lower limit above, the reaction may not be completed, giving rise to a decrease in the yield, whereas if the reaction time exceeds the upper limit, a decomposition reaction of the sulfonic acid ester due to excess base may occur in the system to cause a decrease in the yield of the target compound.

The ratio between 2-chloroethanesulfonyl chloride and alcohol as raw materials used in the synthesis reaction above may be also arbitrary as long as the sulfonic acid ester of the present invention can be obtained, but it is preferred to set the ratio therebetween such that the ratio represented by "(molar amount of 2-chloroethanesulfonyl chloride)/(amount of alcohol)" is usually 0.7 or more, preferably 0.8 or more, more preferably 0.9 or more, and usually 1.3 or less, preferably 1.2 or less, more preferably 1.1 or less. If the ratio deviates from this range, the raw material may remain unreacted to cause a decrease in the yield.

Also, the ratio between 2-chloroethanesulfonyl chloride and base as raw materials may be also arbitrary as long as the sulfonic acid ester of the present invention can be obtained, but it is preferred to set the ratio therebetween such that the ratio represented by "(molar amount of 2-chloroethanesulfonyl chloride)/(base)" is usually 0.3 or more, preferably 0.4 or more, and usually 0.7 or less, preferably 0.6 or less. If the ratio is less than the lower limit above, a decomposition reaction of the sulfonic acid ester due to excess base occurs in the system to cause a decrease in the yield of the target compound, whereas if the ratio exceeds the upper limit, the reaction may not be completed, giving rise to a decrease in the yield of the target compound.

Furthermore, the product obtained in the synthesis reaction above is usually purified to obtain the sulfonic acid ester of the present invention. At this time, the method for purification is not limited and may be arbitrary, but, for example, distillation purification can be used.

EXAMPLES

The present invention is described in greater detail below by referring to Examples and Comparative Examples, but the present invention is not limited to these Examples.

Unsaturated sulfonic acid esters used in Examples are illustrated below.

[Chem. 21]

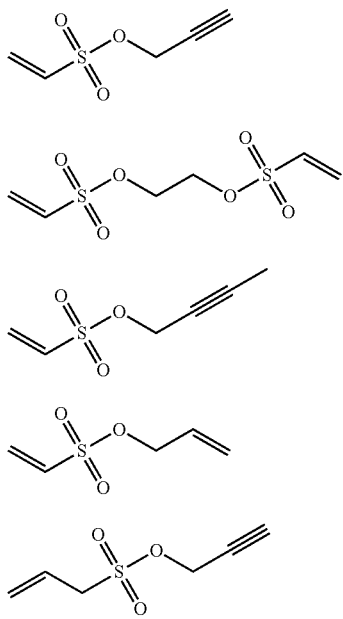

Also, sulfonic acid esters used in Comparative Examples are illustrated below.

[Chem. 22]

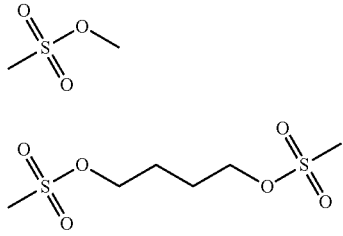

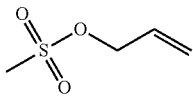 (viii)

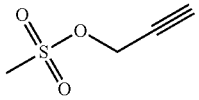 (ix)

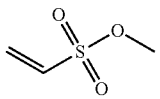 (x)

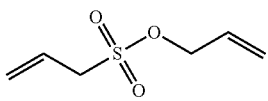 (xi)

Synthesis Example A

Synthesis of Compound (i)

Under ice cooling, 62.1 g of triethylamine was slowly added dropwise to a dichloromethane solution containing 50 g of 2-chloroethanesulfonyl chloride and 18.9 g of 2-propin-1-ol, followed by stirring. After removing the produced precipitate by filtration, the obtained liquid was distilled to synthesize Compound (i) (vinylsulfonic acid ester) represented by formula (i).

Analysis results by $^1$H-NMR, $^{13}$C-NMR and GC-MS are shown below.

$^1$H-NMR δ (ppm) in CDCl$_3$:
2.65-2.66 (m, 1H, —C≡CH),
4.78 (s, 2H, —CH$_2$—C≡CH),
6.15-6.48 (m, 2H, CH$_2$=CH—),
6.59-6.66 (m, 1H, CH$_2$=CH—).

$^{13}$C-NMR δ (ppm) in CDCl$_3$:
57.69 (s, 1C, O—C, —C≡C),
75.55 (s, 1C, —C—C≡C),
77.85 (s, 1C, —C—C≡C),
130.62 (s, 1C, C=C—),
132.90 (s, 1C, C=C—).

GC-MS m/z: 147 [M+H$^+$]$^+$

*$^1$H-NMR: Hydrogen of tetramethylsilyl as the internal standard was 0.00 ppm.

*$^{13}$C-NMR: Carbon of protio-chloroform as the internal standard was set at 77.16 ppm.

Synthesis Example B

Synthesis of Compound (ii)

Under ice cooling, 21.8 g of triethylamine was slowly added dropwise to a dichloromethane solution containing 16.3 g of 2-chloroethanesulfonyl chloride and 3.1 g of ethylene glycol, followed by stirring. After removing the produced precipitate by filtration, the obtained liquid was distilled to synthesize Compound (ii) (bis(vinylsulfonic acid ester)) represented by formula (ii).

Analysis results by $^1$H-NMR, $^{13}$C-NMR and GC-MS are shown below.

$^1$H-NMR δ (ppm) in CDCl$_3$:
4.35 (s, 4H, O—CH$_2$—CH$_2$—O),
6.20-6.48 (m, 4H, CH$_2$=CH—), 6.56-6.66 (m, 2H, CH$_2$=C$\underline{H}$—).
$^{13}$C-NMR δ (ppm) in CDCl$_3$:
67.43 (s, 2C, O—$\underline{C}$—$\underline{C}$—O),
131.46 (s, 2C, $\underline{C}$=C—),
131.94 (s, 2C, C=$\underline{C}$—).
GC-MS m/z: 243 [M+H$^+$]$^+$
$^1$H-NMR: Hydrogen of tetramethylsilyl as the internal standard was 0.00 ppm.
$^{13}$C-NMR: Carbon of protio-chloroform as the internal standard was set at 77.16 ppm.

Synthesis Example C

Synthesis of Compound (iii)

Compound (iii) was synthesized by the same synthesis method as in Synthesis Example A except for using 23.6 g of 2-butin-1-ol in place of 18.9 g of 2-propion-1-ol.

Synthesis Example D

Synthesis of Compound (iv)

Compound (iv) was synthesized by the same synthesis method as in Synthesis Example A except for using 19.6 g of allyl alcohol in place of 18.9 g of 2-propion-1-ol.

Synthesis Example E

Synthesis of Compound (v)

Under ice cooling, 31.0 g of triethylamine was slowly added dropwise to a dichloromethane solution containing 43.1 g of allylsulfonyl chloride and 18.9 g of 2-propin-1-ol, followed by stirring. After removing the produced precipitate by filtration, the obtained liquid was distilled to synthesize Compound (v).

Synthesis Example F

Synthesis of Compound (viii)

Compound (viii) was synthesized by the same synthesis method as in Synthesis Example D except for using 35.1 g of methanesulfonyl chloride in place of 43.1 g of allylsulfonyl chloride.

Synthesis Example E

Synthesis of Compound (ix)

Compound (ix) was synthesized by the same synthesis method as in Synthesis Example F except for using 18.9 g of 2-propin-1-ol in place of 19.6 g of allyl alcohol.

Synthesis Example H

Synthesis of Compound (x)

Compound (x) was synthesized by the same synthesis method as in Synthesis Example A except for using 10.8 g of methyl alcohol in place of 18.9 g of 2-propion-1-ol.

Synthesis Example I

Synthesis of Compound (xi)

Compound (xi) was synthesized by the same synthesis method as in Synthesis Example E except for using 19.6 g of allyl alcohol in place of 18.9 g of 2-propion-1-ol.

Examples 1 to 6 and Comparative Examples 1 to 7

Battery Evaluation

[Preparation of Nonaqueous Electrolyte Solution]

In a dry argon atmosphere, dried LiPF$_6$ was dissolved in a mixture of monofluoroethylene carbonate (MFEC) and dimethyl carbonate (DMC) (volume ratio: 30:70) to account for a proportion of 1 mol/L, whereby an electrolyte solution base was prepared. To this electrolyte solution base, the compound was added in a ratio shown in Table 1 to prepare electrolyte solutions used in Examples 1 to 6 and Comparative Examples 1 to 7.

Here, Compounds (i) to (v), (viii), (x) and (xi) were synthesized by the procedure above, and Compounds (vi) and (vii) were obtained as commercial products from Tokyo Chemical Industry Co., Ltd.

[Production of Positive Electrode]

In an N-methylpyrrolidone solvent, 97 mass % of lithium cobaltate (LiCoO$_2$) as a positive electrode active material, 1.5 mass % of acetylene black as an electrically conductive material and 1.5 mass % of polyvinylidene fluoride (PVdF) as a binder were mixed by means of a disperser to make a slurry. This slurry was uniformly coated on both surfaces of a 21 μm-thick aluminum foil, then dried and pressed to produce a positive electrode.

[Production of Negative Electrode]

1 Part by mass of an aqueous dispersion of sodium carboxymethyl cellulose (concentration of sodium carboxymethyl cellulose: 1 mass %) as a thickener and 1 part by mass of an aqueous dispersion of styrene-butadiene rubber (concentration of styrene-butadiene rubber: 50 mass %) as a binder were added to 100 parts by mass of graphite powder as a negative electrode active material and mixed by means of a disperser to make a slurry. This slurry was uniformly coated on one surface of a 12 μm-thick copper foil, then dried and pressed to produce a negative electrode.

[Production of Secondary Battery]

The positive and negative electrodes produced above and a polyethylene-made separator were stacked in order of negative electrode, separator, positive electrode, separator and negative electrode to produce a battery element. This battery element was inserted into a bag composed of a laminate film of aluminum (thickness: 40 μm) and resin layers coated on both surfaces of alumina, while protrudingly providing positive and negative electrode terminals and thereafter, the nonaqueous electrolyte solution was poured into the bag. The bag was then vacuum-sealed to produce a nonaqueous electrolyte battery.

[Evaluation of Initial Capacity]

The nonaqueous electrolyte battery in the state of being sandwiched and pressed between glass plates was, at 25° C., charged to 4.1 V at a constant current corresponding to 0.2 C and discharged to 3 V at a 0.2 C constant current. Furthermore, the battery was charged to 4.33 V in a constant current-constant voltage mode at a current corresponding to 0.2 C (hereinafter, sometimes referred to as "CCCV charging") (0.05 C cut), then discharged to 3 V at 0.2 C and stabilized. Subsequently, the battery was subjected to CCCV charging (0.05 C cut) to 4.33 V at 0.2 C and again discharged to 3 V at 0.2 C to determine the initial discharge capacity.

Here, Here, 1 C means a current value at which the reference capacity of the battery is discharged over 1 hour. For example, 0.2 C is ⅕ the current value.

[Evaluation of High-Temperature Storage Characteristics]

The nonaqueous electrolyte battery after the evaluation of initial capacity was subjected to CCCV charging (0.05 C cut) to 4.33 V at 0.2 C at 45° C. and then to high-temperature storage under the conditions of 85° C. and 24 hours. The battery was sufficiently cooled and then measured for the volume by dipping it in an ethanol bath, and the amount of gas evolved was determined from the change in voltage between before and after the storage. Subsequently, the battery was discharged to 3 V at 0.2 C at 25° C. and measured for the residual capacity after the evaluation of high-temperature storage characteristics, and the ratio of residual capacity to initial discharge capacity was determined and taken as the residual capacity (%) after high-temperature storage. Again, the battery was subjected to CCCV charging (0.05 C cut) to 4.33 V at 0.2 C, then discharged to 3 V at 0.2 C and measured for the 0.2 C discharge capacity, and the ratio of 0.2 C discharge capacity to initial discharge capacity was determined and taken as the recovery capacity (%) after high-temperature storage.

Using these nonaqueous electrolyte batteries, evaluation of high-temperature storage characteristics was performed. Evaluation results are shown in Table 1.

Examples 7 to 14 and Comparative Examples 8 to 10

Battery Evaluation

[Preparation of Nonaqueous Electrolyte Solution]

In a dry argon atmosphere, 1 mass % of succinonitrile, in terms of the content in the nonaqueous solution, was mixed with a mixture of MFEC, ethylene carbonate (EC) and DMC (volume ratio: 10:10:80) and thereafter, sufficiently dried $LiPF_6$ was dissolved therein to account for a proportion of 1 mol/L, whereby an electrolyte solution base was prepared. To this electrolyte solution base, the compound (i) or (iii) to (v) was added in a ratio shown in Tables 2 and 3, and the obtained electrolyte solutions of Examples 7 to 14 were compared with those of Comparative Examples 8 to 10.

Incidentally, the positive electrode, the negative electrode and the secondary battery were produced by the same procedures as in Example 1.

[Evaluation of Initial Capacity]

The evaluation was performed under the same conditions as in Example 1 except for subjecting the battery to CCCV charging to 4.35 V in place of CCCV charging to 4.33 V.

[Evaluation of High-Temperature Storage Characteristics]

The evaluation was performed under the same conditions as in Example 1 except for subjecting the battery to CCCV charging to 4.35 V in place of CCCV charging to 4.33 V and performing high-temperature storage under the conditions of 75° C. and 72 hours in place of high-temperature storage under the conditions of 85° C. and 24 hours.

TABLE 1

| | Additive 1 | parts by mass | Additive 2 | parts by mass | Amount of Gas Evolved, % | Residual Capacity, % | Recovery Capacity, % |
|---|---|---|---|---|---|---|---|
| Example 1 | Compound (i) | 0.5 | none | — | 54.3 | 102.9 | 104.0 |
| Example 2 | Compound (ii) | 0.5 | none | — | 82.9 | 101.2 | 102.3 |
| Example 3 | Compound (iii) | 0.5 | none | — | 82.9 | 100.2 | 100.8 |
| Example 4 | Compound (iv) | 0.5 | none | — | 70.5 | 101.0 | 102.1 |
| Example 5 | Compound (v) | 0.5 | none | — | 52.8 | 100.7 | 101.0 |
| Example 6 | Compound (i) | 0.5 | adiponitrile | 0.5 | 48.8 | 107.0 | 105.1 |
| Comparative Example 1 | none | — | none | — | 100.0 | 100.0 | 100.0 |
| Comparative Example 2 | none | — | adiponitrile | 0.5 | 79.8 | 96.2 | 99.0 |
| Comparative Example 3 | Compound (vi) | 0.5 | none | — | 101.0 | 99.4 | 100.2 |
| Comparative Example 4 | Compound (vii) | 0.5 | none | — | 100.0 | 99.3 | 99.2 |
| Comparative Example 5 | Compound (viii) | 0.5 | none | — | 93.3 | 96.6 | 99.2 |
| Comparative Example 6 | Compound (x) | 0.5 | none | — | 101.9 | 100.4 | 102.2 |
| Comparative Example 7 | Compound (xi) | 0.5 | none | — | 79.8 | 99.1 | 99.5 |

* Relative values assuming that Comparative Example 1 is 100%.

As seen from Table 1, when the nonaqueous electrolyte solutions of Examples 1 to 6 according to the present invention are used, as compared with the case where the compound of formula (1) is not added (Comparative Examples 1 and 2), the amount of gas evolved during high-temperature storage is low and at the same time, the residual capacity•recovery capacity after high-temperature storage are excellent. Also, it is seen that use of alkanesulfonic acid ester, dialkylsulfonic acid ester, methyl vinylsulfonate or allyl allylsulfonate in place of the compound of formula (1) (Comparative Examples 3 to 7) fails in satisfying both prevention of gas evolution during high-temperature storage and enhancement of residual capacity•recovery capacity at the same time and such a compound is insufficient as the additive.

[Evaluation of Cycle Characteristics]

At 45° C., the nonaqueous electrolyte battery after the evaluation of initial capacity was subjected to CCCV charging to 4.4 V at 0.5 C and then to constant-current discharging to 3 V at 0.5 C. This operation was taken as one cycle, and 50 cycles were performed.

The discharge capacity retention ratio after 50 cycles was determined according to a calculation formula: (discharge capacity at 50th cycle)÷(discharge capacity at 1st cycle)× 100.

Using these nonaqueous electrolyte batteries, evaluation of high-temperature storage characteristics and evaluation of cycle characteristics were performed. Evaluation results are shown in Tables 2 and 3.

TABLE 2

| | Additive | parts by mass | Amount of Gas Evolved, % | Residual Capacity, % | Recovery Capacity, % |
|---|---|---|---|---|---|
| Example 7 | Compound (i) | 0.5 | 36.8 | 109.9 | 118.0 |
| Example 8 | Compound (iii) | 0.5 | 50.0 | 108.7 | 115.8 |
| Example 9 | Compound (iv) | 0.5 | 46.6 | 110.5 | 119.0 |
| Comparative Example 8 | none | — | 100.0 | 100.0 | 100.0 |

* Relative values assuming that Comparative Example 8 is 100%.

As seen from Table 2, when the nonaqueous electrolyte solutions of Examples 7 to 9 according to the present invention are used, as compared with the case where the compound of formula (1) is not added (Comparative Example 8), the amount of gas evolved during high-temperature storage is low and at the same time, the residual capacity•recovery capacity after high-temperature storage are excellent.

TABLE 3

| | Additive 1 | parts by mass | Additive 2 | parts by mass | Discharge Capacity Retention Ratio After 50 Cycles, % |
|---|---|---|---|---|---|
| Example 10 | Compound (i) | 0.5 | none | — | 105.4 |
| Example 11 | Compound (iv) | 0.5 | none | — | 103.3 |
| Example 12 | Compound (i) | 0.5 | 1,3-propanesultone | 1 | 105.8 |
| Example 13 | Compound (iv) | 0.5 | 1,3-propanesultone | 1 | 102.9 |
| Example 14 | Compound (v) | 0.5 | 1,3-propanesultone | 1 | 105.0 |
| Comparative Example 9 | none | — | none | — | 100.0 |
| Comparative Example 10 | none | — | 1,3-propanesultone | 1 | 102.3 |

* Relative values assuming that Comparative Example 9 is 100%.

As seen from Table 3, when the nonaqueous electrolyte solutions of Examples 10 to 14 according to the present invention are used, as compared with the case where the compound of formula (1) is not added (Comparative Examples 9 and 10), the discharge capacity retention ratio after 50 cycles is excellent.

Examples 15 to 17 and Comparative Examples 11 and 12

Battery Evaluation

[Preparation of Nonaqueous Electrolyte Solution]

In a dry argon atmosphere, fully dried $LiPF_6$ was dissolved in a mixture of EC and methyl ethyl carbonate (EMC) (volume ratio: 30:70) to account for a proportion of 1 mol/L, whereby an electrolyte solution base was prepared. To this electrolyte solution base, the compound was added in a ratio shown in Table 4 to prepare electrolyte solutions used in Examples 15 to 17 and Comparative Examples 11 and 12.

[Production of Positive Electrode]

The positive electrode was produced in the same manner as in Example 1 except for using 94 mass % of $LiCoO_2$, 3 mass % of acetylene black as an electrically conductive material and 3 mass % of PVdF as a binder in place of using 97 mass % of $LiCoO_2$ as a positive electrode active material, 1.5 mass % of acetylene black as an electrically conductive material and 1.5 mass % of PVdF as a binder in Example 1.

Incidentally, the negative electrode and the secondary battery were produced by the same method as in Example 1.

[Evaluation of Initial Capacity]

The evaluation was performed in the same manner as in Example 1 except for subjecting the battery to CCCV charging to 4.2 V in place of CCCV charging to 4.33 V.

[Evaluation of High-Temperature Storage Characteristics]

The evaluation was performed in the same manner as in Example 1 except for subjecting the battery to CCCV charging to 4.2 V in place of CCCV charging to 4.33 V and performing high-temperature storage under the conditions of 85° C. and 72 hours in place of high-temperature storage under the conditions of 85° C. and 24 hours, in Example 1.

Using these nonaqueous electrolyte batteries, evaluation of high-temperature storage characteristics was performed. Evaluation results are shown in Table 4.

TABLE 4

| | Additive | parts by mass | Amount of Gas Evolved, % | Residual Capacity, % | Recovery Capacity, % |
|---|---|---|---|---|---|
| Example 15 | Compound (i) | 0.5 | 25.3 | 103.1 | 101.5 |
| Example 16 | Compound (ii) | 0.5 | 42.6 | 101.4 | 101.0 |
| Example 17 | Compound (iv) | 0.5 | 44.2 | 100.7 | 100.2 |
| Comparative Example 11 | none | — | 100.0 | 100.0 | 100.0 |
| Comparative Example 12 | Compound (ix) | 0.5 | 24.3 | 96.1 | 94.6 |

* Relative values assuming that Comparative Example 11 is 100%.

As seen from Table 4, when the nonaqueous electrolyte solutions of Examples 15 to 17 according to the present invention are used, as compared with the case where the compound of formula (1) is not added (Comparative Example 11), the amount of gas evolved during high-temperature storage is low and at the same time, the residual capacity•recovery capacity after high-temperature storage are excellent.

Also, it is seen that use of an alkynyl alkanesulfonate compound in place of the compound of formula (1) (Comparative Example 12) fails in satisfying both prevention of gas evolution during high-temperature storage and enhancement of residual capacity•recovery capacity at the same time and the compound is insufficient as the additive.

Example 18 and Comparative Example 13

Battery Evaluation

[Preparation of Nonaqueous Electrolyte Solution]

In a dry argon atmosphere, 2 mass % of vinylene carbonate (VC), in terms of the content in the nonaqueous solution, was mixed with a mixture of EC, EMC and diethyl carbonate (DEC) (volume ratio: 20:30:50) and thereafter, sufficiently dried $LiPF_6$ was dissolved therein to account for a proportion of 1 mol/L, whereby an electrolyte solution base was prepared. To this electrolyte solution base, the compound was added in a ratio shown in Table 5 to prepare electrolyte solutions used in Example 18 and Comparative Example 13.

Incidentally, the positive electrode, the negative electrode and the secondary battery were produced in the same manner as in Example 15.

Using these nonaqueous electrolyte batteries, evaluation of high-temperature storage characteristics was performed in the same manner as in Example 15. Evaluation results are shown in Table 5.

TABLE 5

| | Additive | parts by mass | Amount of Gas Evolved, % | Residual Capacity, % | Recovery Capacity, % |
|---|---|---|---|---|---|
| Example 18 | Compound(i) | 0.2 | 66.7 | 102.3 | 102.2 |
| Comparative Example 13 | none | — | 100.0 | 100.0 | 100.0 |

* Relative value assuming that Comparative Example 13 is 100%.

As seen from Table 5, when the nonaqueous electrolyte solution of Example 18 according to the present invention is used as compared with the case where the compound of formula (1) is not added (Comparative Example 13), the amount of gas evolved during high-temperature storage is low and at the same time, the residual capacity•recovery capacity after high-temperature storage are excellent.

Examples 19 to 23 and Comparative Examples 14 to 16

Battery Evaluation

[Preparation of Nonaqueous Electrolyte Solution]

In a dry argon atmosphere, fully dried $LiPF_6$ was dissolved in a mixture of EC, DMC and EMC (volume ratio: 30:30:40) or a mixture of MFEC, DMC and EMC (volume ratio: 30:30:40) to account for a proportion of 1 mol/L, whereby an electrolyte solution base was prepared. To this electrolyte solution base, the compound was added in a ratio shown in Table 6 to prepare electrolyte solutions used in Examples 19 to 23 and Comparative Examples 14 to 16.

[Production of Positive Electrode]

In an N-methylpyrrolidone solvent, 90 mass % of $Li(Ni_{1/3}Mn_{1/3}Co_{1/3})O_2$ as a positive electrode active material, 5 mass % of acetylene black as an electrically conductive material and 5 mass % of PVdF as a binder were mixed by means of a disperser to make a slurry. This slurry was uniformly coated on both surfaces of a 15 μm-thick aluminum foil, then dried and pressed to produce a positive electrode.

Incidentally, the negative electrode and the secondary battery were produced in the same manner as in Example 1.

[Evaluation of Initial Capacity]

The evaluation was performed under the same conditions as in Example 1 except for subjecting the battery to CCCV charging to 4.4 V in place of CCCV charging to 4.33 V.

[Evaluation of Cycle Characteristics]

At 60° C., the nonaqueous electrolyte battery after the evaluation of initial capacity was subjected to CC charging to 4.4 V at 2 C and then to constant-current discharging to 3 V at 2 C. This operation was taken as one cycle, and 300 cycles were performed.

The discharge capacity retention ratio after 300 cycles was determined according to a calculation formula: (discharge capacity at 300th cycle)+(discharge capacity at 1st cycle)×100.

Using these nonaqueous electrolyte batteries, evaluation of cycle characteristics was performed. Evaluation results are shown in Table 6.

TABLE 6

| | Electrolyte Solution | Additive 1 | parts by mass | Additive 2 | parts by mass | Discharge Capacity Retention Ratio after 300 Cycles, % |
|---|---|---|---|---|---|---|
| Example 19 | 1M $LiPF_6$ EC/DMC/EMC = 3/3/4 | Compound (i) | 1 | none | — | 109.4 |
| Example 20 | 1M $LiPF_6$ EC/DMC/EMC = 3/3/4 | Compound (i) | 1 | MFEC | 3 | 120.2 |
| Example 21 | 1M $LiPF_6$ EC/DMC/EMC = 3/3/4 | Compound (iii) | 1 | MFEC | 3 | 113.1 |
| Example 22 | 1M $LiPF_6$ MFEC/DMC/EMC = 3/3/4 | Compound (i) | 1 | none | — | 118.1 |
| Example 23 | 1M $LiPF_6$ MFEC/DMC/EMC = 3/3/4 | Compound (iii) | 1 | none | — | 111.1 |
| Comparative Example 14 | 1M $LiPF_6$ EC/DMC/EMC = 3/3/4 | none | — | none | — | 100.0 |
| Comparative Example 15 | 1M $LiPF_6$ EC/DMC/EMC = 3/3/4 | none | — | MFEC | 3 | 87.4 |
| Comparative Example 16 | 1M $LiPF_6$ MFEC/DMC/EMC = 3/3/4 | none | — | none | — | 108.4 |

* Relative values assuming that Comparative Example 14 is 100%.

As seen from Table 6, when the nonaqueous electrolyte solutions of Examples 19 to 23 according to the present invention are used, as compared with the case where the compound of formula (1) is not added (Comparative Examples 14 to 16), the discharge capacity retention ratio after 300 cycles is excellent.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2010-233513) filed on Oct. 18, 2010, the contents of which are incorporated herein by way of reference.

INDUSTRIAL APPLICABILITY

According to the nonaqueous electrolyte solution of the present invention, capacity deterioration and gas evolution during high-temperature storage of a nonaqueous electrolyte battery can be improved. Therefore, the nonaqueous electrolyte solution of the present invention and a nonaqueous electrolyte battery using the same can be used for various known applications.

Specific examples of the application include a notebook computer, a pen-input computer, a mobile computer, an electronic book player, a cellular phone, a portable facsimile, a portable copier, a portable printer, a headphone stereo, a video movie, a liquid crystal TV, a handy cleaner, a portable CD, a mini disk, a transceiver, an electronic notebook, an electric calculator, a memory card, a portable tape recorder, a radio, a backup power source, a motor, a car, a motorcycle, a motorized bicycle, a bicycle, a lighting fixture, a toy, a game machine, a clock, an electric tool, a strobe, a camera, a power source for load leveling, and a power source of natural energy storage.

The invention claimed is:

1. A nonaqueous electrolyte solution comprising a lithium salt and a nonaqueous organic solvent, wherein said nonaqueous electrolyte solution comprises a sulfonic acid ester of the formula (1):

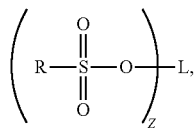

(1)

wherein L represents a Z-valent organic group which may have a substituent;

R represents a chain hydrocarbon group having an unsaturated bond, which may have a substituent; and Z is an integer of 1 or more, and when Z is 2 or more, each R may be the same or different, wherein when Z is 1, L is an alkynyl group; and wherein R and L do not combine with each other to form a ring.

2. The nonaqueous electrolyte solution as claimed in claim 1, wherein in the formula (1), L is an organic group selected from the group consisting of an alkyl group, an alkylene group, an alkenyl group, an alkenylene group, an alkynyl group and an alkynylene group, each having a carbon number of 1 to 8, which may have a substituent, and R is an alkenyl group or an alkynyl group, each having a carbon number of 2 to 8, which may have a substituent.

3. The nonaqueous electrolyte solution as claimed in claim 1, wherein in the formula (1), L is an organic group selected form the group consisting of an alkylene group, an alkenyl group, an alkenylene group, an alkynyl group and an alkynylene group, which may have a substituent, and R is a vinyl group.

4. The nonaqueous electrolyte solution as claimed in claim 1, which comprises from 0.001 to 10 mass % of said sulfonic acid ester represented by the formula (1).

5. The nonaqueous electrolyte solution as claimed in claim 1, which comprises said sulfonic acid ester represented by the formula (1) and at least one compound selected from the group consisting of a fluorine atom-containing cyclic carbonate, a carbon-carbon unsaturated bond-containing cyclic carbonate, a monofluorophosphate, a difluorophosphate, an isocyanate compound, a cyclic sulfonic acid ester, an oxalate salt and a nitrile compound.

6. The nonaqueous electrolyte solution as claimed in claim 5, which comprises from 5 to 90 mass % of a fluorine atom-containing cyclic carbonate.

7. The nonaqueous electrolyte solution as claimed in claim 5, wherein the fluorine atom-containing cyclic carbonate is at least one compound selected from the group consisting of monofluoroethylene carbonate, 4,4-difluoroethylene carbonate, 4,5-difluoroethylene carbonate and 4,5-difluoro-4,5-dimethylethylene carbonate.

8. A nonaqueous electrolyte battery comprising negative and positive electrodes capable of occluding-releasing a lithium ion and a nonaqueous electrolyte solution, wherein said nonaqueous electrolyte solution is the nonaqueous electrolyte solution of claim 1.

* * * * *